United States Patent
Komatsu et al.

(10) Patent No.: US 7,134,328 B2
(45) Date of Patent: Nov. 14, 2006

(54) LIQUID-EJECTION TESTING METHOD, LIQUID-EJECTION TESTING DEVICE, AND COMPUTER-READABLE MEDIUM

(75) Inventors: Shinya Komatsu, Nagano-ken (JP); Yuichi Nishihara, Nagano-ken (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 11/270,620

(22) Filed: Nov. 10, 2005

(65) Prior Publication Data
US 2006/0101926 A1 May 18, 2006

(30) Foreign Application Priority Data
Nov. 10, 2004 (JP) .............................. 2004-327118
Nov. 25, 2004 (JP) .............................. 2004-340541

(51) Int. Cl.
*B41J 29/393* (2006.01)
(52) U.S. Cl. .......................................... 73/168; 347/19
(58) Field of Classification Search .................. None
See application file for complete search history.

(56) References Cited
U.S. PATENT DOCUMENTS
2004/0207676 A1* 10/2004 Yamada et al. ............... 347/19
2005/0212844 A1* 9/2005 Nishihara ..................... 347/19

FOREIGN PATENT DOCUMENTS
JP 11-170569 A 6/1999
JP 2000-233520 A 8/2000

* cited by examiner

*Primary Examiner*—Robert Raevis
(74) *Attorney, Agent, or Firm*—Sughrue Mion, PLLC

(57) ABSTRACT

A liquid-ejection testing method includes the following steps (A) to (D): (A) A step of making at least two conductive detection members be opposed, in a non-contact state, to a plurality of liquid ejecting nozzles that are to be tested, the detection members being opposed in a direction that intersects with a direction in which the plurality of liquid ejecting nozzles are arranged, each detection member corresponding to a different liquid ejecting nozzle. (B) A step of ejecting a charged liquid from each of the plurality of liquid ejecting nozzles. (C) A step of detecting an induced current generated at each of the detection members by the liquid that has been ejected from each of the liquid ejecting nozzles (D) A step of judging whether or not ejection of the liquid is being properly performed for each of the plurality of liquid ejecting nozzles, based on a magnitude of the induced current that has been detected.

17 Claims, 45 Drawing Sheets

|  |  | test target ||
|---|---|---|---|
|  |  | nozzles close to detection members | nozzles away from detection members |
| test 1 (presence/ absence of ejection) | reference value | V0H | V0L |
| test 2 (ejection direction) | minimum tolerance value | V1H | V1L |
|  | maximum tolerance value | V2H | V2L |

Fig.22C

|  |  | test target | |
|---|---|---|---|
|  |  | nozzles close to detection members | nozzles away from detection members |
| test 1 (presence/ absence of ejection) | reference value | V0H | V0L |
| test 2 (ejection direction) | minimum tolerance value | V1H | V1L |
|  | maximum tolerance value | V2H | V2L |

Fig.30C

LIQUID-EJECTION TESTING METHOD, LIQUID-EJECTION TESTING DEVICE, AND COMPUTER-READABLE MEDIUM

CROSS-REFERENCE TO RELATED APPLICATIONS

The present application claims priority upon Japanese Patent Application No. 2004-327118 filed on Nov. 10, 2004, and Japanese Patent Application No. 2004-340541 filed on Nov. 25, 2004, which are herein incorporated by reference.

BACKGROUND OF THE INVENTION

1. Field of the Invention

The present invention relates to liquid-ejection testing methods, liquid-ejection testing devices, and computer-readable media.

2. Description of the Related Art

<No. 1>

Inkjet printers are known as printing apparatuses for carrying out printing by ejecting ink onto various media such as paper, cloth, and film. Inkjet printers perform color printing by ejecting ink of various colors such as cyan (C), magenta (M), yellow (Y), and black (K) to form dots on the medium. Ink is ejected using nozzles.

However, in these inkjet printers, clogging can occur in the nozzles due to adherence of the ink for example, and the ink may not be ejected properly. When ink cannot be ejected properly from the nozzles, dots cannot be formed appropriately on the medium, and this results in the trouble that an image will not be printed clearly.

Thus, various methods for testing whether or not ink is properly ejected have been conventionally proposed. As one method, a testing method for optically detecting ink ejected from the nozzles has been proposed (see JP 2000-233520A). In this testing method, a photodiode detects whether or not a beam emitted from an LED is blocked by ink ejected from a nozzle, so that whether or not ink is ejected from the nozzle is checked.

<Problem 1>

However, this testing method has the problems as follows. It is very difficult to positionally align a beam emitted from an LED and ink ejected from a nozzle. When ink is ejected from the nozzle in a curve, it is impossible to detect ink ejection, and thus it may be impossible to accurately detect whether ink is being ejected or not.

<Problem 2>

Furthermore, in the ejection test that has been conventionally carried out, a method in which the ejection test is performed row by row on a plurality of nozzle rows arranged in the head while moving the head relative to the testing device has been employed. In this method for performing the ejection test one by one on the rows, it is necessary to move the head each time the test target is switched from one nozzle row to another nozzle row. Thus, it takes considerable time to perform the ejection test because of the time required for moving the head and the time for positionally aligning the nozzle rows arranged in the head and the testing device. When such an ejection test is performed, it is preferable to make the movement of the head small to the extent possible.

SUMMARY OF THE INVENTION

The present invention was arrived at in light of these circumstances. It is a first object thereof to easily and efficiently check whether or not a liquid is properly ejected from nozzles from which a liquid such as ink is ejected. Furthermore, it is a second object thereof to shorten the time for the test by efficiently performing the ejection test on a liquid ejecting section that ejects a liquid such as ink.

A primary aspect of the present invention is a liquid-ejection testing method such as the following.

A liquid-ejection testing method, includes:

a step of making at least two conductive detection members be opposed, in a non-contact state, to a plurality of liquid ejecting nozzles that are to be tested, the detection members being opposed in a direction that intersects with a direction in which the plurality of liquid ejecting nozzles are arranged, each detection member corresponding to a different liquid ejecting nozzle, a step of ejecting a charged liquid from each of the plurality of liquid ejecting nozzles, a step of detecting an induced current generated at each of the detection members by the liquid that has been ejected from each of the liquid ejecting nozzles, and a step of judging whether or not ejection of the liquid is being properly performed for each of the plurality of liquid ejecting nozzles, based on a magnitude of the induced current that has been detected.

Furthermore, another primary aspect of the present invention is a liquid-ejection testing device such as the following.

A liquid-ejection testing device, includes:

at least two conductive detection members that are arranged in a direction that intersects with a direction in which a plurality of liquid ejecting nozzles that are to be tested are arranged, the at least two detection members being arranged in a state of non-contact with respect to the plurality of liquid ejecting nozzles, each of the detection members being provided corresponding to a different liquid ejecting nozzle, a detecting section for detecting an induced current generated at each of the detection members by a charged liquid ejected from each of the plurality of liquid ejecting nozzles, and a judging section for judging whether or not ejection of the liquid is being properly performed for each of the plurality of liquid ejecting nozzles, based on a magnitude of the induced current that has been detected by the detecting section.

Furthermore, another primary aspect of the present invention is a computer-readable medium such as the following.

A computer-readable medium for causing a liquid-ejection testing device to operate, includes:

a code for ejecting a charged liquid from each of a plurality of liquid ejecting nozzles that are to be tested and that are arranged in a predetermined direction, a code for acquiring a magnitude of an induced current generated by the liquid that has been ejected from each of the liquid ejecting nozzles at at least two conductive detection members that are arranged in a direction that intersects with the predetermined direction, the detection members being arranged in a state of non-contact with respect to the plurality of liquid ejecting nozzles, each detection member corresponding to a different liquid ejecting nozzle, and a code for judging whether or not ejection of the liquid is being properly performed for each of the plurality of liquid ejecting nozzles, based on the magnitude of the induced current that has been acquired.

Furthermore, another primary aspect of the present invention is a liquid-ejection testing method such as the following.

A liquid-ejection testing method, includes:

a step of making a first testing section be opposed to one liquid ejecting section among a plurality of liquid ejecting sections that are to be tested and that are arranged in a predetermined direction with a spacing between one another on a head that can move in the predetermined direction, and testing, with the first testing section, whether or not ejection of a liquid is being properly performed for the one liquid ejecting section, and a step of testing, with a second testing section, whether or not ejection of a liquid is being properly performed for an other liquid ejecting section among the plurality of liquid ejecting sections in a state where the one liquid ejecting section and the first testing section are opposed to each other, the second testing section being arranged with a spacing from the first testing section in the predetermined direction, the spacing corresponding to a spacing between the one liquid ejecting section and the other liquid ejecting section.

BRIEF DESCRIPTION OF THE DRAWINGS

For a more complete understanding of the present invention and the advantages thereof, reference is now made to the following description taken in conjunction with the accompanying drawings.

FIG. 22C is a table in which reference values are summarized.

FIG. 30C is a table in which reference values are summarized.

Figure 1:
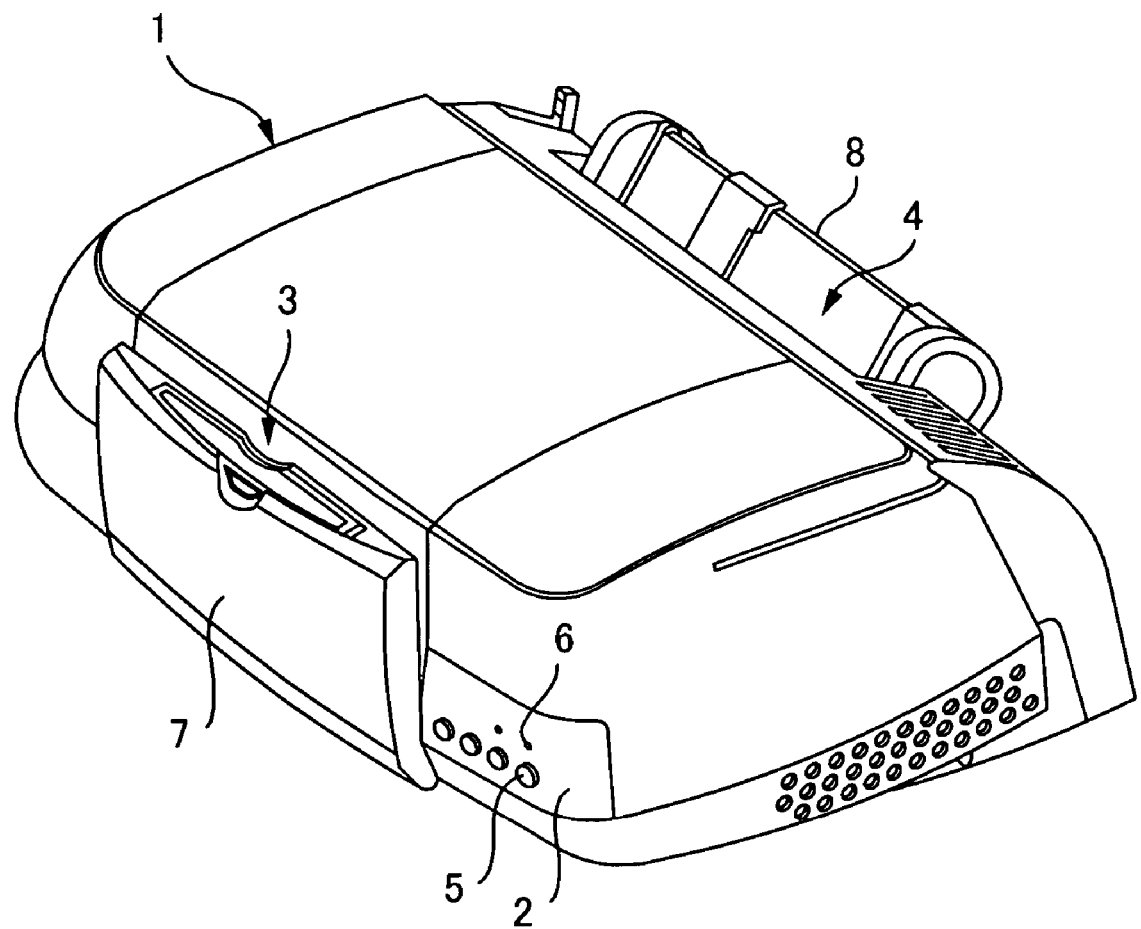
FIG. 1 is a perspective view of an embodiment of a printing apparatus.

DETAILED DESCRIPTION OF THE INVENTION DETAILED DESCRIPTION OF THE PREFERRED EMBODIMENTS

At least the following matters will be made clear by the explanation in the present specification and the description of the accompanying drawings.

A liquid-ejection testing method, includes:

a step of making at least two conductive detection members be opposed, in a non-contact state, to a plurality of liquid ejecting nozzles that are to be tested, the detection members being opposed in a direction that intersects with a direction in which the plurality of liquid ejecting nozzles are arranged, each detection member corresponding to a different liquid ejecting nozzle, a step of ejecting a charged liquid from each of the plurality of liquid ejecting nozzles, a step of detecting an induced current generated at each of the detection members by the liquid that has been ejected from each of the liquid ejecting nozzles, and a step of judging whether or not ejection of the liquid is being properly performed for each of the plurality of liquid ejecting nozzles, based on a magnitude of the induced current that has been detected.

In this liquid-ejection testing method, a magnitude of an induced current generated at the detection members with a charged liquid that has been ejected from the liquid ejecting nozzles is detected to judge whether or not ejection of the liquid is being properly performed based on the magnitude of the induced current that has been detected. Thus, it is possible to easily perform the ejection test on the liquid ejecting nozzles. Furthermore, each of the detection members is disposed in correspondence with the different liquid ejecting nozzles. Accordingly, it is possible to perform the ejection test on the liquid ejecting nozzles at one time, and thus it is possible to make the test operation more efficient, so that the time for the test can be shortened.

In the liquid-ejection testing method, it is preferable that the detection members are made of a plate-shaped member or a wire material.

When the detection members are made of a plate-shaped member or a wire material in this manner, it is possible to easily let an induced current be generated at the detection members with a liquid that has been ejected from the liquid ejecting nozzles.

In the liquid-ejection testing method, it is preferable that the at least two detection members are arranged in parallel to each other.

When the at least two detection members are arranged in parallel to each other in this manner, it is possible to efficiently perform the test on the plurality of liquid ejecting nozzles.

In the liquid-ejection testing method, it is preferable that spacings between the at least two detection members are equal to each other.

When spacings between the at least two detection members are equal to each other in this manner, it is possible to efficiently perform the test on the plurality of liquid ejecting nozzles.

In the liquid-ejection testing method, it is preferable that the at least two detection members span over an opening section provided in a substrate.

When the at least two detection members are arranged at an opening section of a substrate in this manner, it is possible to easily provide the at least two detection members.

In the liquid-ejection testing method, it is preferable that the at least two detection members are electrically connected to each other via a common line.

When the at least two detection members are electrically connected to each other via a common line in this manner, it is possible to easily perform the test.

In the liquid-ejection testing method, it is preferable that the common line is connected to a detecting section for detecting the induced current that has been generated at the detection members.

When the common line is connected to this detecting section, it is possible to easily detect an induced current that has been generated at the detection members.

In the liquid-ejection testing method, it is preferable that the common line is connected to one end portion of each of the detection members.

When the common line is connected to one end portion of each of the detection members in this manner, it is possible to simplify the configuration.

In the liquid-ejection testing method, it is preferable that judgment is performed by comparing the magnitude of the induced current that has been detected and a predetermined reference value.

When judgment is performed by comparing a magnitude of the induced current that has been detected and a predetermined reference value in this manner, it is possible to easily perform the test.

In the liquid-ejection testing method, it is preferable that whether or not the liquid is ejected from the liquid ejecting nozzles is judged based on the magnitude of the induced current that has been detected.

When whether or not the liquid is ejected from the liquid ejecting nozzles is judged in this manner based on a magnitude of the induced current that has been detected, it is possible to easily test whether or not the liquid is ejected.

In the liquid-ejection testing method, it is preferable that whether or not an ejection direction of the liquid from the liquid ejecting nozzles is proper is judged based on the magnitude of the induced current that has been detected.

When whether or not an ejection direction of the liquid from the liquid ejecting nozzles is proper is judged in this manner based on a magnitude of the induced current that has been detected, it is possible to easily test whether or not an ejection direction of the liquid is proper.

In the liquid-ejection testing method, it is preferable that a voltage is applied to the detection members in order to charge the liquid ejected from the liquid ejecting nozzles.

When a voltage is applied to the detection members in this manner, it is possible to easily charge the liquid ejected from the liquid ejecting nozzles.

In the liquid-ejection testing method, it is preferable that the liquid ejected from the liquid ejecting nozzles is charged by an electrode section to which a voltage is applied.

When this electrode section is used, it is possible to easily charge the liquid ejected from the liquid ejecting nozzles.

It is preferable that the liquid-ejection testing method further comprises a step of changing a relative position between the plurality of liquid ejecting nozzles and the at least two detection members.

When a step of changing a relative position between the plurality of liquid ejecting nozzles and the at least two detection members is provided in this manner, it is possible to change the test position.

Furthermore, it is also possible to achieve a liquid-ejection testing device such as the following.

A liquid-ejection testing device, includes:

at least two conductive detection members that are arranged in a direction that intersects with a direction in which a plurality of liquid ejecting nozzles that are to be tested are arranged, the at least two detection members being arranged in a state of non-contact with respect to the plurality of liquid ejecting nozzles, each of the detection members being provided corresponding to a different liquid ejecting nozzle, a detecting section for detecting an induced current generated at each of the detection members by a charged liquid ejected from each of the plurality of liquid ejecting nozzles, and a judging section for judging whether or not ejection of the liquid is being properly performed for each of the plurality of liquid ejecting nozzles, based on a magnitude of the induced current that has been detected by the detecting section.

In this liquid-ejection testing device, a magnitude of an induced current generated at the detection members with a charged liquid that has been ejected from the liquid ejecting nozzles is detected to judge whether or not ejection of a liquid is being properly performed based on the magnitude of the induced current that has been detected. Thus, it is possible to easily perform the ejection test on the liquid ejecting nozzles. Furthermore, each of the detection members is disposed in correspondence with the different liquid ejecting nozzles. Accordingly, it is possible to perform the ejection test on the liquid ejecting nozzles at one time, and thus it is possible to make the test operation more efficient, so that the time for the test can be shortened.

In the liquid-ejection testing device, it is preferable that the plurality of liquid ejecting nozzles eject ink as the liquid and are arranged in a printing apparatus.

When the plurality of liquid ejecting nozzles eject ink as the liquid and are arranged at a printing apparatus in this manner, it is possible to judge whether or not ink is properly ejected. Furthermore, it is possible to perform the ejection test at one time, so that the time for the test can be shortened.

Furthermore, it is also possible to achieve a computer-readable medium such as the following.

A computer-readable medium for causing a liquid-ejection testing device to operate, includes:

a code for ejecting a charged liquid from each of a plurality of liquid ejecting nozzles that are to be tested and that are arranged in a predetermined direction, a code for acquiring a magnitude of an induced current generated by the liquid that has been ejected from each of the liquid ejecting nozzles at at least two conductive detection members that are arranged in a direction that intersects with the predetermined direction, the detection members being arranged in a state of non-contact with respect to the plurality of liquid ejecting nozzles, each detection member corresponding to a different liquid ejecting nozzle, and a code for judging whether or not ejection of the liquid is being properly performed for each of the plurality of liquid ejecting nozzles, based on the magnitude of the induced current that has been acquired.

In this computer-readable medium, a magnitude of an induced current generated at the detection members with a charged liquid that has been ejected from the liquid ejecting nozzles is detected to judge whether or not ejection of a liquid is being properly performed based on the magnitude of the induced current that has been detected. Thus, it is possible to easily perform the ejection test on the liquid ejecting nozzles. Furthermore, each of the detection members is disposed in correspondence with the different liquid ejecting nozzles. Accordingly, it is possible to perform the ejection test on the liquid ejecting nozzles at one time, and thus it is possible to make the test operation more efficient, so that the time for the test can be shortened.

Furthermore, it is also possible to achieve a liquid-ejection testing method as the following.

A liquid-ejection testing method, includes:

a step of making a first testing section be opposed to one liquid ejecting section among a plurality of liquid ejecting sections that are to be tested and that are arranged in a predetermined direction with a spacing between one another on a head that can move in the predetermined direction, and testing, with the first testing section, whether or not ejection of a liquid is being properly performed for the one liquid ejecting section, and a step of testing, with a second testing section, whether or not ejection of a liquid is being properly performed for an other liquid ejecting section among the plurality of liquid ejecting sections in a state where the one liquid ejecting section and the first testing section are opposed to each other, the second testing section being arranged with a spacing from the first testing section in the predetermined direction, the spacing corresponding to a spacing between the one liquid ejecting section and the other liquid ejecting section.

In this liquid-ejection testing method, the first testing section and the second testing section for performing the test on the plurality of liquid ejecting sections that are arranged on the head, are arranged with a spacing therebetween in a movement direction of the head, and the spacing corresponds to a spacing of two predetermined liquid ejecting sections among the plurality of liquid ejecting sections. Thus, the first testing section and the second testing section can perform the test on two liquid ejecting sections, so that it is possible to efficiently perform the test on the liquid ejecting sections.

In the liquid-ejection testing method, it is preferable that the first testing section and the second testing section perform the test when the head is stopped at a predetermined position.

When the test is performed in this manner when the head is stopped at a predetermined position, it is possible to smoothly perform the test.

In the liquid-ejection testing method, it is preferable that there are a plurality of the predetermined positions, and the head moves in the predetermined direction in order to change the predetermined positions.

When there are a plurality of predetermined positions and the head moves in the predetermined direction in order to change the predetermined position in this manner, it is possible to smoothly perform the test on the plurality of liquid ejecting sections.

===Outline of Liquid Ejecting Apparatus and Printing Apparatus===

Figure 2:
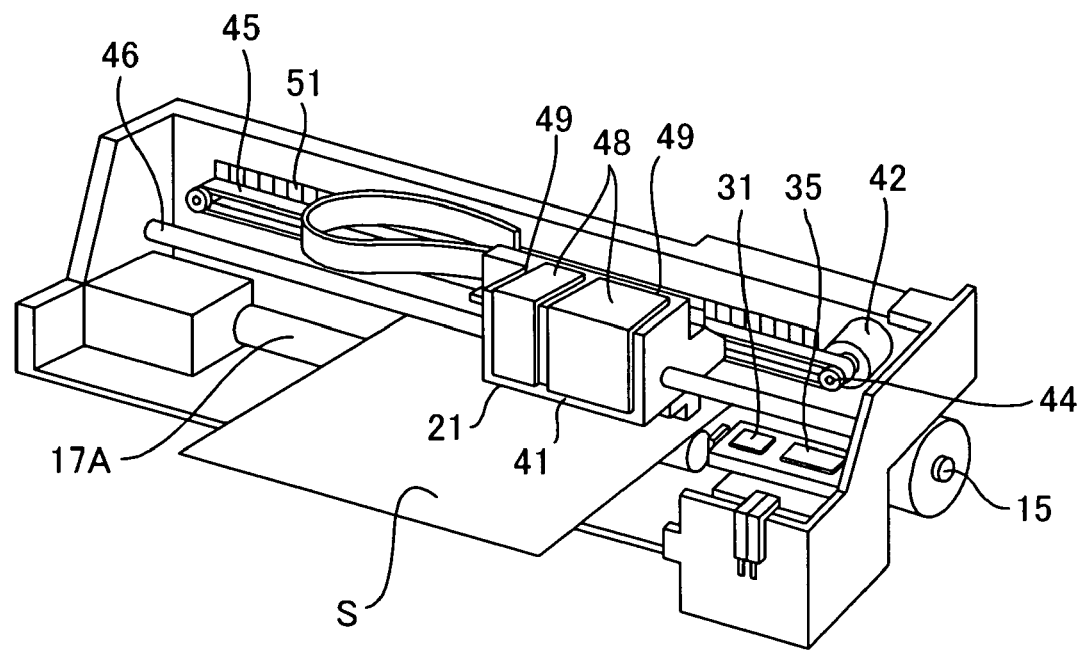
FIG. 2 is a perspective view illustrating the internal configuration of the printing apparatus.
Figure 2:
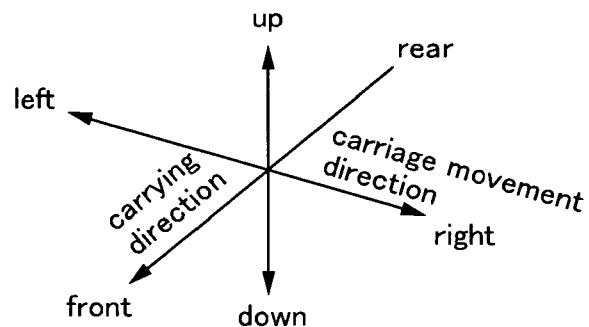
Figure 3:
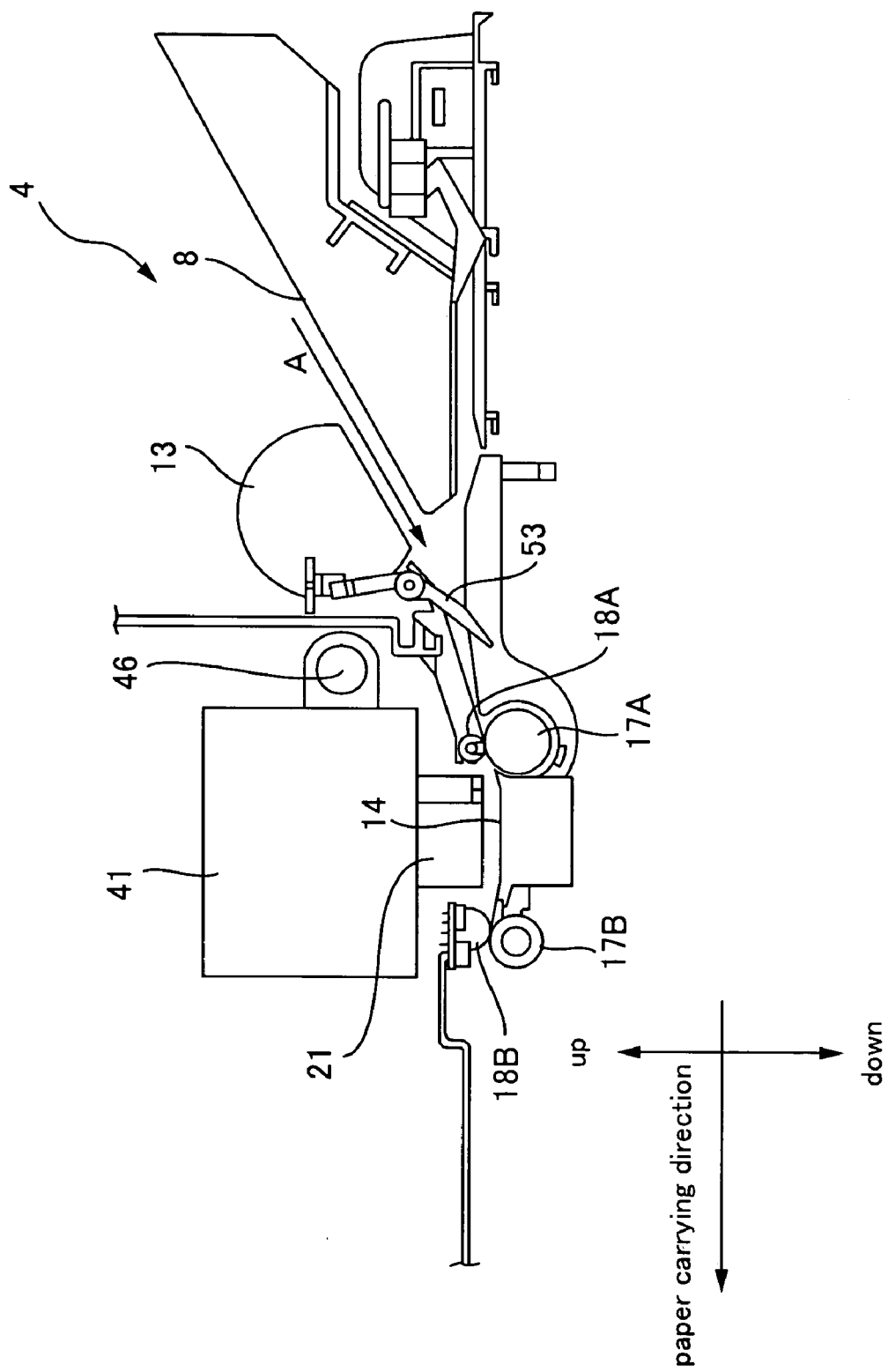
FIG. 3 is a cross-sectional view showing a carrying section of the printing apparatus.
Figure 4:
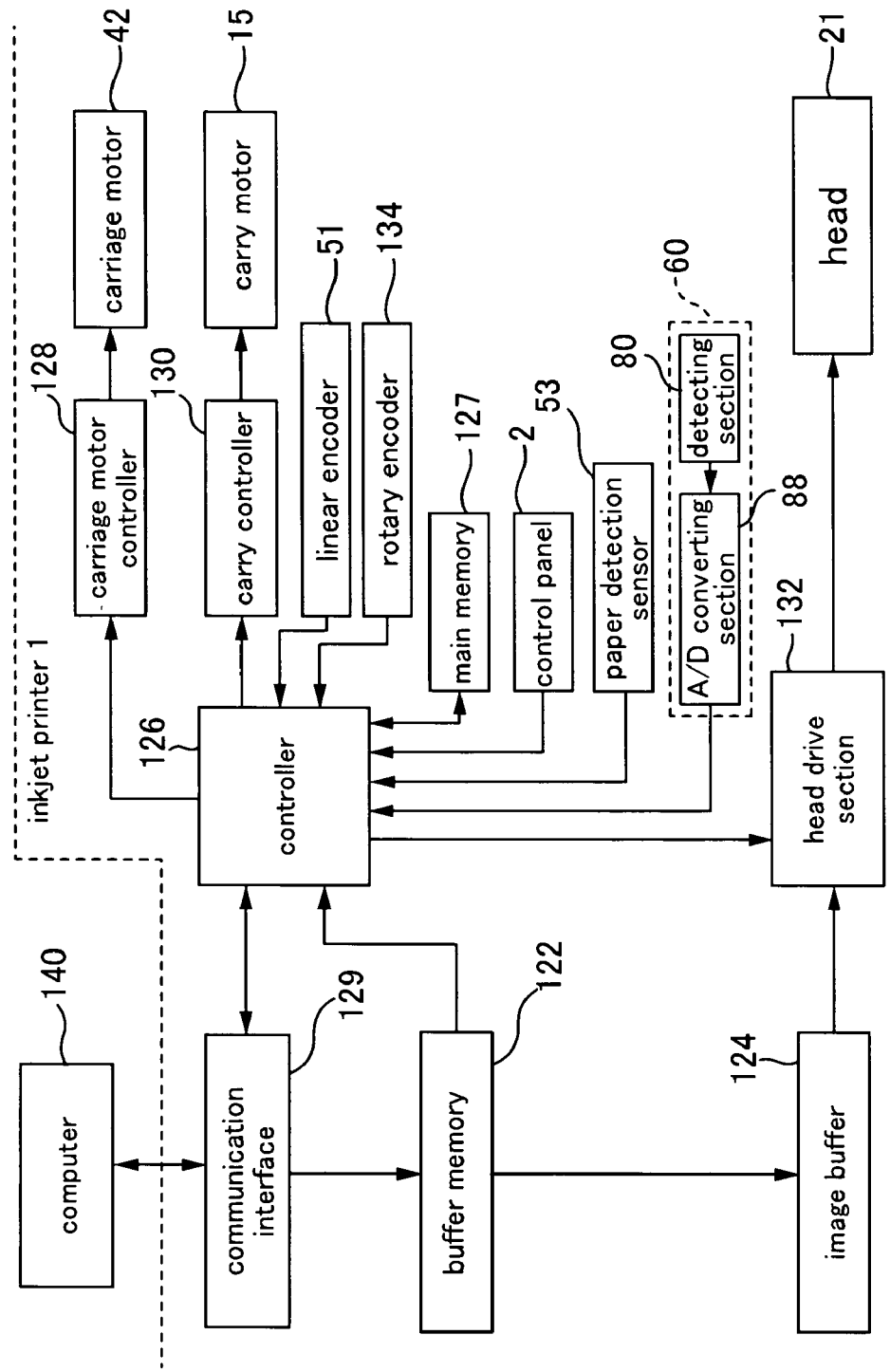
FIG. 4 is a block diagram showing the system configuration of the printing apparatus.

An embodiment of a liquid ejecting apparatus and a printing apparatus according to the present invention is described by taking an inkjet printer 1 as an example. FIGS. 1 to 4 show the inkjet printer 1. FIG. 1 shows the appearance of the inkjet printer 1. FIG. 2 shows the internal configuration of the inkjet printer 1. FIG. 3 shows the configuration of a carrying section of the inkjet printer 1. FIG. 4 shows the system configuration of the inkjet printer 1.

As shown in FIG. 1, the inkjet printer 1 is provided with a structure in which a medium such as print paper that is supplied from the rear face is discharged from the front face. The front face portion is provided with a control panel 2 and a paper discharge section 3, and the rear face portion is provided with a paper supply section 4. The control panel 2 is provided with various types of control buttons 5 and display lamps 6. Furthermore, the paper discharge section 3 is provided with a paper discharge tray 7 that blocks the paper discharge opening when the inkjet printer is not used. The paper supply section 4 is provided with a paper supply tray 8 for holding a medium such as cut paper.

As shown in FIG. 2, the internal portion of the inkjet printer 1 is provided with a carriage 41. The carriage 41 is disposed such that it can move relatively in the left-to-right direction. A carriage motor 42, a pulley 44, a timing belt 45, and a guide rail 46 are arranged in the vicinity of the carriage 41. The carriage motor 42 is constituted by a DC motor or the like and functions as a driving force for moving the carriage 41 relatively in the left-to-right direction (hereinafter, also referred to as "carriage movement direction"). The timing belt 45 is connected via the pulley 44 to the carriage motor 42, and a part of it is also connected to the carriage 41, such that the carriage 41 is moved relatively in the carriage movement direction (left-to-right direction) with the rotational force of the carriage motor 42. The guide rail 46 guides the carriage 41 in the carriage movement direction (left-to-right direction).

In addition to the above, a linear encoder 51 for detecting the position of the carriage 41, a carry roller 17A for carrying a medium S in the direction (front-to-rear direction in the drawing, and hereinafter, also referred to as "carrying direction") that intersects with the movement direction of the carriage 41, and a carry motor 15 for rotatively driving the carry roller 17A are arranged in the vicinity of the carriage 41.

On the other hand, the carriage 41 is provided with ink cartridges 48 that contain various types of ink and a head 21 that carries out printing on the medium S. The ink cartridges 48 contain ink of various colors such as yellow (Y), magenta (M), cyan (C), and black (K), and are mounted in a cartridge mounting section 49 provided in the carriage 41 in a removable manner. Furthermore, in this embodiment, the head 21 carries out printing by ejecting ink onto the medium S. For this reason, the head 21 is provided with a large number of nozzles for ejecting ink.

In addition to the above, the internal portion of the inkjet printer 1 is provided with, for example, a pump device 31 for pumping ink from the nozzles such that clogging in the nozzles of the head 21 is eliminated, and a capping device 35 for capping the nozzles of the head 21 when printing is not being carried out (when being on standby, for example) such that clogging in the nozzles of the head 21 is prevented.

The following is a description concerning a carrying section of the inkjet printer 1. As shown in FIG. 3, the carrying section is provided with a paper supply roller 13, a paper detection sensor 53, the carry roller 17A, a paper discharge roller 17B, a platen 14, and free rollers 18A and 18B.

The medium S to be printed is set at the paper supply tray 8. The medium S that has been set at the paper supply tray 8 is carried along the arrow A in the drawing by the paper supply roller 13, which has a substantially D-shaped cross-section, and is sent into the internal portion of the inkjet printer 1. The medium S that has been sent into the internal portion of the inkjet printer 1 is brought into contact with the paper detection sensor 53. This paper detection sensor 53 is positioned between the paper supply roller 13 and the carry roller 17A, so that it detects the medium S that has been supplied by the paper supply roller 13.

The medium S that has been detected by the paper detection sensor 53 is carried by the carry roller 17A one by one to the platen 14 on which printing is carried out. The free roller 18A is disposed at the position opposed to the carry roller 17A. The medium S is placed between the free roller 18A and the carry roller 17A such that the medium S is smoothly carried.

The medium S that has been sent onto the platen 14 is one by one printed with ink ejected from the head 21. The platen 14 is disposed so as to be opposed to the head 21 and supports the medium S to be printed from the below.

The medium S on which printing has been carried out is discharged by the paper discharge roller 17B one by one to the outside of the printer. The paper discharge roller 17B is driven in synchronization with the carry motor 15, and discharges the medium S to the outside of the printer by holding the medium S between the paper discharge roller 17B and the free roller 18B that is disposed so as to be opposed to this paper discharge roller 17B.

<System Configuration>

The following is a description concerning the system configuration of the inkjet printer 1. As shown in FIG. 4, the inkjet printer 1 is provided with a buffer memory 122, an image buffer 124, a controller 126, a main memory 127, a communication interface 129, a carriage motor controller 128, a carry controller 130, and a head drive section 132.

The communication interface 129 is used by the inkjet printer 1 to exchange data with an external computer 140 such as a personal computer. The communication interface 129 is connected to the external computer 140 such that wired or wireless communications are possible, and receives various types of data such as print data transmitted from the computer 140.

The various types of data such as print data received by the communication interface 129 is temporarily stored in the buffer memory 122. Furthermore, the print data stored in the buffer memory is sequentially stored in the image buffer 124. The print data stored in the image buffer 124 is sequentially sent to the head drive section 132. Furthermore, the main memory 127 is constituted by a ROM, a RAM, or an EEPROM for example. Various programs for controlling the inkjet printer 1 and various types of setting data, for example, are stored in the main memory 127.

The controller 126 reads out control programs and various types of setting data from the main memory 127 and performs overall control of the inkjet printer 1 in accordance with the control programs and the various types of setting data. Furthermore, detection signals from various sensors such as a rotary encoder 134, the linear encoder 51, and the paper detection sensor 53 are input to the controller 126.

When various types of data such as print data that has been sent from the external computer 140 is received by the communication interface 129 and is stored in the buffer memory 122, the controller 126 reads out necessary information from among the stored data from the buffer memory 122. Based on the information that is read out, the controller 126 controls each of the carriage motor controller 128, the carry controller 130, and the head drive section 132, for example, in accordance with control programs while referencing output from the linear encoder 51 and the rotary encoder 134.

The carriage motor controller 128 controls the drive such as the rotation direction, the rotation number, and the torque of the carriage motor 42 in accordance with instructions from the controller 126. The carry controller 130 controls the drive of, for example, the carry motor 15 for rotatively driving the carry roller 17A in accordance with instructions from the controller 126.

The head drive section 132 controls the drive of the color nozzles provided at the head 21 in accordance with instructions from the controller 126 and based on print data stored in the image buffer 124.

In addition to the above, the inkjet printer 1 according to this embodiment is provided with a detecting section 80 and an A/D converting section 88 as the configuration of a liquid-ejection testing device 60. The liquid-ejection testing device 60 is a device for testing whether or not ink is properly ejected from each nozzle provided at the head 21. More detailed description of the liquid-ejection testing device 60 is given later.

<Head>

Figure 5:
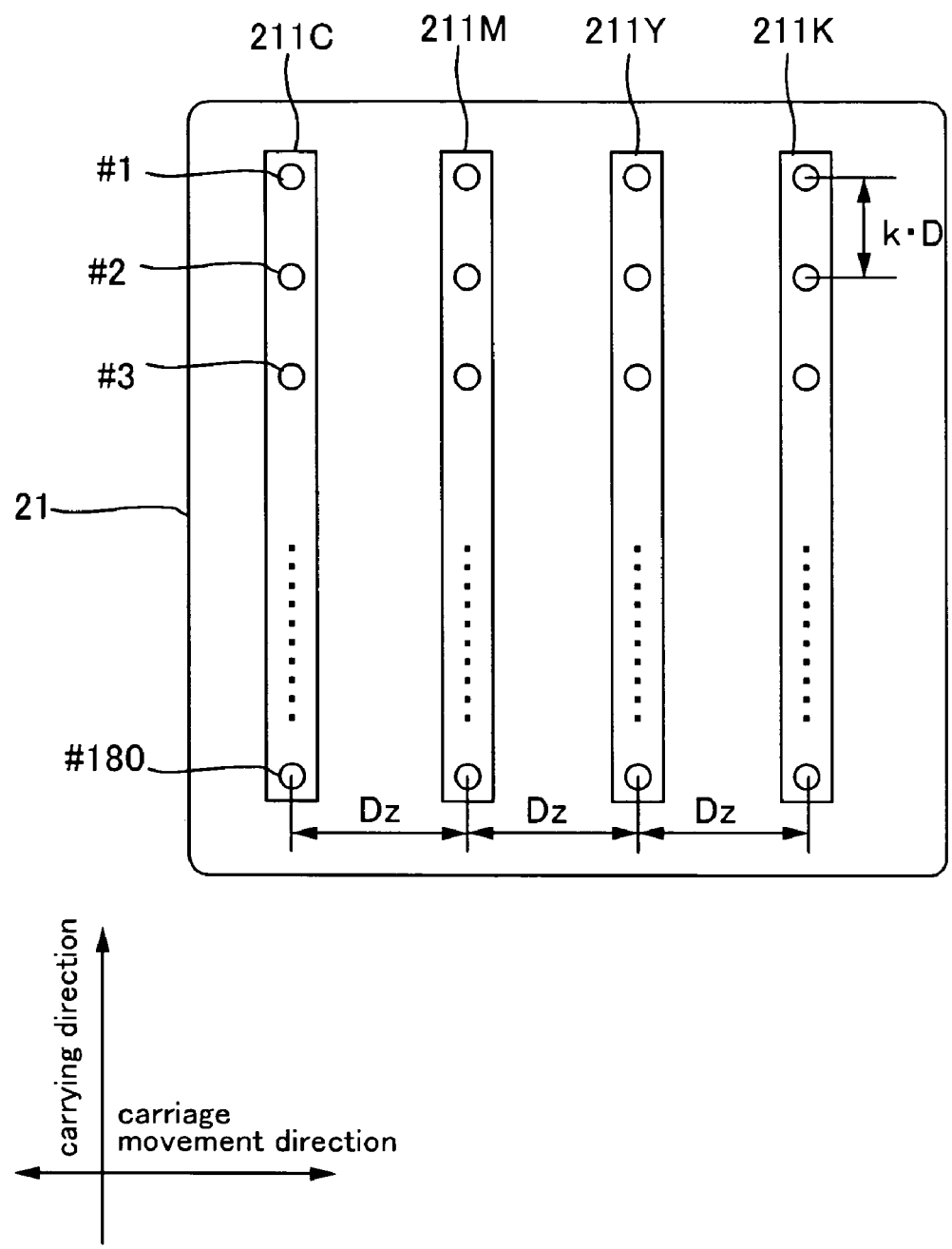
FIG. 5 is an explanatory diagram showing the arrangement of nozzles of a head.

FIG. 5 is a diagram showing the arrangement of the ink nozzles provided on the bottom face portion of the head 21. As shown in FIG. 5, the bottom face portion of the head 21 is provided with nozzle rows constituted by a plurality of nozzles #1 to #180 for each of the colors yellow (Y), magenta (M), cyan (C), and black (K), that is, a cyan nozzle row 211C, a magenta nozzle row 211M, a yellow nozzle row 211Y, and a black nozzle row 211K. It should be noted that each of the cyan nozzle row 211C, the magenta nozzle row 211M, the yellow nozzle row 211Y, and the black nozzle row 211K corresponds to "liquid ejecting section".

The nozzles #1 to #180 (corresponding to "liquid ejecting nozzles") in each of the nozzle rows 211C, 211M, 211Y, and 211K are arranged in one straight line with a spacing therebetween in a predetermined direction (carrying direction of the medium S in this embodiment). Each spacing between the nozzles #1 to #180 (nozzle spacing) is set to "k·D". Here, D is the minimum dot pitch in the carrying direction (that is, the spacing at the highest resolution of dots formed on the medium S). Also, k is an integer of 1 or larger. For example, if the nozzle pitch is 120 dpi ($\frac{1}{120}$ inch), and the dot pitch in the carrying direction is 360 dpi ($\frac{1}{360}$), then k=3.

The nozzle rows 211C, 211M, 211Y, and 211K are arranged in parallel to each other with a predetermined spacing Dz therebetween in the movement direction (scanning direction) of the head 21. The nozzles #1 to #180 of each of the nozzle rows 211C, 211M, 211Y, and 211K are arranged in a straight line in a predetermined direction. In this embodiment, when the head 20 is properly disposed, the nozzles #1 to #180 of each of the nozzle rows 211C, 211M, 211Y, and 211K are arranged in the carrying direction of the medium S. The nozzles #1 to #180 of each of the nozzle rows 211C, 211M, 211Y, and 211K are provided with piezo elements (not shown) as drive elements for ejecting ink droplets.

When a voltage of a predetermined duration is applied between electrodes provided at both ends of the piezo element, the piezo element is expanded for the duration of voltage application and deforms a lateral wall of the ink channel. Accordingly, the volume of the ink channel is constricted according to the expansion and constriction of the piezo element, and ink corresponding to this amount of constriction becomes an ink droplet, which is ejected from the corresponding nozzles #1 to #180 of the color nozzle rows 211C, 211M, 211Y, and 211K.

<Drive Circuit>

Figure 6:
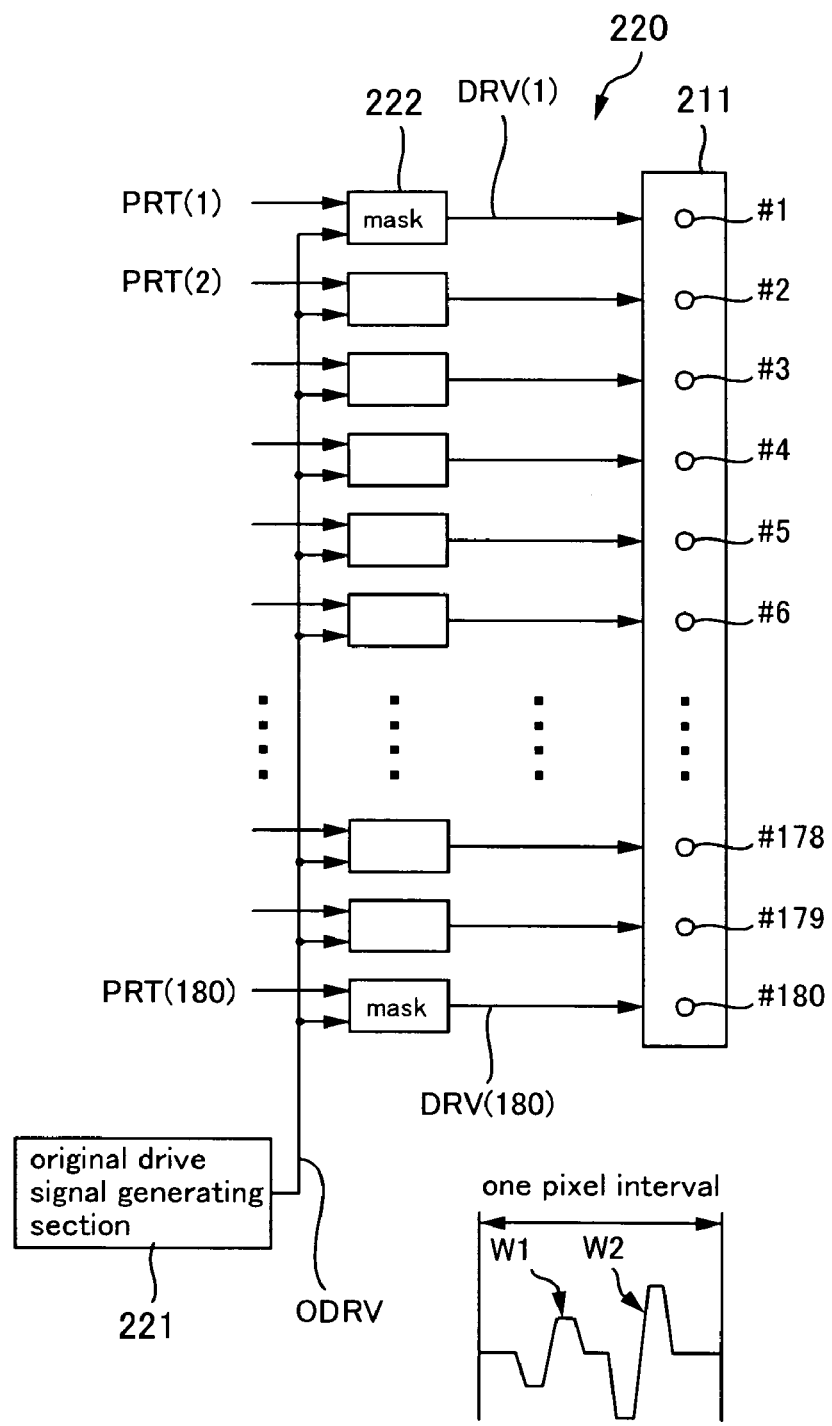
FIG. 6 is a diagram illustrating an example of a drive circuit of the head.

FIG. 6 shows a drive circuit 220 of the nozzles #1 to #180. As shown in FIG. 6, the drive circuit 220 is provided with an original drive signal generating section 221 and a plurality of mask circuits 222. The original drive signal generating section 221 generates an original drive signal ODRV that is commonly used by the nozzles #1 to #180. As shown in a lower portion of FIG. 6, the original drive signal ODRV is a signal that includes two pulses, a first pulse W1 and a second pulse W2 in a main-scanning period for one pixel (within a time during which the carriage 41 passes through the spacing of one pixel). The original drive signal ODRV generated at the original drive signal generating section 221 is output to the mask circuits 222.

The mask circuits 222 are provided in correspondence with the plurality of piezo elements for driving the nozzles #1 to #180 of the head 21. The mask circuits 222 receive the original drive signal ODRV from the original drive signal generating section 221 and also receive print signal PRT(i). The print signal PRT(i) is pixel data corresponding to a pixel, and is a binary signal having 2-bit information corresponding to one pixel. The bits respectively correspond to the first pulse W1 and the second pulse W2. The mask circuits 222 are gates for blocking the original drive signal ODRV or letting it pass through depending on the level of the print signal PRT(i). More specifically, when the print signal PRT(i) is at a level "0", the pulse of the original drive signal ODRV is blocked, but when the print signal PRT(i) is at a level "1", the pulse corresponding to the original drive signal ODRV is led to pass through as it is and is output as a drive signal DRV toward the piezo elements of the nozzles #1 to #180. The piezo elements of the nozzles #1 to #180 are driven based on the drive signal DRV from the mask circuits 222 and eject ink.

<Signal Waveforms>

Figure 7:
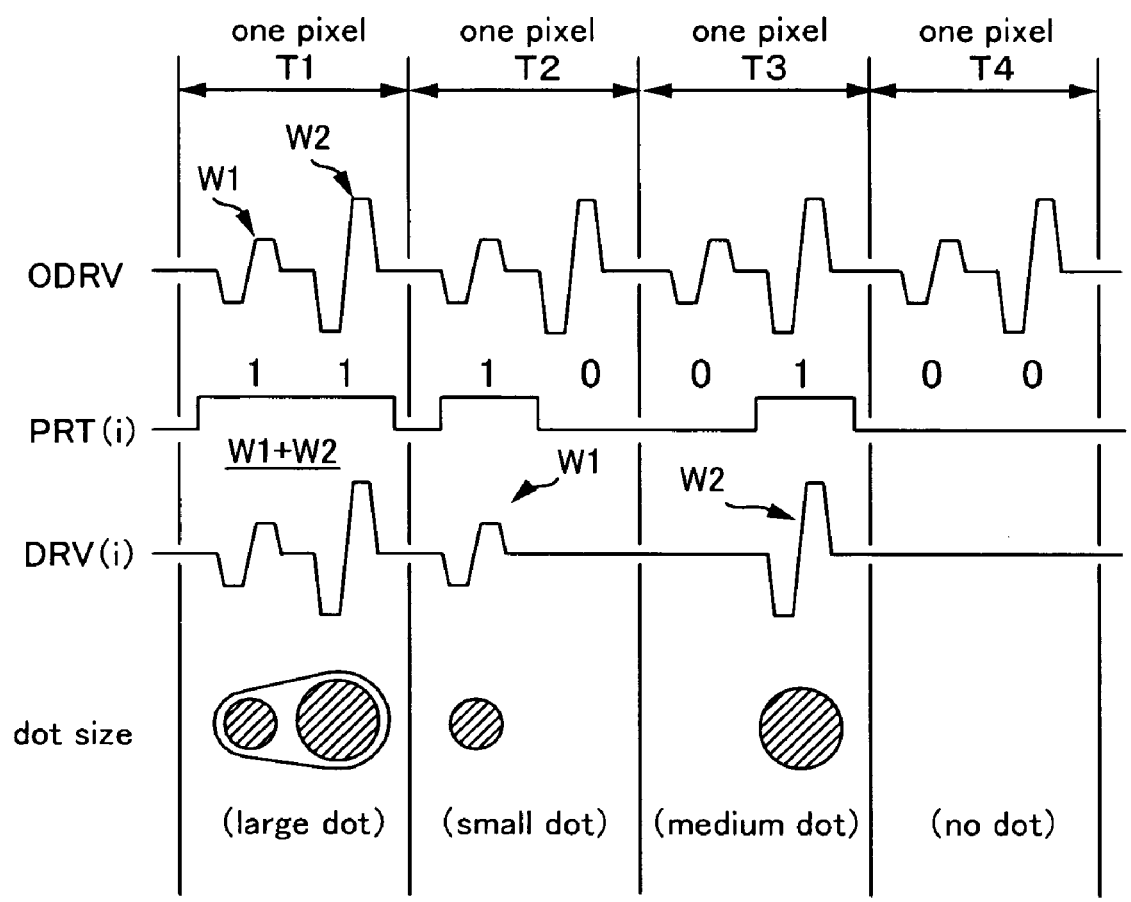
FIG. 7 is a timing chart of signals.

FIG. 7 is a timing chart of the original drive signal ODRV, the print signal PRT(i), and the drive signal DRV(i) indicating the operation of the original drive signal generating section 221. As shown in FIG. 7, the original drive signal ODRV generates the first pulse W1 and the second pulse W2 in this order during each pixel interval T1, T2, T3, and T4. It should be noted that "pixel interval" has the same meaning as the movement interval of the carriage 41 for a one-pixel amount.

Herein, when the print signal PRT(i) corresponds to 2-bit pixel data "10", then only the first pulse W1 is output in the first half of one pixel interval. Accordingly, a small ink droplet is ejected from the nozzles #1 to #180, and a dot of a small size (small dot) is formed on the medium S. Furthermore, when the print signal PRT(i) corresponds to 2-bit pixel data "01", then only the second pulse W2 is output in the second half of one pixel interval. Accordingly an ink droplet of a medium size is ejected from the nozzles #1 to #180, and a dot of a medium size (medium dot) is formed on the medium S. Furthermore, when the print signal PRT(i) corresponds to 2-bit pixel data "11", then the first pulse W1 and the second pulse W2 are output during one pixel interval. Accordingly an ink droplet of a large size is ejected from the nozzles #1 to #180, and a dot of a large size (large dot) is formed on the medium S. As described above, the drive signal DRV(i) in one pixel interval is shaped such that it has three different waveforms corresponding to three different values of the print signal PRT(i), and based on these signals, the head 21 can form dots of three sizes and can adjust the amount of ink ejected during a pixel interval. Furthermore, if the print signal PRT(i) corresponds to 2-bit pixel data "00" as in the pixel interval T4, then no ink droplet is ejected from the nozzles #1 to #180, and no dot is formed on the medium S.

In the inkjet printer 1 according to this embodiment, the drive circuits 220 of the nozzles #1 to #180 are arranged separately for each of the nozzle rows 211C, 211M, 211Y, and 211K, that is, for each of the colors yellow (Y), magenta (M), cyan (C), and black (K), such that piezo elements are driven separately for each of the nozzles #1 to #180 of the nozzle rows 211C, 211M, 211Y, and 211K.

===Printing Operation===

Figure 8:
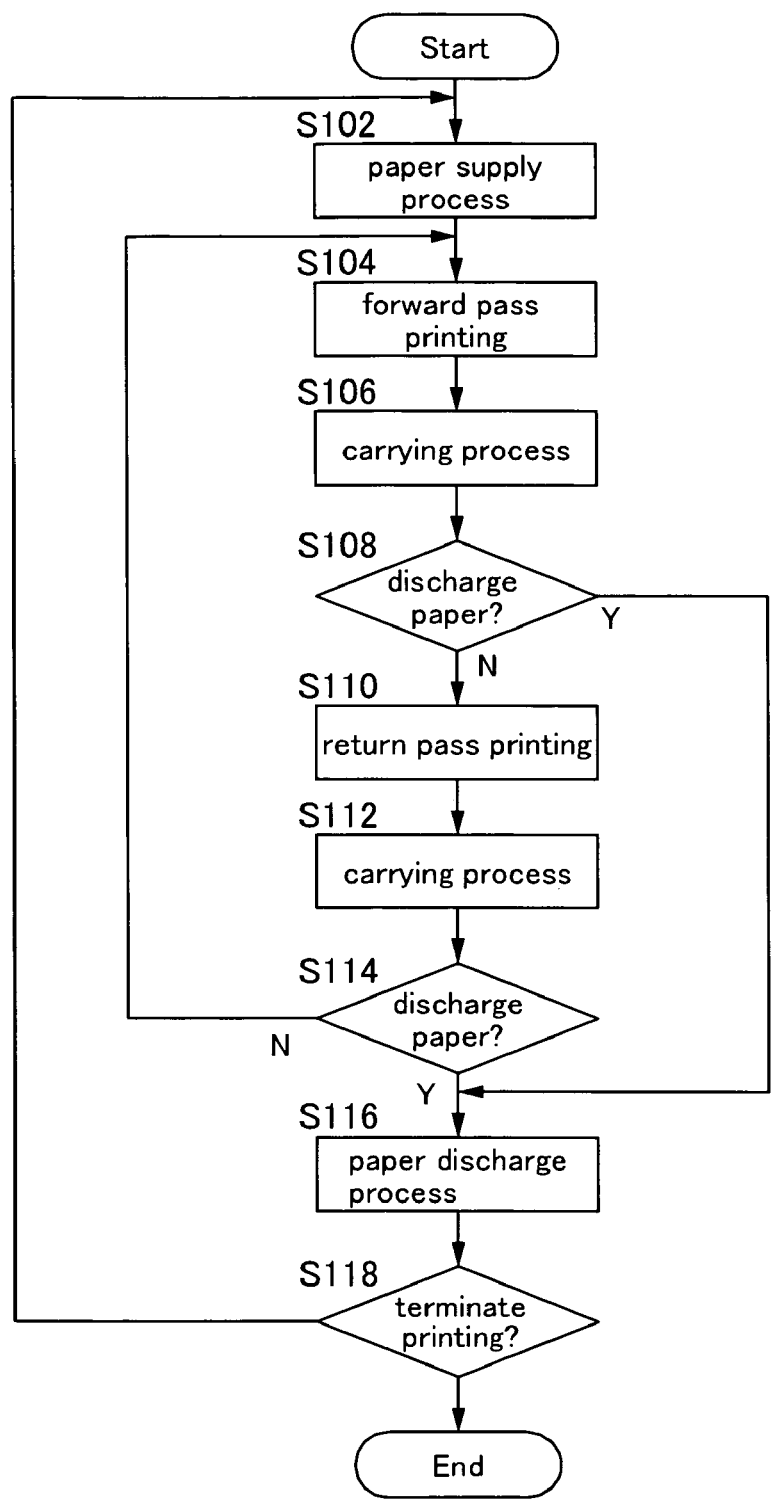
FIG. 8 is a flowchart illustrating an example of a printing process.

The following is a description concerning a printing operation of the above-described inkjet printer 1. Here, an example of "bidirectional printing" is explained. FIG. 8 is a flowchart showing an example of a processing procedure of the printing operation of the inkjet printer 1. The processes described below are each performed when the controller 126 reads out programs from the main memory 127 and controls each of the carriage motor controller 128, the carry controller 130, and the head drive section 132, for example, in accordance with the programs.

When the controller 126 receives print data from the computer 140, in order to carry out printing in accordance with the print data, first, a paper supply process is performed (S102). In the paper supply process, a medium S to be printed is supplied into the inkjet printer 1 and carried to a print starting position (also referred to as "print start position"). The controller 126 rotates the paper supply roller 13 to send the medium S to be printed up to the carry roller 17A. The controller 126 rotates the carry roller 17A to position the medium S that has been sent from the paper supply roller 13 at the print starting position (upstream on the platen 14).

Next, the controller 126 performs a printing process in which the medium S is printed while moving the carriage 41 relative to the medium S by driving the carriage motor 42 via the carriage motor controller 128. Here, first, forward pass printing in which ink is ejected from the head 21 while moving the carriage 41 in one direction along the guide rail 46 is performed (S104). The controller 126 moves the carriage 41 by driving the carriage motor 42, and ejects ink by driving the head 21 in accordance with the print data. The ink ejected from the head 21 reaches the medium S, forming dots.

After printing has been carried out in this manner, the controller 126 performs a carrying process for carrying the medium S only by a predetermined amount (S106). Herein, the controller 126 rotates the carry roller 17A by driving the carry motor 15 via the carry controller 130, and carries the medium S only by a predetermined amount in the carrying direction relative to the head 21. With this carrying process, the head 21 can print onto a region that is different from the region printed on before.

After the carrying process has been performed in this manner, the controller 126 performs a paper discharge determination in which it is determined whether or not to discharge the paper (S108). Herein, the controller 126 performs a paper discharge process if there is no more data to be printed onto the medium S that is currently being printed (S116). On the other hand, if there is data left to be printed onto the medium S that is currently being printed, then the controller 126 performs return pass printing without performing a paper discharge process (S110). In this return pass printing, printing is carried out while moving the carriage 41 along the guide rail 46 in the opposite direction to the previous forward pass printing. Also here, the controller 126 moves the carriage 41 by rotatively driving the carriage motor 42 in the opposite direction as before via the carriage motor controller 128, ejects ink by driving the head 21 based on the print data, and carries out printing.

After return pass printing has been performed, a carrying process is performed (S112), and then a paper discharge determination is performed (S114). Here, if there is data left to be printed onto the medium S that is currently being printed, then no paper discharge process is performed, and the procedure returns to step S104, where forward pass printing is carried out again (S104). On the other hand, a paper discharge process is performed if there is no more data to be printed onto the medium S that is currently being printed (S116).

After the paper discharge process has been performed, a print termination determination is performed in which it is determined whether or not to terminate printing (S118). Here, based on the print data from the computer 140, it is checked whether or not there is a further medium S to be printed left. If there is a further medium S to be printed left, then the procedure returns to step S102, where another paper supply process is performed, and printing is started. On the other hand, if no further medium S to be printed is left, then the printing process is terminated.

===Liquid-ejection Testing Device===

An embodiment of a liquid-ejection testing device according to the present invention is described. The following is a description concerning an example in which the liquid-ejection testing device according to the present invention is mounted on the above-described inkjet printer 1 (liquid ejecting apparatus, printing apparatus).

<Outline of Testing Device>

Figure 9:
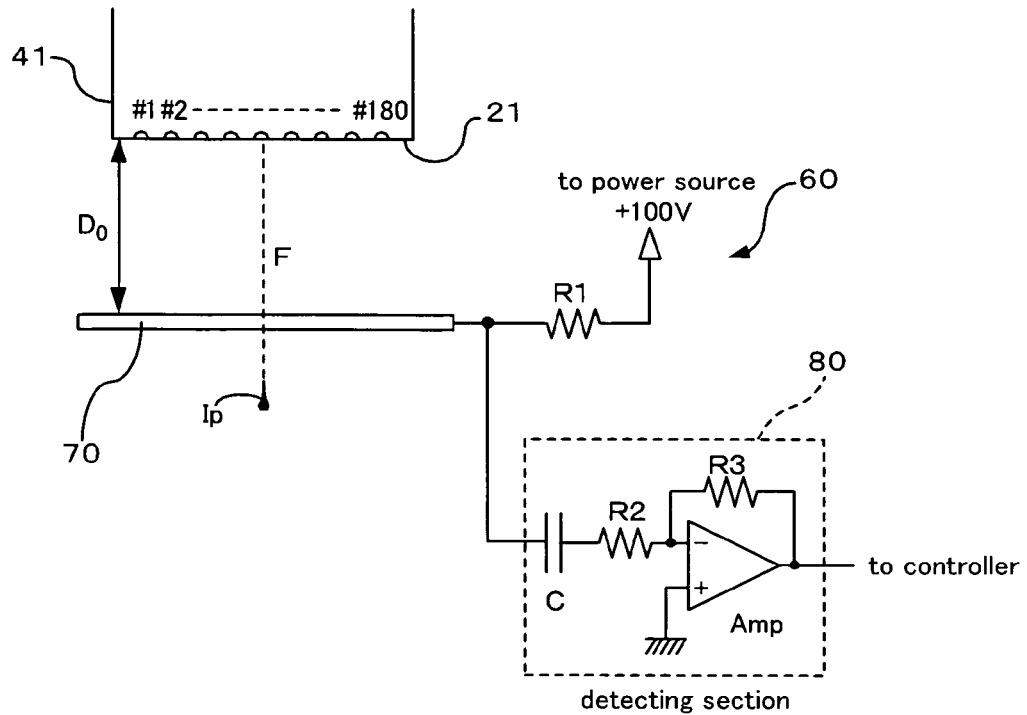
FIG. 9 is an explanatory diagram illustrating a liquid-ejection testing device.
Figure 10:
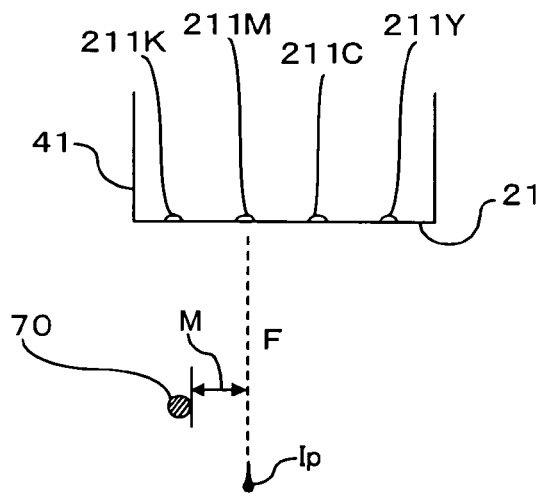
FIG. 10 is an explanatory diagram illustrating the testing principle of the liquid-ejection testing device.

FIGS. 9 and 10 schematically illustrate the liquid-ejection testing device 60 mounted on the inkjet printer 1 according to this embodiment and the testing method thereof. FIG. 9 is an explanatory diagram illustrating the configuration of the liquid-ejection testing device 60. FIG. 10 is an explanatory diagram for illustrating the testing principle of the liquid-ejection testing device 60.

As shown in FIG. 9, the liquid-ejection testing device 60 is provided with a detection member 70 disposed at a position that can be opposed to the head 21, and a detecting section 80 connected to this detection member 70. The detection member 70 is made of a conductive wire material such as metal, and is disposed in parallel to the head 21 in such a manner that the detection member 70 is stretched in tension. The detection member 70 is disposed such that it can be opposed to the head 21 in a non-contact state, with a spacing D0 from the head 21, when the carriage 41 moves. The spacing D0 between the head 21 and the detection member 70 is set to 1 mm, for example.

Furthermore, a power source (not shown) is connected via a protective resistance R1 to the detection member 70. A high voltage such as +100 V (volt) is applied from the power source to the detection member 70.

On the other hand, the detecting section 80 detects an electric current generated at the detection member 70. In this embodiment, the detecting section 80 is constituted by a detection circuit provided with a capacitor C, an input resistance R2, a feedback resistance R3, and an operational amplifier Amp. When a change in the electric current is generated at the detection member 70, the capacitor C fulfils the role of inputting the change in the electric current as an electric signal via the input resistance R2 to the operational amplifier Amp. Furthermore, the operational amplifier Amp fulfils the role as an amplifier circuit in which the signal that has been input via the capacitor C is amplified and output. The output signal from the operational amplifier Amp is A/D converted from an analog signal to a digital signal by the A/D converting section 88 (see FIG. 4), and is sent to the controller 126 in an appropriate state such as digital data.

When the ejection test is actually performed, an operation is performed in which ink is separately ejected from each of the nozzles #1 to #180 of the head 21 toward the detection member 70 or its vicinity. FIG. 10 illustrates how ink is ejected from a particular nozzle of the head 21 toward the vicinity of the detection member 70. Here, an ink droplet Ip of a one-time amount, that is, a one-droplet amount, is ejected from each of the nozzles #1 to #180 of the head 21.

At that time, a very high voltage such as 100 V (volt) is applied to the detection member 70 because of the voltage supplied from the power source. Thus, a very strong electric field is formed between the head 21 and the detection member 70. In such a state, when the ink droplet Ip is ejected from the nozzles #1 to #180, the ejected ink droplet Ip is charged.

The charged ink droplet Ip ejected from the nozzles #1 to #180 passes through the vicinity of the detection member 70. When the charged ink droplet Ip passes through the vicinity of the detection member 70, an induced current is generated at the detection member 70. When the charged ink droplet Ip approaches the detection member 70, an induced current is generated in a predetermined direction at the detection member 70. It should be noted that the induced current thus generated is attributable to electrostatic induction accompanying the approach of the charged ink droplet Ip.

At that time, at the detection member 70, the induced current of a magnitude corresponding to a distance M between the detection member 70 and a flight path F of the ink droplet Ip is generated. More specifically, if the flight path F of the ink droplet Ip is close to the detection member 70, then the magnitude of the induced current generated at the detection member 70 becomes large. Furthermore, if the flight path F of the ink droplet Ip is away from the detection member 70, then the magnitude of the induced current generated at the detection member 70 becomes small.

When an induced current corresponding to the distance between the detection member 70 and the flight path F of the ink droplet Ip is generated at the detection member 70 in this manner, an electric current that is input to the detecting section 80 changes, and this change in the electric current is input as an electric signal via the input resistance R2 to the operational amplifier Amp. Then, the signal that has been input to the operational amplifier Amp is amplified and is output as a detection signal toward the controller 126, for example. Thus, when an induced current is generated at the detection member 70, it is detected by the detecting section 80, and the detection signal is converted from an analog signal to, for example, digital data through the A/D converting section 88 (see FIG. 4), and is output toward the controller 126.

On the other hand, when no ink droplet Ip is ejected from the nozzles #1 to #180, no charged ink droplet Ip passes through the vicinity of the detection member 70, and thus a sufficient induced current is not generated at the detection member 70. Thus, a sufficient detection signal is not output at the detecting section 80.

The controller 126 acquires the magnitude of the induced current that has been generated at the detection member 70 based on the signal level of the detection signal that has been output from the detecting section 80, and judges whether or not the ink droplet Ip is ejected from the nozzles #1 to #180, based on the magnitude of the induced current. Furthermore, the controller 126 judges whether or not the distance M between the flight path F of the ink droplet Ip and the detection member 70 is within a predetermined distance, based on the magnitude of the induced current that has been generated at the detection member 70. Thus, the controller 126 judges whether or not the ejection direction of the ink droplet Ip from the nozzles #1 to #180 is proper.

In other words, if the magnitude of the induced current that has been generated at the detection member 70 is within a predetermined range, then the controller 126 determines that the distance M between the flight path F of the ink droplet Ip and the detection member 70 is within a predetermined distance, and judges that the ejection direction of the ink droplet Ip from the nozzles #1 to #180 is proper. Furthermore, if the magnitude of the induced current that has been generated at the detection member 70 is out of the predetermined range, then the controller 126 determines that the distance M between the flight path F of the ink droplet Ip and the detection member 70 is out of the predetermined distance, and judges that the ejection direction of the ink droplet Ip from the nozzles #1 to #180 is not proper. It should be noted that in this embodiment, the controller 126 corresponds to "judging section" that judges whether or not ink is properly ejected.

In this manner, the controller 126 judges whether or not the ink droplet Ip is properly ejected from the nozzles #1 to #180, for example, by judging whether or not the ink droplet Ip is ejected or by judging whether or not the ejection direction of the ink droplet Ip is proper. In addition to the above, the controller 126 may judge whether or not the ejecting speed of the ink droplet Ip from the nozzles #1 to

180 is proper by acquiring the timing at which an induced current is generated at the detection member 70, for example.

It is preferable that the size of the ink droplet Ip ejected from the nozzles #1 to #180 in the ejection test is as large as possible. In other words, in the inkjet printer 1 according to this embodiment, it is preferable that the dot size is set to a size substantially equal to the largest dot size, for example, the ink droplet Ip that is ejected to form a large dot (pixel data "11") on the medium S. The reason for this is that the charge amount that the ink droplet Ip ejected from the nozzles #1 to #180 is charged becomes larger as the size of the ink droplet Ip ejected from the nozzles #1 to #180 becomes larger. When the charge amount of the ink droplet Ip becomes larger in this manner, an induced current can be generated more easily at the detection member 70. Thus, an induced current at the detection member 70 can be detected more easily at the detecting section 80.

It goes without saying that it is not necessarily required to set the size of the ink droplet Ip ejected in the ejection test to the size applied when a dot of the largest size (large dot, for example) is formed. An ink droplet Ip of a large size may be ejected specially only for the ejection test, or an ink droplet Ip of a small size may be ejected.

Furthermore, it is not necessarily required that the ink droplet Ip ejected from the nozzles #1 to #180 is ejected toward the vicinity of the detection member 70. The ink droplet Ip may be ejected so as to be brought into contact with the detection member 70. Also in this case, an induced current is generated at the detection member 70 because the ink droplet Ip approaches the detection member 70, and thus it is possible to check whether or not the ink droplet Ip is ejected.

Furthermore, the number of the ink droplet Ip ejected from the nozzles #1 to #180 is not necessarily limited to one. In other words, ink droplets Ip may be successively ejected a plurality of times from the nozzles #1 to #180. When the ink droplets Ip are successively ejected a plurality of times in this manner, the number of the ink droplets Ip that pass through the vicinity of the detection member 70 increases, and thus an induced current can be generated more easily at the detection member 70. Thus, an induced current can be detected more easily at the detecting section 80.

===Actual Detection Waveforms===

Figure 11:
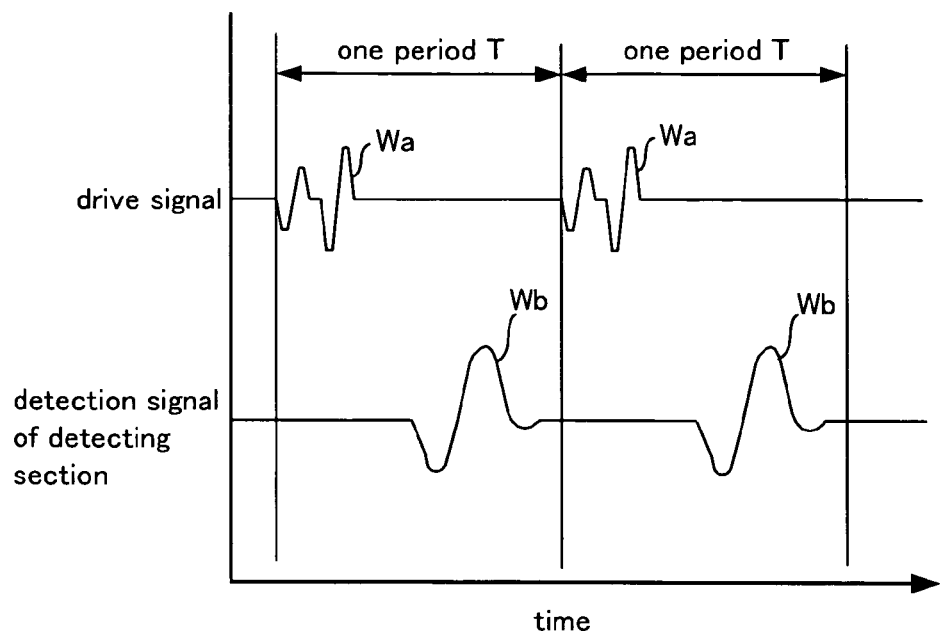
FIG. 11 is an explanatory diagram of a drive signal for letting ink be ejected and a detection signal of a detecting section.

FIG. 11 shows the respective waveforms of a drive signal that is output toward the piezo elements arranged in correspondence with the nozzles #1 to #180 in order to let ink be ejected in the ejection test and a detection signal from the detecting section 80. The upper waveform in FIG. 11 shows the waveform of the drive signal, and the lower waveform in FIG. 11 shows the waveform of the detection signal of the detecting section 80. When the ejection test is to be performed on a particular nozzle, as shown in FIG. 11, a drive pulse Wa for letting an ink droplet of a one-time amount, that is, a one-droplet amount be ejected is input as a drive signal to the piezo element disposed at the nozzle that is to be tested.

On one hand, when ink is properly ejected from the nozzle that is to be tested, based on the drive signal, an induced current is generated at the detection member 70 with the ink droplet Ip ejected from the nozzle that is to be tested. When the induced current is detected by the detecting section 80, a pulse Wb in the waveform that oscillates up and down as shown in FIG. 11 is output as a detection signal from the detecting section 80. Since it takes time from when the ink droplet Ip is ejected from the nozzle that is to be tested until an induced current is generated, and since there is a slight time lag until when the induced current that is generated is detected by the detecting section 80 and output, the rising edge of the pulse of the detection signal that is output from the detecting section 80 is delayed compared to the drive pulse of the drive signal.

On the other hand, when ink is not properly ejected from the nozzles #1 to #180, no induced current is generated at the detection member 70. Thus, the pulse Wb in the waveform as shown in FIG. 11 does not appear clearly in the detection signal of the detecting section 80.

It should be noted that the ejection test can be performed successively on a plurality of nozzles such as one row of the nozzle rows, that is, 180 nozzles in the nozzles #1 to #180 at one time. At that time, as the drive signal, the drive pulse for letting the test-target ink droplet Ip of a one-time amount (one-droplet amount) be ejected is repeatedly output at a predetermined period T as shown in FIG. 11. Furthermore, when ink is properly ejected from the nozzles #1 to #180 in response to the drive signal, pulses Wb are formed at the predetermined period T in the detection signal of the detecting section 80, as shown in FIG. 11. Herein, it is preferable to set the predetermined period T as appropriate using, as a reference, the time from when the drive pulse Wa is output to the nozzles #1 to #180 that are to be tested to when the pulse Wb appears in the detection signal of the detecting section 80. The test can be performed separately for each of the nozzles #1 to #180 by checking the detection signal separately from the detecting section 80 in every period T.

===Judgment of Whether or Not Ejection is Performed===

Figure 12:
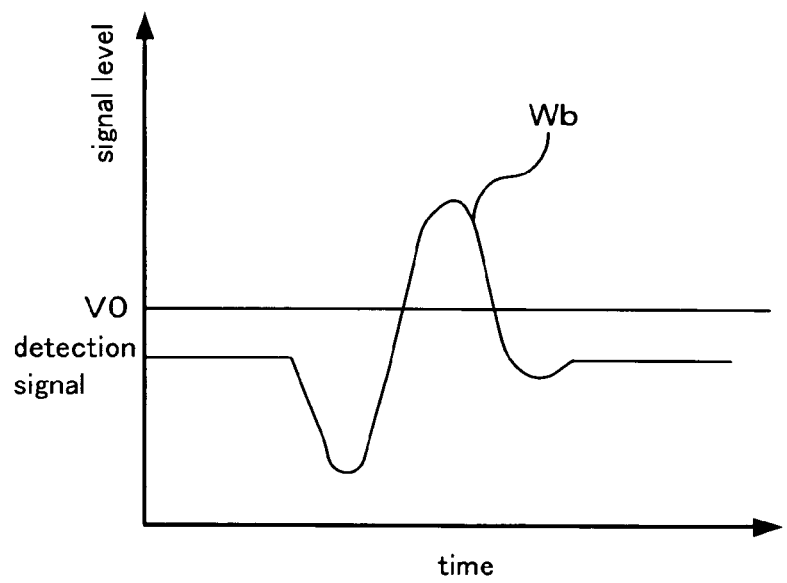
FIG. 12 is an explanatory diagram illustrating an example of a method for judging whether or not ink is ejected.

FIG. 12 illustrates an example of a method for judging with the controller 126 whether or not the ink droplet Ip is ejected from the nozzles #1 to #180. Herein, the controller 126 compares the magnitude of the induced current generated at the detection member 70, that is, the signal level of the detection signal output from the detecting section 80 with a predetermined reference value V0 to check whether or not the signal level of the detection signal output from the detecting section 80 has reached the predetermined reference value V0. The signal level of the detection signal output from the detecting section 80 and the predetermined reference value V0 are compared with each other sequentially by the controller 126.

When the ink droplet Ip is ejected from the nozzles #1 to #180 and an induced current is generated at the detection member 70, the pulse Wb is generated in the detection signal from the detecting section 80 as shown in FIG. 12, and the signal level of the detection signal increases to reach the predetermined reference value V0. When the signal level of the detection signal has reached the predetermined reference value V0 in this manner, the controller 126 determines that an induced current of a sufficient magnitude is generated at the detection member 70, and judges that ink is ejected from the nozzle.

On the other hand, when no ink droplet Ip is ejected from the nozzles #1 to #180, no induced current is generated at the detection member 70, and thus no pulse Wb is generated in the detection signal from the detecting section 80. Accordingly, the signal level of the detection signal from the detecting section 80 does not increase and does not reach the predetermined reference value V0. Thus, the controller 126 determines that an induced current of a sufficient magnitude is not generated at the detection member 70, and judges that no ink droplet Ip is ejected from the nozzle.

The controller 126 tests whether or not an ink droplet is ejected from each of the nozzles #1 to #180 based on the detection signal output from the detecting section 80 in this manner.

Herein, the predetermined reference value V0 is set to an appropriate value that does not cause an error in the ejection test. Information on the predetermined reference value V0 is stored as data in an appropriate storing section, for example, a memory such as the main memory 127. When comparing the magnitude of the detection signal with the predetermined reference value V0, the controller 126 acquires the information on the predetermined reference value V0 from an appropriate storing section such as the main memory 127.

===Judgment of Ejection Direction===

The following is a description concerning an example of a method for testing whether or not the ejection direction of the ink droplet Ip from the nozzles #1 to #180 is proper. Herein, the judgment of whether or not the ejection direction of the ink droplet Ip is proper is also performed by the controller 126. The controller 126 performs the judgment based on the detection signal output from the detecting section 80.

Figure 13:
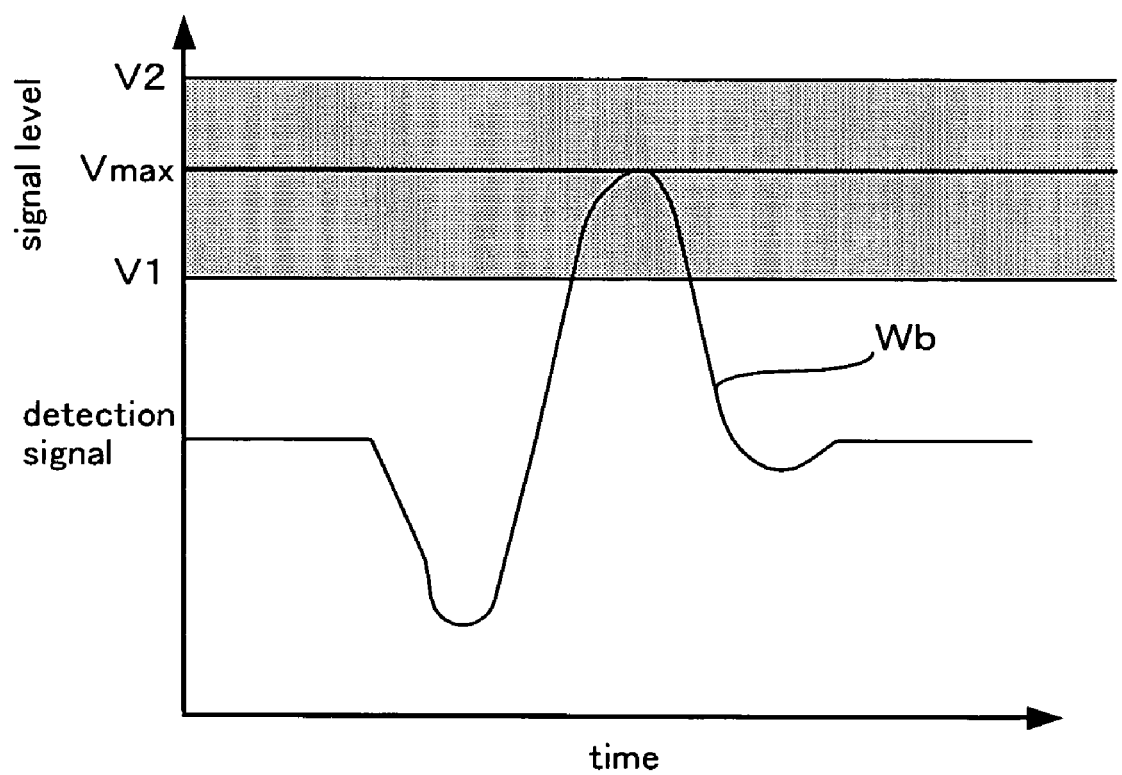
FIG. 13 is an explanatory diagram illustrating an example of a method for judging the ejection direction of ink.

FIG. 13 illustrates an example of the testing method. In this test, a peak value Vmax is acquired from the waveform Vb of the detection signal obtained from the detecting section 80. Then, it is checked whether or not the acquired peak value Vmax is within a predetermined tolerance range. More specifically, since the acquired peak value Vmax changes in accordance with the distance M between the detection member 70 and the flight path F of the ink droplet Ip, the distance M between the detection member 70 and the flight path F of the ink droplet Ip can be obtained by acquiring the peak value Vmax, and thus it is possible to check whether or not the ejection direction of the ink droplet Ip ejected from the nozzles is free of abnormality.

Herein, the predetermined tolerance range is set between a minimum tolerance value V1 and a maximum tolerance value V2. The minimum tolerance value V1 is the lower limit value of the peak value Vmax, and defines the upper limit of the distance M between the detection member 70 and the flight path F of the ink droplet Ip. Furthermore, the maximum tolerance value V2 is the upper limit value of the peak value Vmax, and defines the lower limit of the distance M between the detection member 70 and the flight path F of the ink droplet Ip. The minimum tolerance value V1 and the maximum tolerance value V2 are set with a predetermined tolerance range with respect to a reference distance between a standard path on which the ink droplet Ip is to originally fly and the detection member 70. Thus, when the flight path F of the ink droplet Ip is greatly apart from the standard path and is too close to the detection member 70, the peak value Vmax of the detection signal from the detecting section 80 is higher than the maximum tolerance value V2, and thus it can be judged that the ejection direction of the ink droplet Ip is not proper. Furthermore, when the flight path F of the ink droplet Ip is too away from the detection member 70, the peak value Vmax of the detection signal from the detecting section 80 is lower than the minimum tolerance value V1, and thus it can be judged that the ejection direction of the ink droplet Ip is not proper.

Figure 14A:
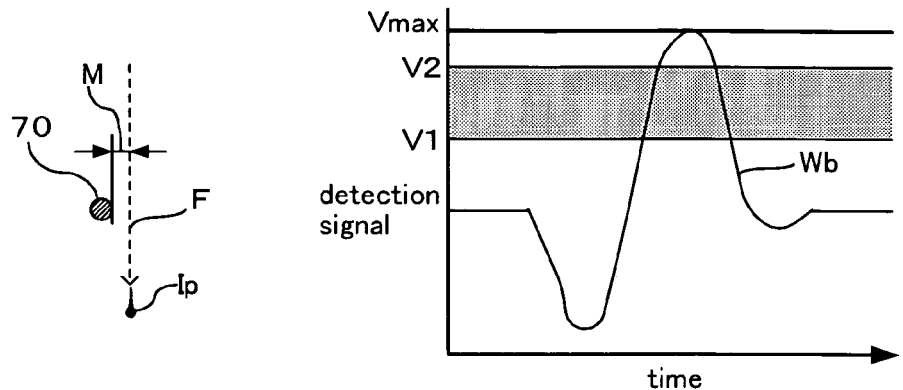
FIG. 14A is a diagram illustrating a case in which a flight path of an ink droplet is too close to a detection member.
Figure 14B:
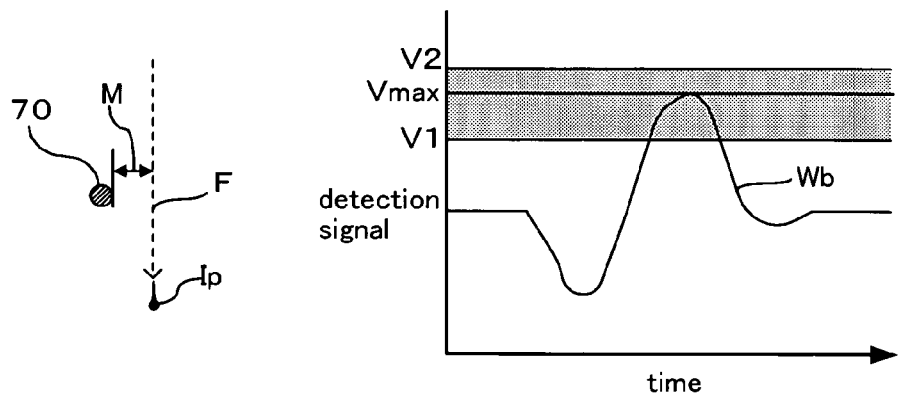
FIG. 14B is a diagram illustrating a case in which a flight path of an ink droplet is within a tolerance range.
Figure 14C:
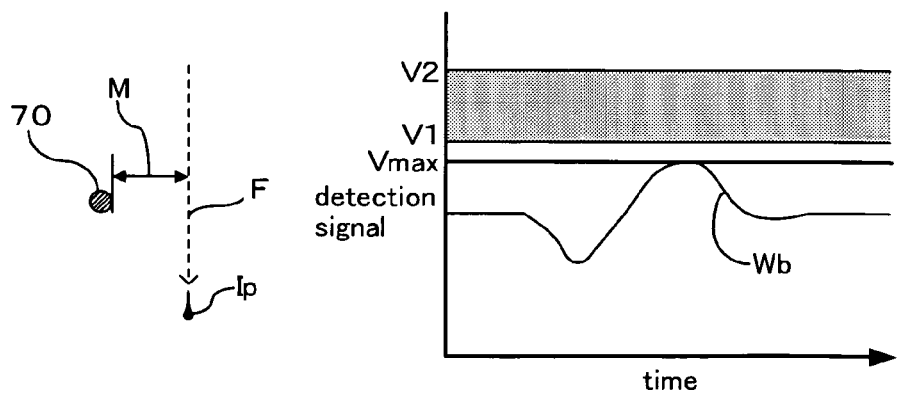
FIG. 14C is a diagram illustrating a case in which a flight path of an ink droplet is too away from the detection member.

FIGS. 14A, 14B, and 14C show the relationship between the distance M between the detection member 70 and the flight path F of the ink droplet Ip, and the waveform of the detection signal from the detecting section 80. FIG. 14A shows a case in which the flight path F of the ink droplet Ip is very close to the detection member 70. FIG. 14B shows a case in which the flight path F of the ink droplet Ip is within the tolerance range. FIG. 14C shows a case in which the flight path F of the ink droplet Ip is too away from the detection member 70.

When the flight path F of the ink droplet Ip is very close to the detection member 70, the peak value Vmax of the signal waveform of the detection signal from the detecting section 80 is higher than the upper limit value of the predetermined tolerance range, that is, the maximum tolerance value V2 as shown in FIG. 14A, and it is judged that the ejection direction of the ink droplet Ip from the nozzle is not proper.

Furthermore, when the flight path F of the ink droplet Ip is within the tolerance range, the peak value Vmax of the signal waveform of the detection signal from the detecting section 80 is within the predetermined tolerance range, that is, between the minimum tolerance value V1 and the maximum tolerance value V2 as shown in FIG. 14B, and it is judged that the ejection direction of the ink droplet Ip from the nozzle is proper.

On the other hand, when the flight path F of the ink droplet Ip is too away from the detection member 70, the peak value Vmax of the signal waveform of the detection signal from the detecting section 80 is lower than the lower limit value of the predetermined tolerance range, that is, the minimum tolerance value V1 as shown in FIG. 14C, and it is judged that the ejection direction of the ink droplet Ip from the nozzle is not proper.

It should be noted that the minimum tolerance value V1 and the maximum tolerance value V2 for defining the predetermined tolerance range correspond to "reference values". Furthermore, information on the minimum tolerance value V1 and the maximum tolerance value V2 for defining the predetermined tolerance range is stored as data in an appropriate storing section, for example, a memory such as the main memory 127. When comparing the peak value Vmax with the minimum tolerance value V1 or the maximum tolerance value V2, the controller 126 acquires the information on the minimum tolerance value V1 and the maximum tolerance value V2 from an appropriate storing section such as the main memory 127.

In the description above, whether or not the ejection direction of the ink droplet Ip is proper is judged based on the peak value Vmax of the detection signal from the detecting section 80, but the method for judging the ejection direction of the ink droplet Ip is not limited to this manner that is performed based on the peak value Vmax of the signal level of the detection signal from the detecting section 80. The judgment may be performed using, as a reference, any portion of the detection signal from the detecting section 80 as long as the judgment is performed using, as a reference, the magnitude of an induced current generated at the detection member 70.

===Detection Member of the Present Embodiment===

In the inkjet printer 1 according to this embodiment, the detection member 70 has the following configuration in order to efficiently perform the ejection test on the nozzles #1 to #180 of the nozzle rows 211C, 211M, 211Y, and 211K.

<Arrangement Method (Summary)>

Figure 15A:
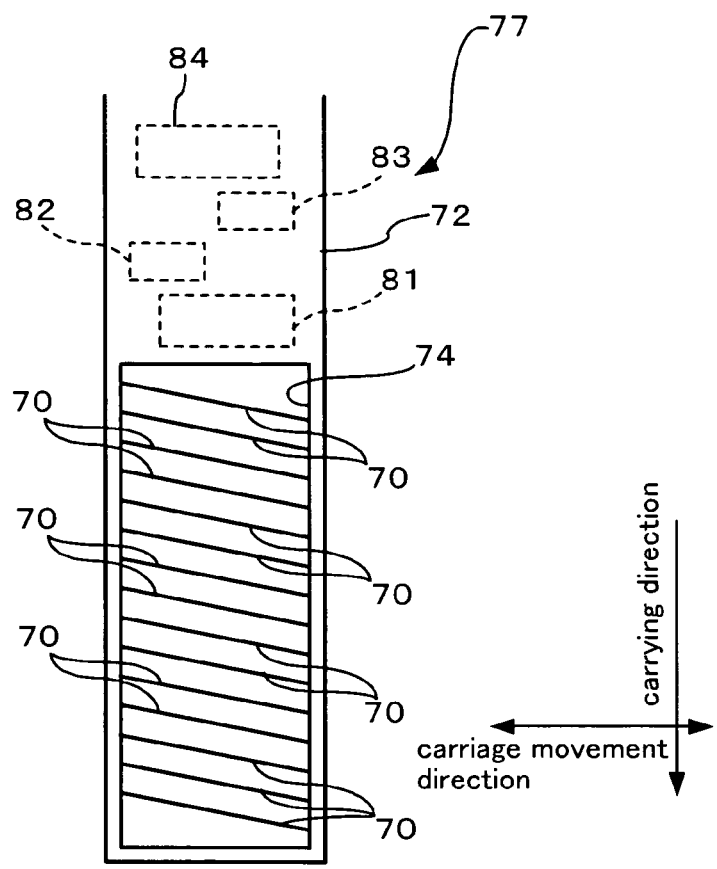
FIG. 15A is a plan view showing the configuration of the detection members according to the embodiment.
Figure 15B:
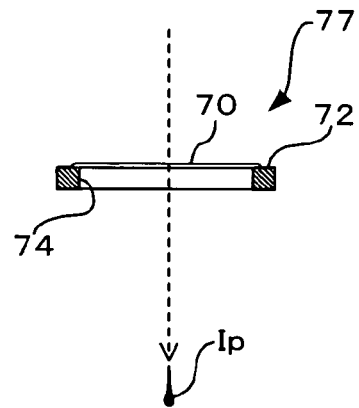
FIG. 15B is a vertical cross-sectional view of the structure in which the detection members are arranged.

FIGS. 15A and 15B show the configuration of the detection member 70 in the liquid-ejection testing device 60 that is mounted on the inkjet printer 1 according to this embodiment. FIG. 15A is a plan view showing the detection members 70. FIG. 15B is a vertical cross-sectional view showing the detection members 70.

As shown in FIG. 15A, the detection member 70 is disposed on a rectangular substrate 72. The substrate 72 is constituted by, for example, a printed wiring board. The detection member 70 spans at an angle over an opening section 74 formed at the front end portion (lower end portion) of the substrate 72 such that the detection member 70 intersects with the movement direction of the carriage 41. A plurality of such detection members 70 are arranged over the opening section 74. The detection members 70 are arranged in parallel to each other with a spacing therebetween in the lengthwise direction of the substrate 72. Herein, the spacings between the detection members 70 are equal to each other. The diameter of the detection members 70 is about 0.2 mm. Both end portions of each of the detection members 70 are fixed on the edge portions of the opening section 74 of the substrate 72, and are arranged in such a manner that the detection member 70 is stretched over the opening section 74 of the substrate 72. As shown in FIG. 15B, the ink droplet Ip ejected from the nozzles #1 to #180 of the head 21 passes by the side of the detection members 70 through the gaps between the detection members 70 to drop downward from the substrate 72.

The reason why the detection members 70 are arranged at an angle with respect to the movement direction of the carriage 41 is to detect misalignment in the carrying direction of the ink droplet Ip ejected from the nozzles #1 to #180. When the ink droplet Ip is shifted in the carrying direction, "white streaks" may be generated in an image to be printed, in the movement direction of the carriage 41. Thus, the image quality of an image to be printed is affected more when the ink droplet Ip ejected from the nozzles #1 to #180 is shifted in the carrying direction than when it is shifted in the movement direction of the carriage 41. Therefore, it is necessary to test misalignment in the carrying direction of the ejected ink droplet Ip in detail.

Furthermore, in this embodiment, circuit elements 81, 82, 83, and 84 constituting, for example, the protective resistance R1, the capacitor C, the input resistance R2, the feedback resistance R3, and the operational amplifier Amp that constitute the detecting section 80 are integrally mounted on the substrate 72 provided with the plurality of detection members 70. Accordingly, the substrate 72 serves as an ejection testing unit 77 on which the detection members 70 and the circuit elements 81, 82, 83, and 84 for performing the ejection test are integrally mounted.

<Configuration of Detection Members>

Figure 16:
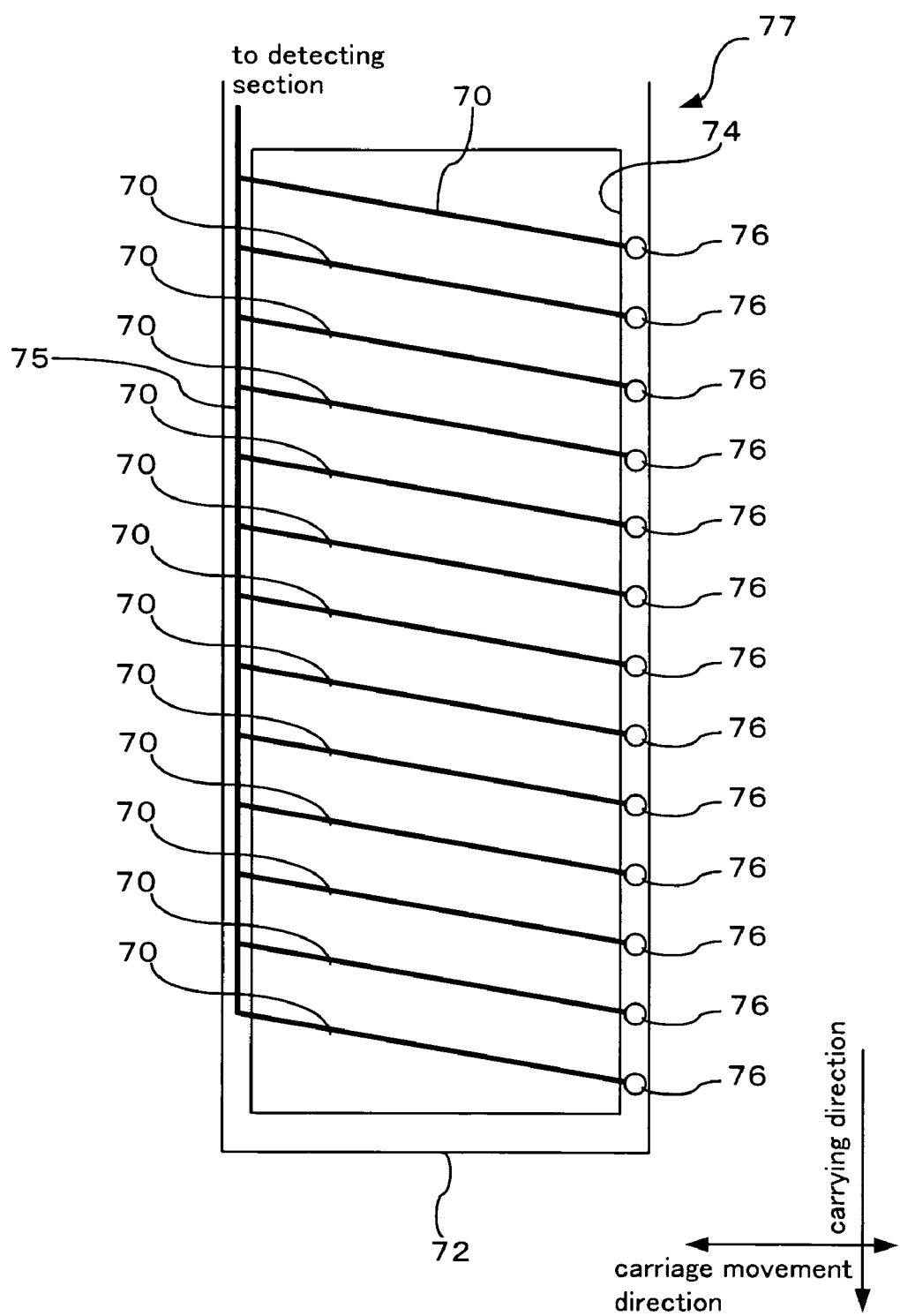
FIG. 16 is a view illustrating the configuration of the detection members according to the embodiment.

FIG. 16 illustrates in detail the circuit configuration of the detection members 70 arranged on the substrate 72. As shown in FIG. 16, the detection members 70 arranged on the substrate 72 are arranged at an angle with an equal spacing therebetween in the lengthwise direction of the substrate 72. One end portions (left end portions in this embodiment) of the detection members 70 are connected to one common line 75 disposed along the edge portion (left edge portion in this embodiment) of the opening section 74 of the substrate 72. The common line 75 is connected to the detecting section 80 that detects an induced current generated at the detection members 70.

On the other hand, unlike the one end portions (left end portions in this embodiment), the other end portions (right end portions in this embodiment) of the detection members 70 are not electrically connected to each other via the common line 75, for example, and each of them is electrically open. The other end portions (right end portions in this embodiment) of the detection members 70 are fixed via respective fixing sections 76 on the edge portion of the opening section 74 of the substrate 72. Accordingly, the plurality of detection members 70 and the common line 75 are configured in the shape of a comb.

In this manner, one end portions (left end portions in this embodiment) of the detection members 70 are connected to the common line 75, and the other end portions (right end portions in this embodiment) of the detection members 70 are not electrically connected to each other and each of them is electrically open, so that when the charged ink droplet Ip passes through the gaps between the detection members 70, it can be detected by the detection members 70. An induced current generated at the detection members 70 by the charged ink droplet Ip passing through is detected via the common line 75 by the detecting section 80.

Furthermore, since the plurality of detection members 70 are connected to each other via the common line 75 so as to be configured in the shape of a comb, the test can be performed on the plurality of nozzles #1 to #180 in a very simple configuration. Especially, even when the length of the detection members 70 is short, it is possible to correspond to the plurality of nozzles #1 to #180, and thus the configuration of the device can be made very compact.

===Position at which Ejection Testing Unit is Disposed===

Figure 17:
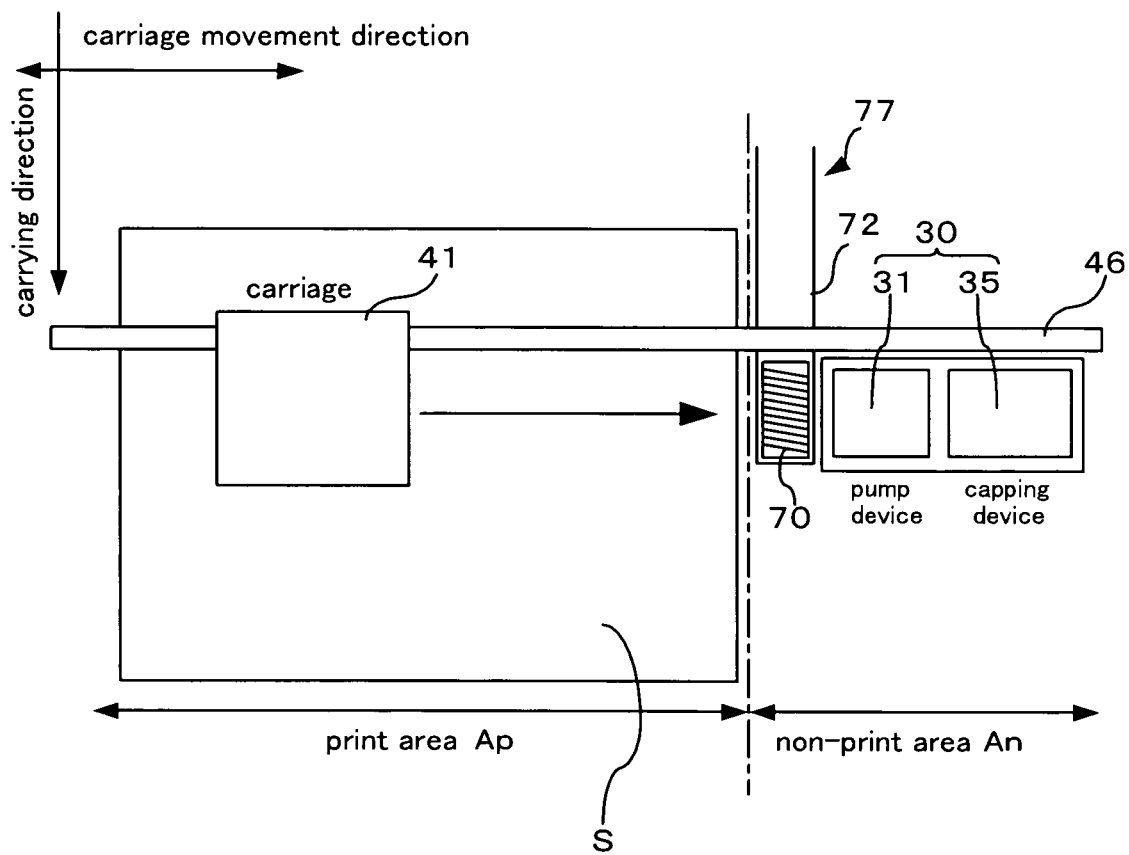
FIG. 17 is a view illustrating an example of the position at which an ejection testing unit according to the embodiment is disposed.

FIG. 17 illustrates in detail the position at which the ejection testing unit 77 according to this embodiment is disposed. As shown in FIG. 17, the ejection testing unit 77 according to this embodiment is disposed in an area An (hereinafter, referred to as "non-print area") that is out of a print area Ap onto which ink is ejected from the nozzles #1 to #180 to carry out printing. The non-print area An is provided with the pump device 31, serving as a cleaning device for the nozzles #1 to #180, for pumping ink from the nozzles #1 to #180 such that clogging in the nozzles is eliminated. Furthermore, the non-print area An is provided with the capping device 35 for capping the nozzles #1 to #180 of the head 21 when printing is not being carried out. The pump device 31 and the capping device 35 constitute a cleaning unit 30. In addition to the above, the cleaning unit 30 may be provided with various devices such as a wiping device for wiping away ink attached more than necessary from the opening sections of the nozzles #1 to #180. The ejection testing unit 77 according to this embodiment is disposed adjacent to the pump device 31 and the capping device 35.

In this embodiment, the ejection testing unit 77 is disposed at the position that is close to the print area Ap, in the non-print area An, that is, between the print area Ap and the cleaning unit 30, as shown in FIG. 17. Accordingly, when the carriage 41 moves from the print area Ap to the non-print area An, it passes above the detection members 70 without fail. This makes it possible to perform the ejection test of ink during any non-printing time in which the carriage 41 moves to the non-print area An.

===Positional Relationship between Ejection Testing Unit and Nozzle Rows <No. 1: First Embodiment>===

Figure 18:
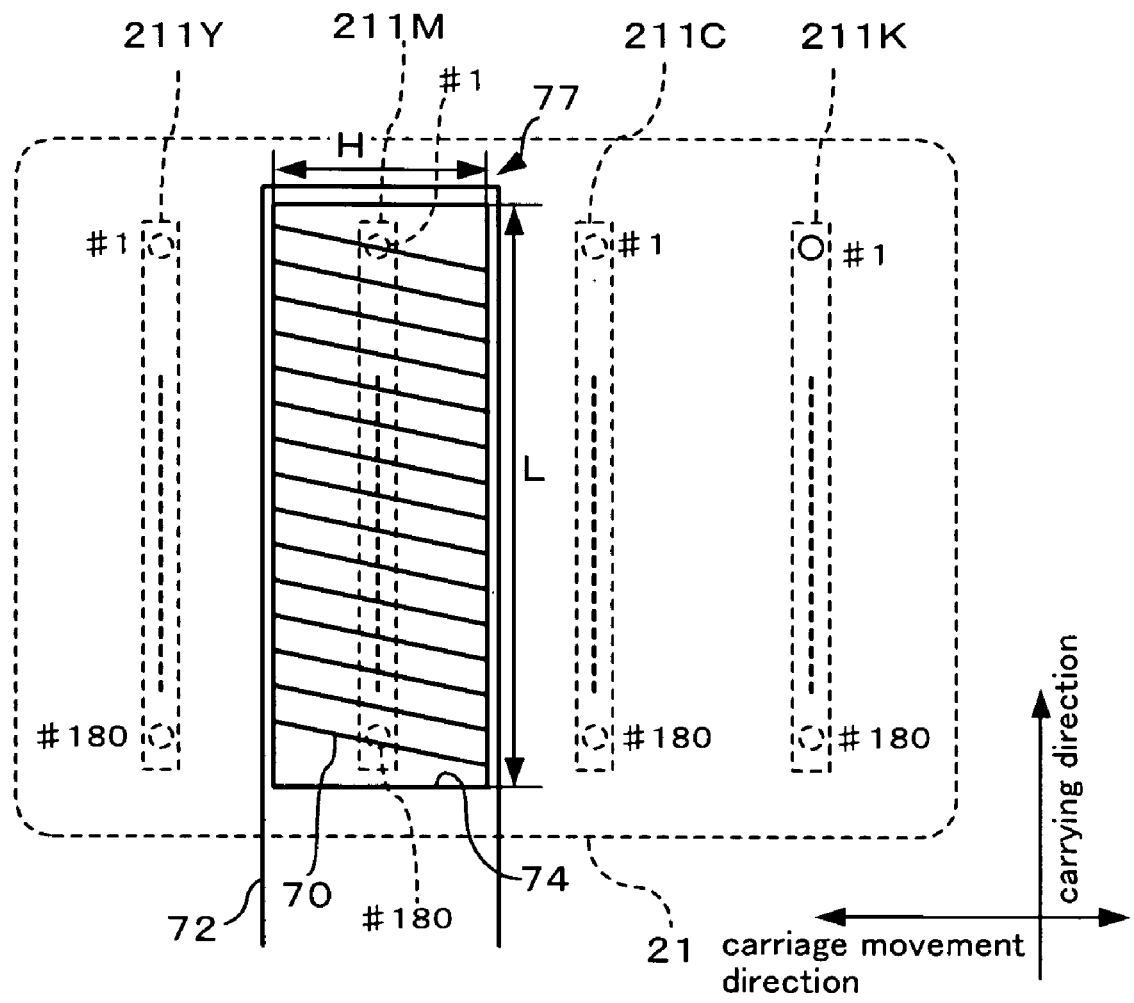
FIG. 18 is a view illustrating the positional relationship between the detection members and nozzle rows.

FIG. 18 illustrates the positional relationship between the ejection testing unit 77 and the nozzle rows 211C, 211M, 211Y, and 211K when the ejection test is performed. As shown in FIG. 18, the longitudinal length L of the opening section 74 disposed at the substrate 72 of the ejection testing unit 77 is set in accordance with the lengthwise length of the nozzle rows 211C, 211M, 211Y, and 211K such that the longitudinal length L is slightly longer than the lengthwise length. Furthermore, the lateral length H of the opening section 74 is set so as to correspond to a width of one row of the nozzle rows 211C, 211M, 211Y, and 211K. The plurality of detection members 70 arranged at the opening section 74 of the ejection testing unit 77 are arranged at an angle in the direction that intersects with the arrangement direction (parallel to the carrying direction in this embodiment) of the nozzles #1 to #180 of the nozzle rows 211C, 211M, 211Y, and 211K, in correspondence with the nozzles #1 to #180 of the nozzle rows 211C, 211M, 211Y, and 211K.

As shown in FIG. 18, when the ejection test is performed, the positional alignment is carried out such that one nozzle row (nozzle row 211M in this embodiment) among the plurality of nozzle rows 211C, 211M, 211Y, and 211K arranged at the head 21 is positioned directly above the detection members 70. After the positional alignment ends, ink is ejected from the nozzles #1 to #180 of the nozzle row 211M toward the respective gaps between the detection members 70 to perform the ejection test.

After the ejection test on the one nozzle row 211M ends, the carriage 41 moves such that the ejection test is performed on other nozzle rows 211C, 211Y, and 211K on which the ejection test has not been performed. Then, the detection members 70 and the next nozzle row (such as the nozzle row 211Y in this embodiment) on which the ejection test is to be performed are positionally aligned, so that the ejection test is performed on the nozzle row 211Y. In this manner, the ejection test is performed one by one on the plurality of nozzle rows 211C, 211M, 211Y, and 211K arranged at the head 21.

===Positional Relationship between Detection Members and Nozzles <No. 1>===

Figure 19:
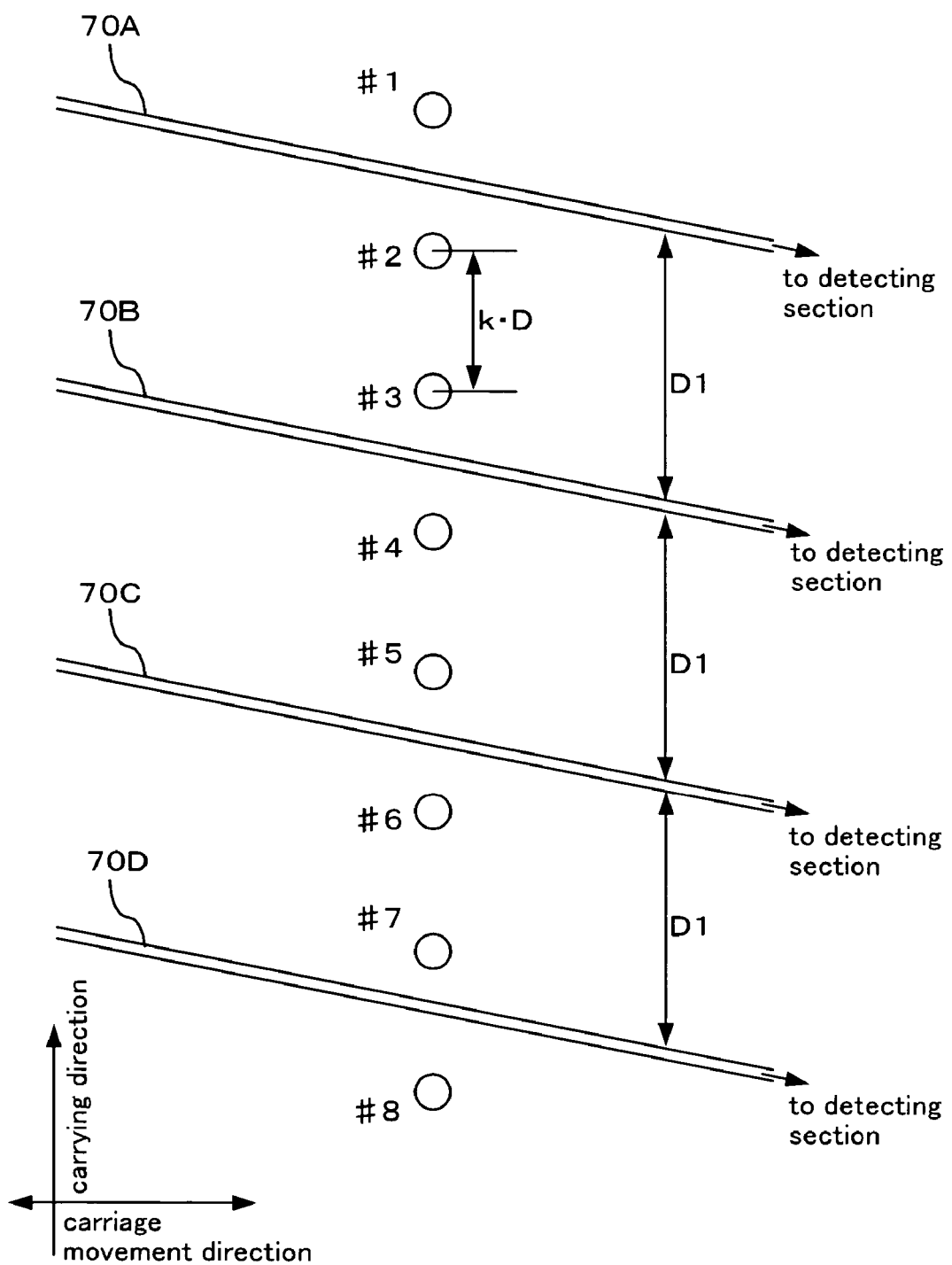
FIG. 19 is a diagram illustrating an example of the positional relationship between the detection members and the nozzles.

FIG. 19 illustrates an example of the positional relationship between the detection members 70 and the nozzles #1 to #180 in the ejection test. The following is a description concerning an example in which the ejection test is performed on the nozzles #1 to #8 with four detection members 70A, 70B, 70C, and 70D. Two nozzles among the nozzles #1 to #8 correspond to each of the detection members 70A, 70B, 70C, and 70D. More specifically, the nozzles #1 and #2 correspond to the detection member 70A. Furthermore, the nozzles #3 and #4 correspond to the detection member 70B. Furthermore, the nozzles #5 and #6 correspond to the detection member 70C. Furthermore, the nozzles #7 and #8 correspond to the detection member 70D.

The detection members 70A, 70B, 70C, and 70D are arranged such that the ejection test is performed with respect to the nozzles #1 to #8 that are arranged in correspondence therewith. More specifically, the detection member 70A is disposed such that the ejection test is performed with respect to the nozzles #1 and #2. Furthermore, the detection member 70B is disposed such that the ejection test is performed with respect to the nozzles #3 and #4. Furthermore, the detection member 70C is disposed such that the ejection test is performed with respect to the nozzles #5 and #6. Furthermore, the detection member 70D is disposed such that the ejection test is performed with respect to the nozzles #7 and #8.

Each of the detection members 70A, 70B, 70C, and 70D is disposed so as to be positioned in the middle between the two corresponding nozzles. More specifically, the detection member 70A is disposed so as to be positioned in the middle between the nozzle #1 and the nozzle #2. Furthermore, the detection member 70B is disposed so as to be positioned in the middle between the nozzle #3 and the nozzle #4. Furthermore, the detection member 70C is disposed so as to be positioned in the middle between the nozzle #5 and the nozzle #6. Furthermore, the detection member 70D is disposed so as to be positioned in the middle between the nozzle #7 and the nozzle #8. Furthermore, each spacing D1 in the carrying direction between the detection members 70A, 70B, 70C, and 70D is set to a spacing that is substantially equal to twice the nozzle spacing k·D.

Accordingly, the spacings between the detection members 70A, 70B, 70C, and 70D, and the nozzles #1 to #8 are all equal to each other. More specifically, the spacing between the detection member 70A and the nozzle #1 or the nozzle #2, the spacing between the detection member 70B and the nozzle #3 or the nozzle #4, the spacing between the detection member 70C and the nozzle #5 or the nozzle #6, and the spacing between the detection member 70D and the nozzle #7 or the nozzle #8 are all equal to each other.

When ink is ejected from the nozzle #1 or the nozzle #2 such that the ejection test is performed on the nozzle #1 or the nozzle #2, an induced current is generated mainly at the detection member 70A. Furthermore, when ink is ejected from the nozzle #3 or the nozzle #4 such that the ejection test is performed on the nozzle #3 or the nozzle #4, an induced current is generated mainly at the detection member 70B. Furthermore, when ink is ejected from the nozzle #5 or the nozzle #6 such that the ejection test is performed on the nozzle #5 or the nozzle #6, an induced current is generated mainly at the detection member 70C. Furthermore, when ink is ejected from the nozzle #7 or the nozzle #8 such that the ejection test is performed on the nozzle #7 or the nozzle #8, an induced current is generated mainly at the detection member 70D. The induced current that has been generated at the detection members 70A, 70B, 70C, and 70D is input via the common line 75 to the detecting section 80 and is detected by the detecting section 80.

In this manner, since two of the nozzles #1 to #8 are arranged in correspondence with each of the detection members 70A, 70B, 70C, and 70D, it is possible to perform the ejection test on the nozzles #1 to #8 at one time. In other words, it is possible to perform the ejection test on the nozzles #1 to #8 at the same position without changing the positional relationship between the detection members 70A, 70B, 70C, and 70D, and the nozzles #1 to #8. Thus, it is possible to efficiently perform the ejection test on the nozzles #1 to #8.

It should be noted that the ejection test on the nozzles #1 to #8 is performed using the method described based on FIGS. 12 to 14C, for example. More specifically, for example, when the test of whether or not ink is ejected is performed, it is judged whether or not ejection is performed, by comparing the magnitude of the induced current that has been generated at the detection members 70A, 70B, 70C, and 70D, that is, the signal level of the detection signal that has been output from the detecting section 80, with the predetermined reference value V0. Furthermore, in the test of the ejection direction of ink, it is judged whether or not the ejection direction of ink is proper, by checking whether or not the peak value of the induced current that has been generated at the detection members 70A, 70B, 70C, and 70D, that is, the peak value Vmax of the detection signal that has been output from the detecting section 80 is within a predetermined tolerance range (at least the minimum tolerance value V1 and at most the maximum tolerance value V2, for example).

===Positional Relationship between Detection Members and Nozzles <No. 2>===

<Positional Relationship>

Figure 20A:
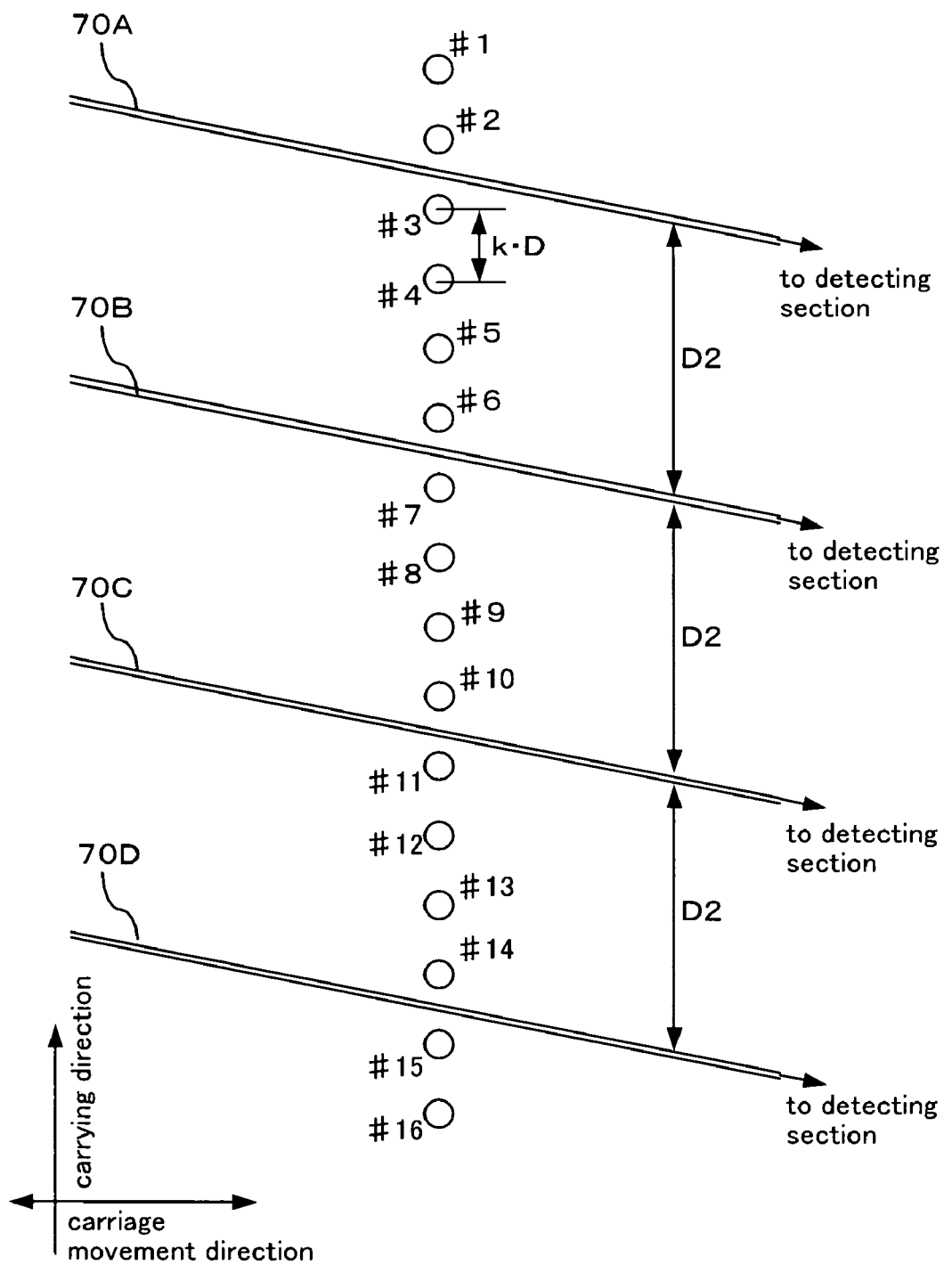
FIG. 20A is a diagram illustrating another example of the positional relationship between the detection members and the nozzles.

FIG. 20A illustrates another example of the positional relationship between the detection members 70 and the nozzles #1 to #180 in the ejection test. The following is a description concerning an example in which the ejection test is performed on the nozzles #1 to #16 with four detection members 70A, 70B, 70C, and 70D. Four nozzles among the nozzles #1 to #16 correspond to each of the detection members 70A, 70B, 70C, and 70D. More specifically, the nozzles #1 to #4 correspond to the detection member 70A. Furthermore, the nozzles #5 to #8 correspond to the detection member 70B. Furthermore, the nozzles #9 to #12 correspond to the detection member 70C. Furthermore, the nozzles #13 to #16 correspond to the detection member 70D.

The detection members 70A, 70B, 70C, and 70D are arranged such that the ejection test is performed with respect to the nozzles #1 to #16. More specifically, the detection member 70A is disposed such that the ejection test is performed with respect to the nozzles #1 to #4. Furthermore, the detection member 70B is disposed such that the ejection test is performed with respect to the nozzles #5 to #8. Furthermore, the detection member 70C is disposed such that the ejection test is performed with respect to the nozzles #9 to #12. Furthermore, the detection member 70D is disposed such that the ejection test is performed with respect to the nozzles #13 to #16.

Each of the detection members 70A, 70B, 70C, and 70D is disposed so as to be positioned in the middle between the four corresponding nozzles More specifically, the detection member 70A is disposed so as to be positioned in the middle between the nozzle #2 and the nozzle #3. Furthermore, the detection member 70B is disposed so as to be positioned in the middle between the nozzle #6 and the nozzle #7. Furthermore, the detection member 70C is disposed so as to be positioned in the middle between the nozzle #10 and the nozzle #11. Furthermore, the detection member 70D is disposed so as to be positioned in the middle between the nozzle #14 and the nozzle #15. Furthermore, each spacing D2 in the carrying direction between the detection members 70A, 70B, 70C, and 70D is set to a spacing that is substantially equal to four times the nozzle spacing k·D.

It should be noted that in this embodiment, the spacings between the detection members 70A, 70B, 70C, and 70D, and the nozzles #1 to #16 are different from each other depending on the nozzles #1 to #16. More specifically, the spacing between the detection member 70A and the nozzles #1 or #4 is different from the spacing between the detection member 70A and the nozzles #2 or #3. Furthermore, the spacing between the detection member 70B and the nozzles #5 or #8 is different from the spacing between the detection member 70B and the nozzles #6 or #7. Furthermore, the spacing between the detection member 70C and the nozzles #9 or #12 is different from the spacing between the detection member 70C and the nozzles #10 or #11. Furthermore, the spacing between the detection member 70D and the nozzles #13 or #16 is different from the spacing between the detection member 70D and the nozzles #14 or #15.

Figure 20B:
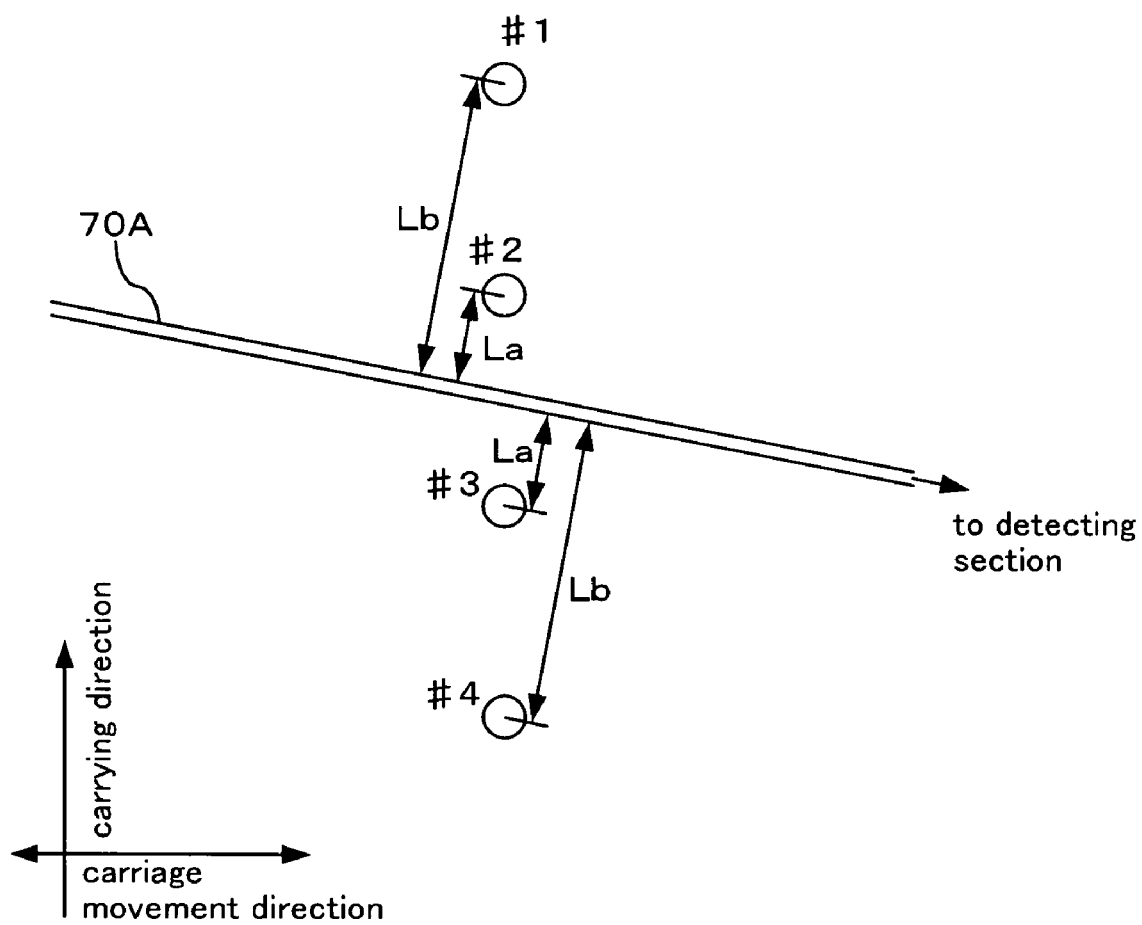
FIG. 20B is a diagram illustrating in detail the positional relationship between the detection member and the nozzles in FIG. 20A.

FIG. 20B illustrates in detail the positional relationship between the detection member 70A and the nozzles #1 to #4. Herein, the nozzles #2 and #3 are arranged at the positions that are close to the detection member 70A. On the other hand, the nozzles #1 and #4 are arranged at the positions that are away from the detection member 70A. Thus, a spacing La between the nozzle #2 or the nozzle #3 and the detection member 70A is much smaller than a spacing Lb between the nozzle #1 or #4 and the detection member 70A.

When ink is ejected from each of the nozzles #1 to #4 such that the ejection test is performed on the nozzles #1 to #4, an induced current is generated mainly at the detection member 70A. Furthermore, when ink is ejected from each of the nozzles #5 to #8 such that the ejection test is performed on the nozzles #5 to #8, an induced current is generated mainly at the detection member 70B. Furthermore, when ink is ejected from each of the nozzles #9 to #12 such that the ejection test is performed on the nozzles #9 to #12, an induced current is generated mainly at the detection member 70C. Furthermore, when ink is ejected from each of the nozzles #13 to #16 such that the ejection test is performed on the nozzles #13 to #16, an induced current is generated mainly at the detection member 70D. The induced current that has been generated at the detection members 70A, 70B, 70C, and 700D is input via the common line 75 to the detecting section 80 and is detected by the detecting section 80.

<Ejection Test>

The following is a description concerning a case in which the ejection test is performed on the nozzles #1 to #16 in this positional relationship. Herein, the spacings La and Lb between the detection members 70A, 70B, 70C, and 70D and the nozzles #1 to #16 corresponding to the detection members 70A, 70B, 70C, and 70D are different from each other depending on the nozzles #1 to #16. Thus, even when the ink droplet Ip is properly ejected from the nozzles #1 to #16, the induced current of different magnitudes is generated at the detection members 70A, 70B, 70C, and 70D. More specifically, in the case of the nozzles #2, #3, #6, #7, #10, #11, #14, and #15 that are positioned close to the detection members 70A, 70B, 70C, and 70D, the magnitude of the induced current generated at the detection members 70A, 70B, 70C, and 70D is large. On the other hand, in the case of the nozzles #1, #4, #5, #8, #9, #12, #13, and #16 that are positioned away from the detection members 70A, 70B, 70C, and 70D, the magnitude of the induced current generated at the detection members 70A, 70B, 70C, and 70D is small.

Thus, in this embodiment, a judgment reference in the ejection test is switched in accordance with the position of the nozzle that is to be tested. More specifically, the judgment reference is switched between a case in which the ejection test is performed on the nozzles #2, #3, #6, #7, #10, #11, #14, and #15 that are positioned close to the detection members 70A, 70B, 70C, and 70D, and a case in which the ejection test is performed on the nozzles #1, #4, #5, #8, #9, #12, #13, and #16 that are positioned away from the detection members 70A, 70B, 70C, and 70D. In this embodiment, the reference value "V0" in the judgment of whether or not ejection is performed, and the minimum tolerance value "V1" and the maximum tolerance value "V2" in the judgment of the ejection direction are switched in accordance with the position of the nozzle that is to be tested.

Figure 21A:
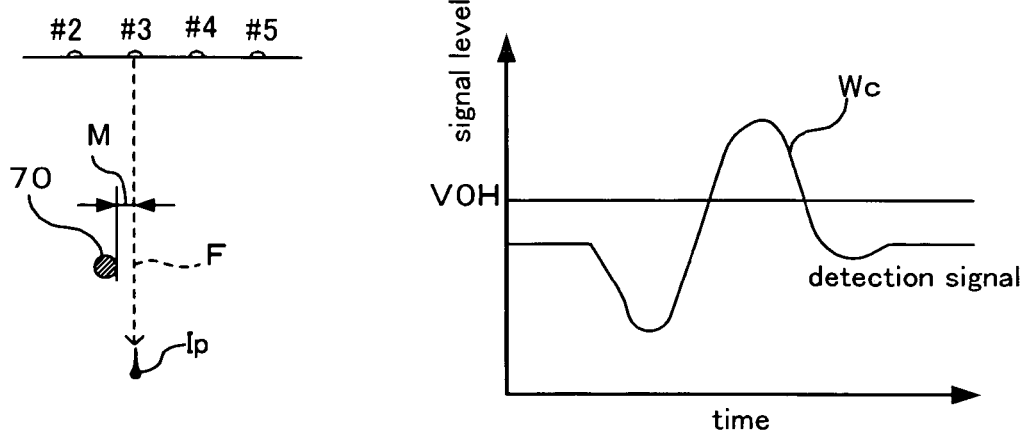
FIG. 21A is an explanatory diagram of an example of a method for judging whether or not ejection is performed, when ink is properly ejected from the nozzle that is close to the detection member in FIG. 20A.
Figure 21B:
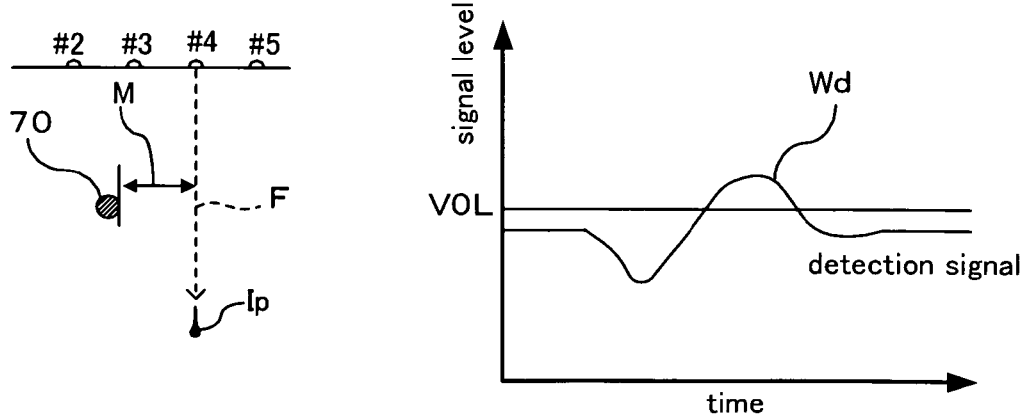
FIG. 21B is an explanatory diagram of an example of a method for judging whether or not ejection is performed, when ink is properly ejected from the nozzle that is away from the detection member in FIG. 20A.

FIGS. 21A and 21B respectively show examples of detection signals that are output from the detecting section 80 when ink is properly ejected from the nozzles #1 to #16 such that the ejection test is performed. FIG. 21A shows an example of the waveform of a detection signal that is output from the detecting section 80 when ink is properly ejected from the nozzles #2, #3, #6, #7, #10, #11, #14, and #15 that are positioned close to the detection members 70A, 70B, 70C, and 70D. FIG. 21B shows an example of the waveform of a detection signal that is output from the detecting section 80 when ink is properly ejected from the nozzles #1, #4, #5, #8, #9, #12, #13, and #16 that are positioned away from the detection members 70A, 70B, 70C, and 70D.

When ink is properly ejected from the nozzles #2, #3, #6, #7, #10, #11, #14, and #15 that are positioned close to the detection members 70A, 70B, 70C, and 70D, a pulse Wc with a large amplitude is generated in the detection signal as shown in FIG. 21A. On the other hand, when ink is properly ejected from the nozzles #1, #4, #5, #8, #9, #12, #13, and #16 that are positioned away from the detection members 70A, 70B, 70C, and 70D, a pulse Wd with a small amplitude is generated in the detection signal as shown in FIG. 21B.

In this manner, even when ink is properly ejected, the magnitudes of the pulses Wc and Wd generated in the detection signal from the detecting section 80 are different between a case of the nozzles #2, #3, #6, #7, #10, #11, #14, and #15 that are positioned close to the detection members 70A, 70B, 70C, and 70D and a case of the nozzles #1, #4, #5, #8, #9, #12, #13, and #16 that are positioned away from the detection members 70A, 70B, 70C, and 70D.

Thus, when the test of whether or not ink is ejected is performed, the reference value V0 serving as the reference when judging whether or not ink is ejected is switched between a case in which the test is performed on the nozzles #2, #3, #6, #7, #10, #11, #14, and #15 that are positioned close to the detection members 70A, 70B, 70C, and 70D, and a case in which the test is performed on the nozzles #1, #4, #5, #8, #9, #12, #13, and #16 that are positioned away from the detection members 70A, 70B, 70C, and 70D.

Herein, when the test is performed on the nozzles #2, #3, #6, #7, #10, #11, #14, and #15 that are positioned close to the detection members 70A, 70B, 70C, and 70D, "V0H" is used as a reference value, for example. On the other hand, when the test is performed on the nozzles #1, #4, #5, #8, #9, #12, #13, and #16 that are positioned away from the detection members 70A, 70B, 70C, and 70D, "V0L", which is lower than "V0H", is used as a reference value. Thus, the test of whether or not ink is ejected can be performed as appropriate in accordance with the spacing between the detection members 70A, 70B, 70C, and 70D and the nozzles #1 to #16.

Furthermore, when the test of the ejection direction of ink is performed, a reference when judging the ejection direction of ink is switched between a case in which the test is performed on the nozzles #2, #3, #6, #7, #10, #11, #14, and #15 that are positioned close to the detection members 70A, 70B, 70C, and 70D, and a case in which the test is performed on the nozzles #1, #4, #5, #8, #9, #12, #13, and #16 that are positioned away from the detection members 70A, 70B, 70C, and 70D.

Figure 22A:
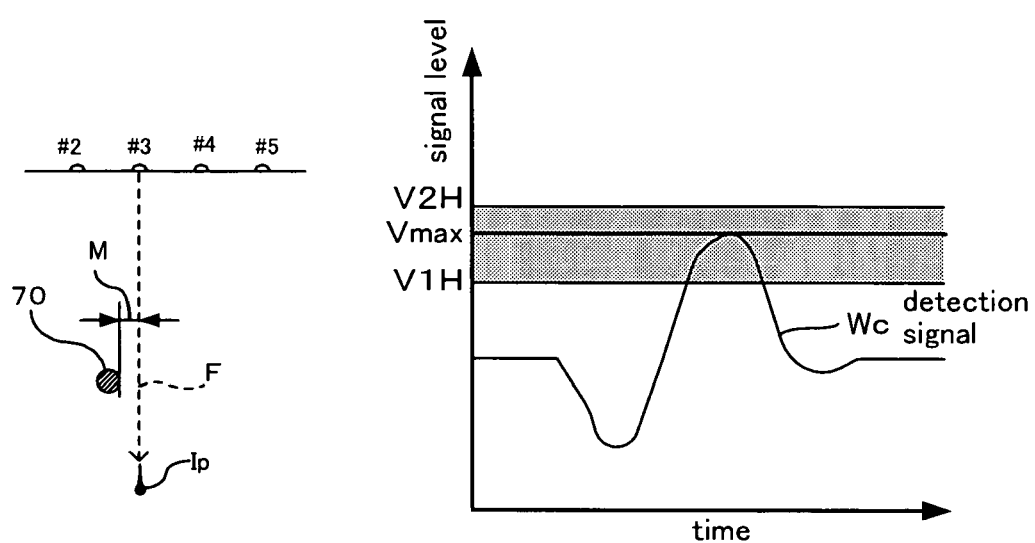
FIG. 22A is an explanatory diagram of an example of a method for judging the ejection direction, when ink is properly ejected from the nozzle that is close to the detection member in FIG. 20A.
Figure 22B:
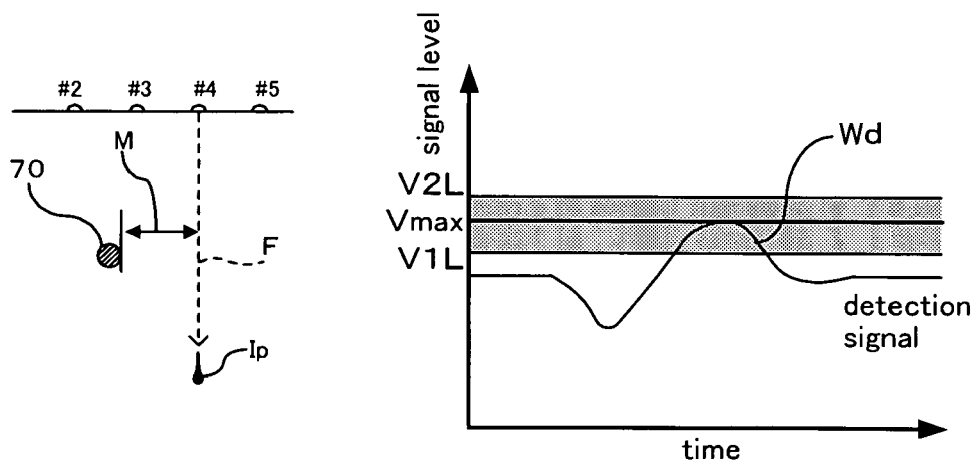
FIG. 22B is an explanatory diagram of an example of a method for judging the ejection direction, when ink is properly ejected from the nozzle that is away from the detection member in FIG. 20A.

FIGS. 22A and 22B illustrate the judgment references when the test of the ejection direction of ink is performed. FIG. 22A illustrates the case of the nozzles #2, #3, #6, #7, #10, #11, #14, and #15 that are positioned close to the detection members 70A, 70B, 70C, and 70D. FIG. 22B illustrates the case of the nozzles #1, #4, #5, #8, #9, #12, #13, and #16 that are positioned away from the detection members 70A, 70B, 70C, and 70D.

As shown in FIG. 22A, when the test is performed on the nozzles #2, #3, #6, #7, #10, #11, #14, and #15 that are positioned close to the detection members 70A, 70B, 70C, and 70D, "V1H" is used as a minimum tolerance value and "V2H" is used as a maximum tolerance value. On the other hand, as shown in FIG. 22B, when the test is performed on the nozzles #1, #4, #5, #8, #9, #12, #13, and #16 that are positioned away from the detection members 70A, 70B, 70C, and 70D, "V1L" is used as a minimum tolerance value and "V2L" is used as a maximum tolerance value. Thus, the test of the ejection direction of ink can be performed as appropriate in accordance with the spacing between the detection members 70A, 70B, 70C, and 70D and the nozzles #1 to #16.

FIG. 22C is a table showing all the reference values "V0H", "V0L", "V1H", "V2H", "V1L", and "V2L", serving as the judgment references in the ejection test, in a case where the test is performed on the nozzles #2, #3, #6, #7, #10, #11, #14, and #15 that are positioned close to the detection members 70A, 70B, 70C, and 70D, and in a case where the test is performed on the nozzles #1, #4, #5, #8, #9, #12, #13, and #16 that are positioned away from the detection members 70A, 70B, 70C, and 70D.

It should be noted that the reference values "V0H", "V0L", "V1H", "V2H", "V1L", and "V2L", serving as the judgment references in the ejection test, are stored as data in an appropriate storing section, for example, a memory such as the main memory 127. When comparing the signal level of the detection signal with the reference values "V1H", "V1L", "V2H", "V2L", "V0H", and "V0L", the controller 126 acquires information on the reference values "V1H", "V1L", "V2H", "V2L", "V0H", and "V0L" from an appropriate storing section such as the main memory 127.

===Positional Relationship between Detection Members and Nozzles <No. 3>===

Figure 23A:
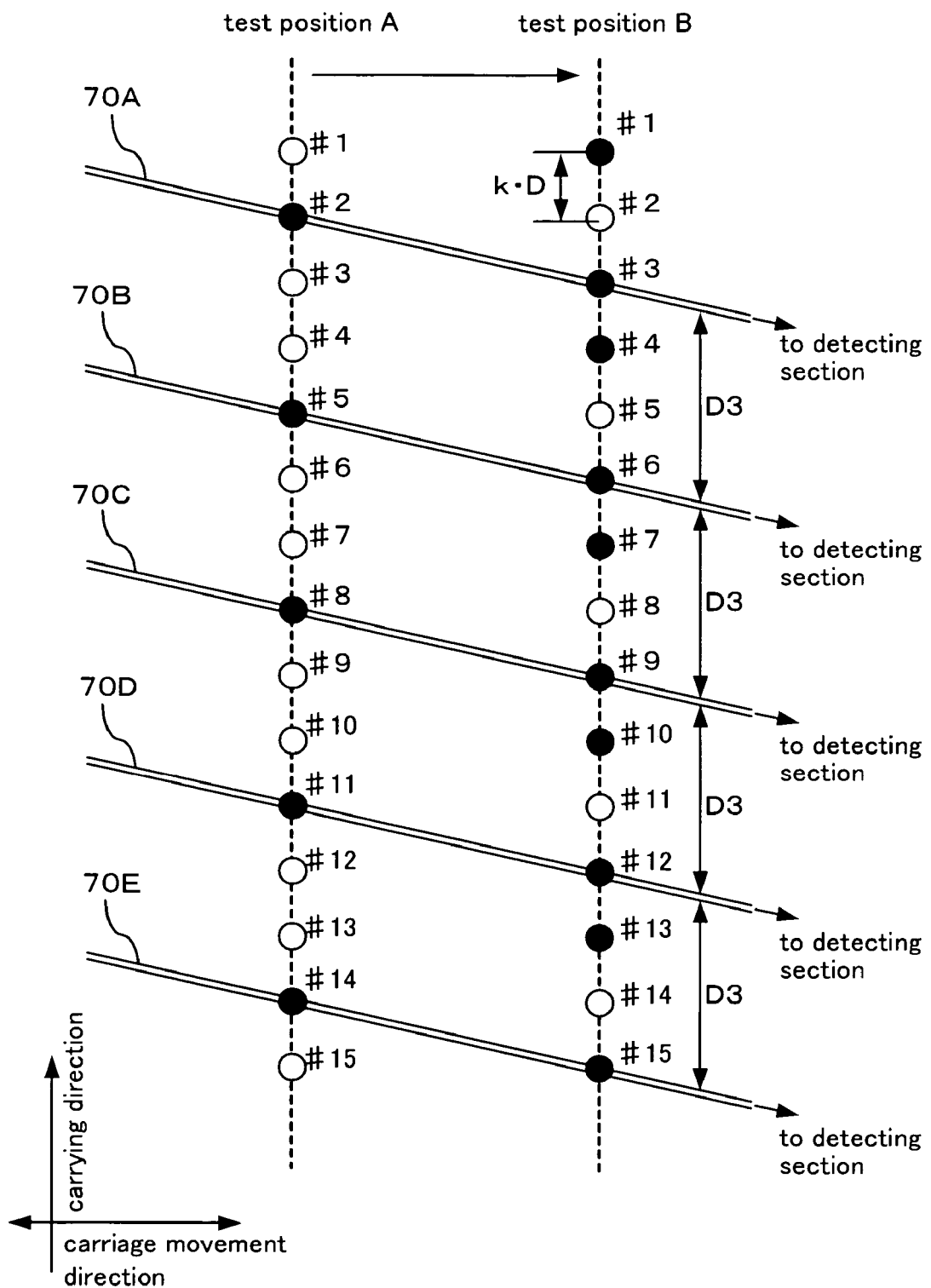
FIG. 23A is a diagram illustrating another example <No. 1> of the positional relationship between the detection members and the nozzles.

FIG. 23A illustrates another example of the positional relationship between the detection members 70 and the nozzles #1 to #180 in the ejection test. The following is a description concerning an example in which the ejection test is performed on the nozzles #1 to #15 with five detection members 70A, 70B, 70C, 70D, and 70E. A spacing D3 in the carrying direction between the detection members 70A, 70B, 70C, 70D, and 70E is set to a spacing that is substantially equal to three times the nozzle spacing k·D.

Herein, two test positions A and B are arranged such that the ejection test is performed on the nozzles #1 to #15. The test position A is set such that the ejection test is performed on the nozzles #1, #3, #4, #6, #7, #9, #10, #12, #13, and #15. On the other hand, the test position B is set such that the ejection test is performed on the nozzles #2, #5, #8, #11, and #14. Here, the nozzles that are to be tested at the test position A or B are represented by white circles "○". Furthermore, the nozzles that are not to be tested at the test position A or B are represented by black circles "●".

The two test positions A and B are changed when the carriage 41 (nozzles #1 to #15) moves in the movement direction of the carriage 41. More specifically, when the nozzles #1 to #180 (nozzles #1 to #15 in this embodiment) arranged at the head 21 of the carriage 41 move relative to the detection members 70A, 70B, 70C, 70D, and 70E (ejection testing unit 77), the test positions are changed. Herein, first, the ejection test is performed at the test position A. Next, after the carriage 41 has moved, the ejection test is performed at the test position B. In other words, the nozzles #1 to #15 move relatively from the test position A to the test position B in accordance with the movement of the carriage 41.

The reason why the two test positions A and B are arranged is that the positions of the detection members 70A, 70B, 70C, 70D, and 70E respectively overlap with the positions of the nozzles #2, #5, #8, #11, and #14 at the test position A. When the positions of the detection members 70A, 70B, 70C, 70D, and 70E respectively overlap with the positions of the nozzles #2, #5, #8, #11, and #14 in this manner, the ink droplet Ip ejected from the nozzles #2, #5, #8, #11, and #14 may be brought into contact with the detection members 70A, 70B, 70C, 70D, and 70E in the ejection test. When the ink droplet Ip ejected from the nozzles #2, #5, #8, #11, and #14 is brought into contact with the detection members 70A, 70B, 70C, 70D, and 70E, there is a possibility that a sufficient induced current is not generated at the detection members 70A, 70B, 70C, 70D, and 70E. When a sufficient induced current is not generated at the detection members 70A, 70B, 70C, 70D, and 70E in this manner, the ejection test may not be sufficiently performed on the nozzles. Thus, it is preferable that ink ejected from the nozzles that are to be tested is not brought into contact with the detection members 70A, 70B, 70C, 70D, and 70E to the extent possible. It goes without saying that this does not eliminate cases in which ink ejected from the nozzles that are to be tested comes into contact with the detection members 70A, 70B, 70C, 70D, and 70E, in the ejection test.

At the test position A, since the nozzles #2, #5, #8, #11, and #14 respectively overlap with the detection members 70A, 70B, 70C, 70D, and 70E, the nozzles are not to be tested. On the other hand, when the nozzles #1 to #15 move to the test position B in accordance with the movement of the carriage 41, the nozzles #2, #5, #8, #11, and #14 that are not tested at the test position A do not overlap with the detection members 70A, 70B, 70C, 70D, and 70E. Thus, at the test position B, it is possible to perform the ejection test on the nozzles #2, #5, #8, #11, and #14 that are not tested at the test position A.

At the test position A, the nozzles #1 and #3 correspond to the detection member 70A. Furthermore, the nozzles #4 and #6 correspond to the detection member 70B. Furthermore, the nozzles #7 and #9 correspond to the detection member 70C. Furthermore, the nozzles #10 and #12 correspond to the detection member 70D. Furthermore, the nozzles #13 and #15 correspond to the detection member 70E.

On the other hand, at the test position B, the nozzle #2 corresponds to the detection member 70A. Furthermore, the nozzle #5 corresponds to the detection member 70B. Furthermore, the nozzle #8 corresponds to the detection member 70C. Furthermore, the nozzle #11 corresponds to the detection member 70D. Furthermore, the nozzle #14 corresponds to the detection member 70E.

It should be noted that the ejection test on the nozzles #1 to #15 is performed using the method described based on FIGS. 12 to 14C, for example. More specifically, for example, when the test of whether or not ink is ejected is performed, it is judged whether or not ejection is performed, by comparing the magnitude of the induced current that has been generated at the detection members 70A, 70B, 70C, 70D, and 70E, that is, the signal level of the detection signal that has been output from the detecting section 80, with the predetermined reference value "V0H" or "V0L". Furthermore, in the test of the ejection direction of ink, it is judged whether or not the ejection direction of ink is proper, by checking whether or not the peak value of the induced current that has been generated at the detection members 70A, 70B, 70C, 70D, and 70E, that is, the peak value Vmax of the detection signal that has been output from the detecting section 80 is within a predetermined tolerance range (at least the minimum tolerance value "V1H" or "V1L" and at most the maximum tolerance value "V2H" or "V2L", for example).

===Positional Relationship between Detection Members and Nozzles <No. 4>===

Figure 23B:
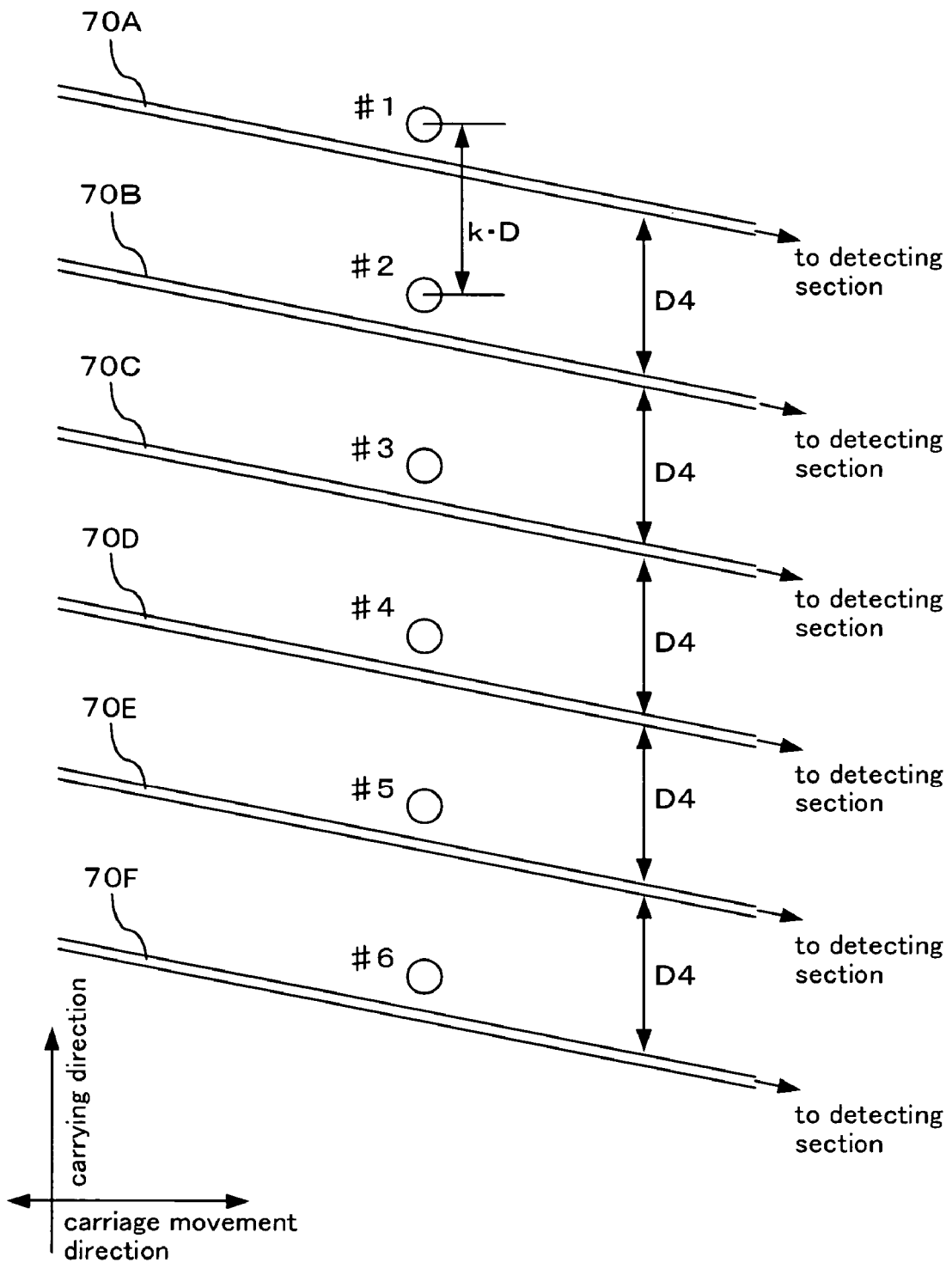
FIG. 23B is a diagram illustrating another example <No. 2> of the positional relationship between the detection members and the nozzles.

FIG. 23B illustrates another example of the positional relationship between the detection members 70 and the nozzles #1 to #180 in the ejection test. The following is a description concerning an example in which the ejection test is performed on the nozzles #1 to #6 with six detection members 70A, 70B, 70C, 70D, 70E, and 70F. A spacing D4 in the carrying direction between the detection members 70A, 70B, 70C, 70D, 70E, and 70F is set to a spacing that is substantially equal to the nozzle spacing k·D. The nozzles #1 to #6 respectively correspond to the detection members 70A, 70B, 70C, 70D, 70E, and 70F. More specifically, the nozzle #1 corresponds to the detection member 70A, the nozzle #2 corresponds to the detection member 70B, the nozzle #3 corresponds to the detection member 70C, the nozzle #4 corresponds to the detection member 70D, the nozzle #5 corresponds to the detection member 70E, and the nozzle #6 corresponds to the detection member 70F. The detection members 70A, 70B, 70C, 70D, 70E, and 70F are arranged in the vicinity of the nozzles #1 to #6 such that the ejection test is respectively performed on the corresponding nozzles #1 to #6.

When ink is ejected from each of the nozzles #1 to #6 in the ejection test, an induced current is generated mainly at the detection members 70A, 70B, 70C, 70D, 70E, and 70F corresponding to the nozzles #1 to #6. More specifically, when ink is ejected from the nozzle #1, an induced current is generated mainly at the detection member 70A. When ink is ejected from the nozzle #2, an induced current is generated mainly at the detection member 70B. When ink is ejected from the nozzle #3, an induced current is generated mainly at the detection member 70C. When ink is ejected from the nozzle #4, an induced current is generated mainly at the detection member 70D. When ink is ejected from the nozzle #5, an induced current is generated mainly at the detection member 70E. When ink is ejected from the nozzle #6, an induced current is generated mainly at the detection member 70F.

In this manner, since the detection members 70A, 70B, 70C, 70D, 70E, and 70F are arranged in correspondence with the nozzles #1 to #6, it is possible to efficiently perform the ejection test on the nozzles #1 to #6. It should be noted that also in this case, the ejection test on the nozzles #1 to #6 is performed using the method described based on FIGS. 12 to 14C, for example.

===Testing Procedure===

<Outline of Testing Procedure>

Figure 24A:
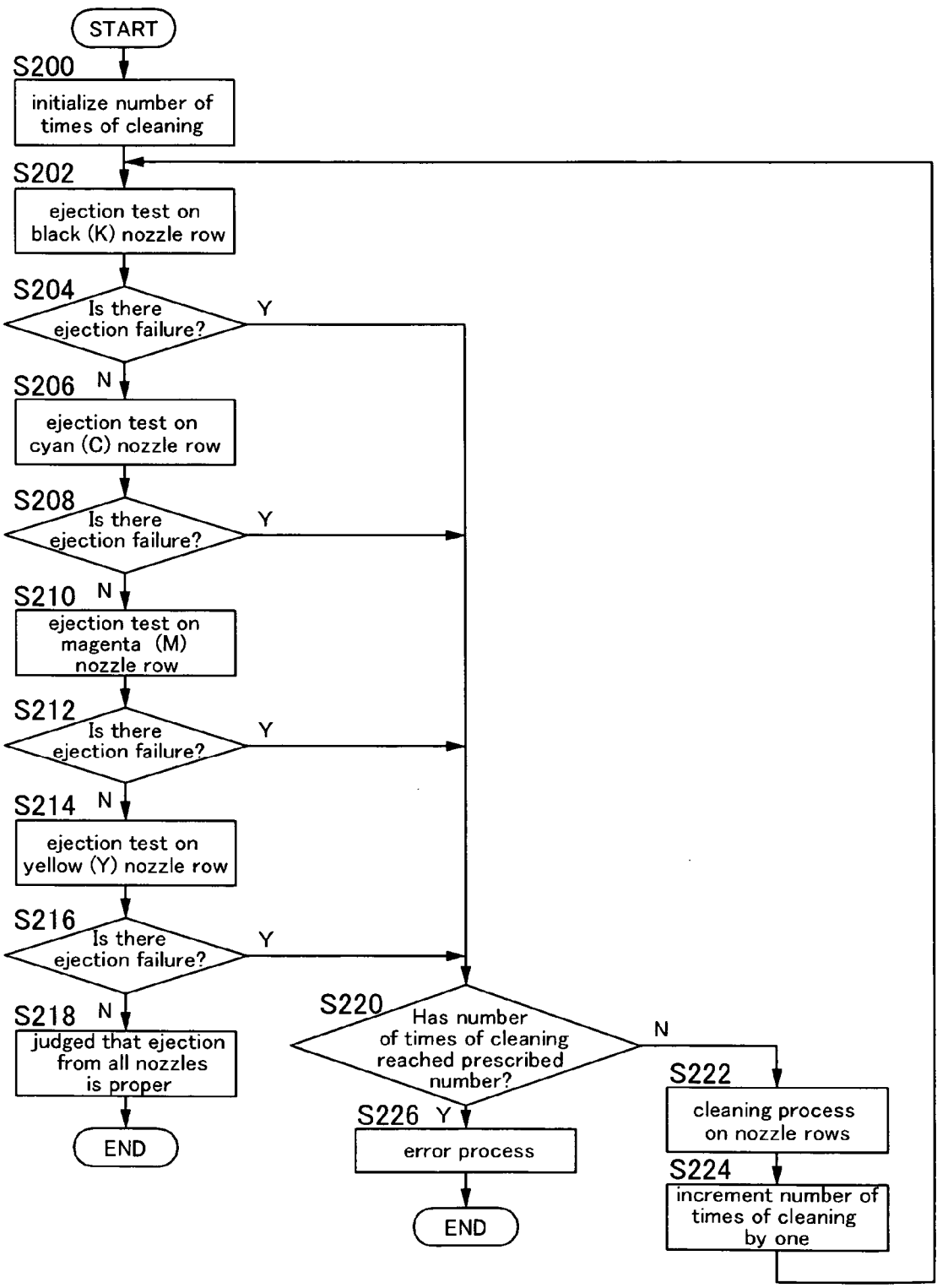
FIG. 24A is a flowchart illustrating an example of an ejection testing procedure for each nozzle row.

Next, the testing procedure is described. FIG. 24A is a flowchart illustrating an example of the testing procedure in the inkjet printer 1 according to this embodiment. In this embodiment, since the detection members 70 arranged on the substrate 72 correspond to only one row of the nozzle rows, the ejection test is performed separately for each of the nozzle rows 211K, 211C, 211M, and 211Y while moving the carriage 41 (head 21) with the nozzle rows 211K, 211C, 211M, and 211Y. Herein, the ejection test is performed in the order: black (K) nozzle row 211K, to cyan (C) nozzle row 211C, to magenta (M) nozzle row 211M, and to yellow (Y) nozzle row 211Y.

First, the number of times of cleaning is initialized (S200). In this step, a counter for counting the number of times of cleaning process is set to 0. Then, the ejection test is performed on the black (K) nozzle row 211K (S202). Here, the ejection test refers to a test of whether or not ink is ejected from the nozzles and a test of the ejection direction of ink, for example. More detailed description of the ejection test for each of the nozzle rows 211K, 211C, 211M, and 211Y, which is performed here, is given later. After the ejection test ends, it is checked whether or not there is a nozzle among the nozzles #1 to #180 of the black (K) nozzle row 211K from which ink is not properly ejected (S204). Here, if there is an ejection failure at even one nozzle among the nozzles #1 to #180 of the black (K) nozzle row 211K, then it is checked whether or not the number of times of cleaning has reached a prescribed number by checking the number of times of cleaning up to this point (S220). Here, the prescribed number is a number at which it is not conceivable that ejection will be restored even if a cleaning process is repeated this number or more. For example, when this number of times is taken as three, if the number of times of cleaning is smaller than three, then the cleaning process is performed on the nozzle row (S222). Herein, the cleaning process is performed with the pump device 31, for example, and may be performed only on the black (K) nozzle row 211K or may be performed at the same time on other nozzle rows. After the cleaning process ends, the number of times of cleaning is incremented by one (S224), and then the ejection test on the nozzle row is again performed.

If the number of times of cleaning has reached the prescribed number in step S220, then an error process is performed (S226), and then the procedure ends. Herein, the error process is a process in which a user is notified that there is a nozzle with an ejection failure that is not eliminated even with cleaning, so as to recommend the user taking more effective measure for restoring ejection. In this error process, changing the head 21 having a nozzle with such an ejection failure may be recommended. Furthermore, in this error process, information on a nozzle with an ejection failure may be stored such that printing is continued using another nozzle instead of the nozzle with an ejection failure.

On the other hand, if there is no nozzle with an ejection failure among the nozzles #1 to #180 of the black (K) nozzle row 211K, then the procedure proceeds to step S206, where the ejection test is performed on the cyan (C) nozzle row 211C (S206). After the ejection test ends, it is checked whether or not there is an ejection failure at the nozzles #1 to #180 of the cyan (C) nozzle row 211C (S208). Herein, if there is an ejection failure at even one nozzle among the nozzles #1 to #180 of the cyan (C) nozzle row 211C, then the procedure proceeds to step S220 in which the number of times of cleaning is checked.

On the other hand, if there is no nozzle with an ejection failure among the nozzles #1 to #180 of the cyan (C) nozzle row 211C, then the procedure proceeds to step S210, where the ejection test is performed on the magenta (M) nozzle row 211M (S210). After the ejection test ends, it is checked whether or not there is a nozzle with an ejection failure among the nozzles #1 to #180 of the magenta (M) nozzle row 211M (S212). Herein, if there is an ejection failure at even one nozzle among the nozzles #1 to #180 of the magenta (M) nozzle row 211M, then the procedure proceeds to step S220 in which the number of times of cleaning is checked.

On the other hand, if there is no nozzle with an ejection failure in the magenta (M) nozzle row 211M, then the procedure proceeds to step S214, where the ejection test is performed on the yellow (Y) nozzle row 211Y (S214). After the ejection test ends, it is checked whether or not there is a nozzle with an ejection failure among the nozzles #1 to #180 of the yellow (Y) nozzle row 211Y (S216). Herein, if there is an ejection failure at even one nozzle among the nozzles #1 to #180 of the yellow (Y) nozzle row 211Y, then the procedure proceeds to step S220 in which the number of times of cleaning is checked.

On the other hand, if there is no nozzle with an ejection failure among the nozzles #1 to #180 of the yellow (Y) nozzle row 211Y, it is judged that there is no nozzle with an ejection failure among the nozzles #1 to #180 of the nozzle rows 211K, 211C, 211M, and 211Y of all colors, that is, all nozzles are proper (S218), and then the procedure ends.

<Other Testing Procedures>

Figure 24B:
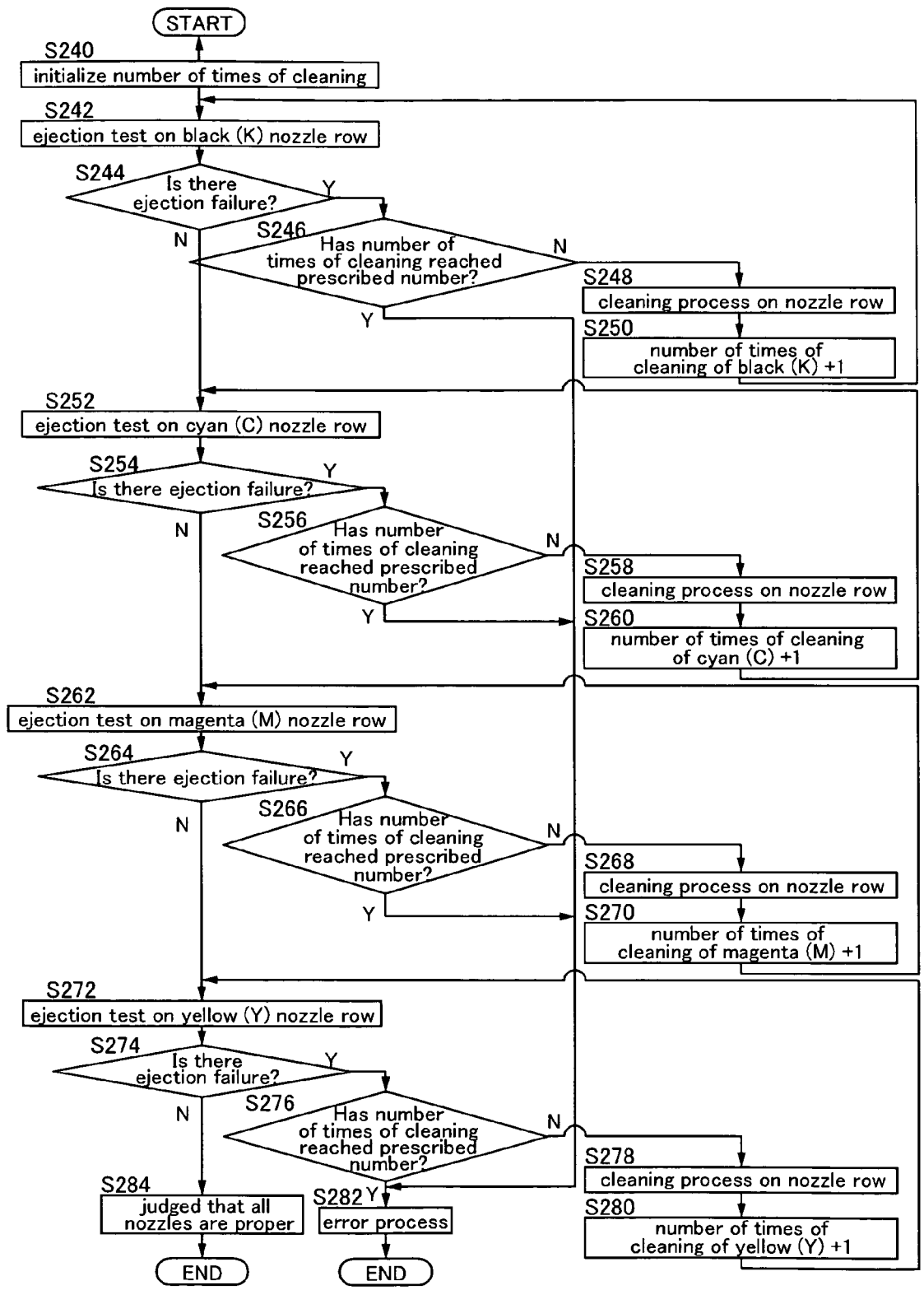
FIG. 24B is a flowchart illustrating another example of an ejection testing procedure for each nozzle row.

FIG. 24B is a flowchart illustrating a case in which the cleaning process is performed on each nozzle row. First, the number of times of cleaning is initialized (S240). In this step, all counters for counting, with respect to each nozzle row, the number of times the cleaning process is performed during a single ejection test, that is, the number of times a nozzle from which ejection is not proper is found, are set to 0. Then, the ejection test is performed on the black (K) nozzle row 211K (S242). After the ejection test ends, it is checked whether or not there is a nozzle among the nozzles #1 to #180 of the black (K) nozzle row 211K from which ink is not properly ejected (S244). Here, if there is even one nozzle among the nozzles #1 to #180 of the black (K) nozzle row 211K from which ejection is not proper, then it is checked whether or not the number of times of cleaning of the black (K) nozzle row 211K has reached a prescribed number (S246). If the number of times of cleaning is smaller than the prescribed number, then the cleaning process is performed on the black (K) nozzle row 211K (S248). After the cleaning process ends, the number of times of cleaning of the black (K) nozzle row 211K is incremented by one (S250), and then the ejection test on the nozzle row is again performed on the black (K) nozzle row 211K.

If the number of times of cleaning has reached the prescribed number in step S246, then the error process is performed (S282), and then the procedure ends.

On the other hand, if ejection from all of the nozzles #1 to #180 of the black (K) nozzle row 211K is proper, then the procedure proceeds to step S252, where the ejection test is performed on the cyan (C) nozzle row 211C (S252). After the ejection test, it is checked whether or not there is a nozzle among the nozzles #1 to #180 of the cyan (C) nozzle row 211C from which ink is not properly ejected (S254). Herein, if there is even one nozzle among the nozzles #1 to #180 of the cyan (C) nozzle row 211C from which ink is not properly ejected, then it is checked whether or not the number of times of cleaning of the cyan (C) nozzle row 211C has reached a prescribed number (S256). If the number of times of cleaning is smaller than the prescribed number, then the cleaning process is performed on the cyan (C) nozzle row 211C (S258). After the cleaning process ends, the number of times of cleaning of the cyan (C) nozzle row 211C is incremented by one (S260), and then the ejection test on the nozzle row is again performed on the cyan (C) nozzle row 211C.

If the number of times of cleaning has reached the prescribed number in step S256, then the error process is performed (S282), and then the procedure ends.

Subsequently, the ejection test is performed in a similar manner also on the magenta (M) and yellow (Y). If there is even one nozzle among the nozzles #1 to #180 from which ejection is not proper, then it is checked whether or not the number of times of cleaning of the nozzle row has reached a prescribed number. If the number of times of cleaning is smaller than the prescribed number, then the cleaning process is performed. Then, the number of times of cleaning of the nozzle row is incremented by one, and the ejection test is again performed. If the number of times of cleaning has reached the prescribed number, then the error process is performed (S282), and then the procedure ends.

When ejection from all of the nozzles #1 to #180 of the yellow (Y) nozzle row 211Y is proper in step S274, there is no nozzle among the nozzles #1 to #180 of the nozzle rows 211K, 211C, 211M, and 211Y of all colors from which ejection is not proper, and thus it is judged that "all ejection is proper" (S284) and the process ends.

<Ink Ejection>

Figure 25:
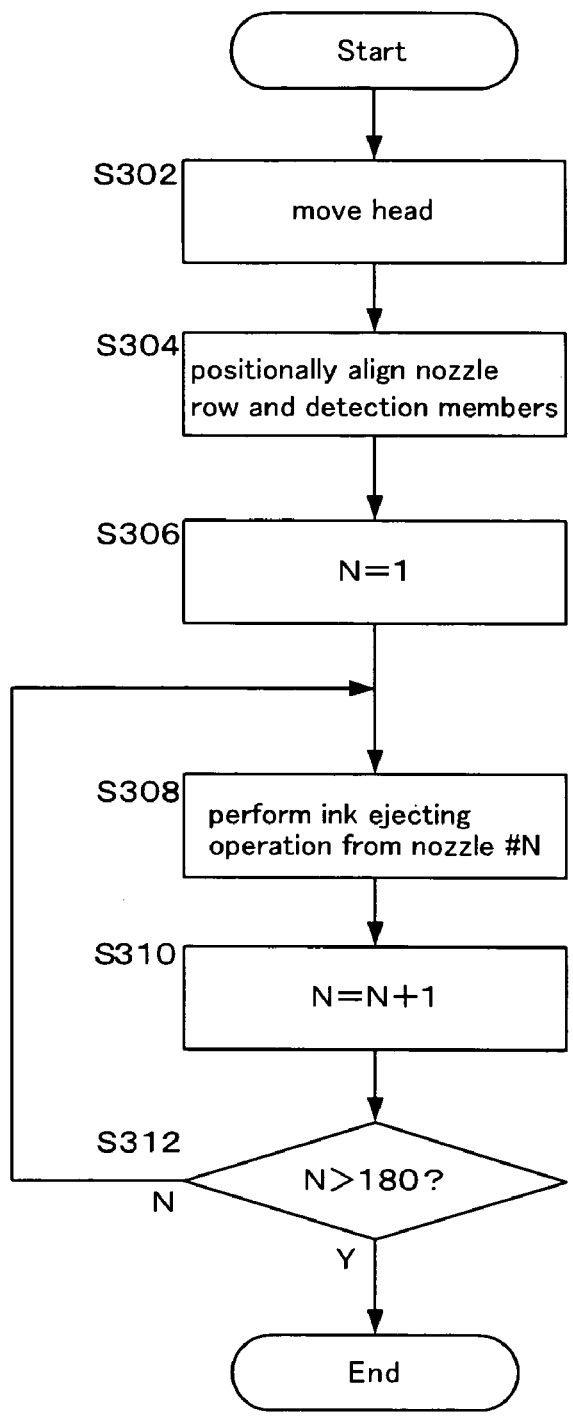
FIG. 25 is a flowchart illustrating an example of an ink ejection procedure for each nozzle when testing.

FIG. 25 is a flowchart illustrating the procedure of the ejection test on each of the nozzle rows 211K, 211C, 211M, and 211Y. First, the head 21 is led to move toward the detection members 70 (S302). Then, any one nozzle row of the nozzle rows 211C, 211M, 211Y, and 211K that are to be tested and the detection members 70 are positionally aligned (S304). Next, a variable N is set to an initial value of 1 (S306), and the ejection test is performed by carrying out an operation in which the ink droplet Ip of a one-time amount (one-droplet amount) is ejected from an N-th nozzle (nozzle #N) toward the side of the detection member 70 (S308). After the ejection, the variable N is set to a value of N+1 (S310), and it is checked whether or not the variable N is larger than the number of nozzles 180 (S312). Herein, if the variable N is larger than 180, then the procedure ends because the ejection test ends on all of the nozzles.

On the other hand, if the variable N is not larger than 180, then the procedure returns to step S308 because the ejection test has not ended on all of the nozzles #1 to #180, so that the ejection test is performed by carrying out an operation in which ink is ejected from an N+1-th nozzle (nozzle #N+1) (S308). Then, the variable N is again set to a value of N+1 (S310), and the ejection test is sequentially performed separately for each of the nozzles #1 to #180 until the variable N becomes larger than the number of nozzles 180.

It should be noted that these series of testing process is performed by the controller 126 based on programs read out from the main memory 127, for example, or may be performed based on instructions from the computer 140, in this embodiment.

<Judging Process>

Figure 26:
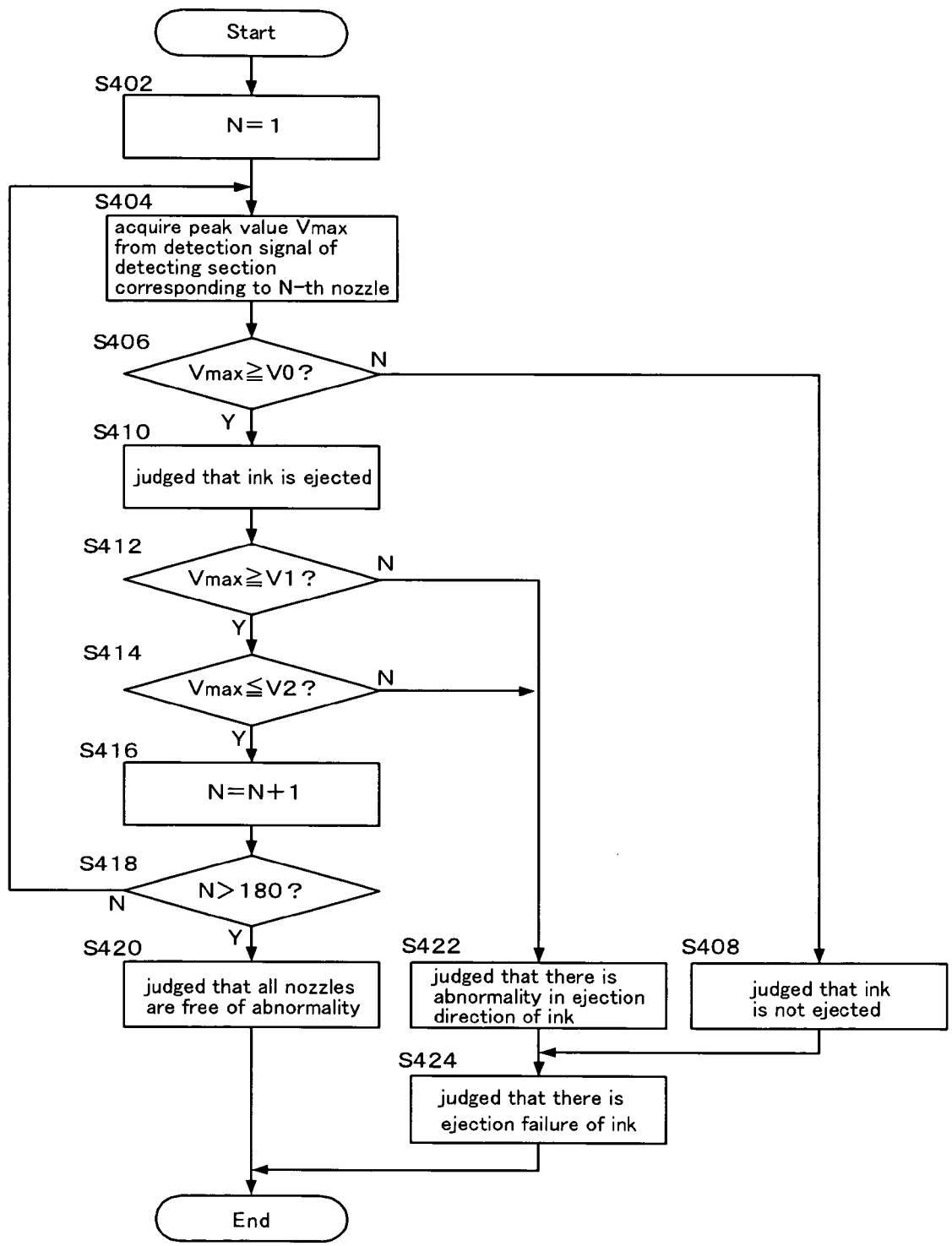
FIG. 26 is a flowchart illustrating an example of an ejection judging procedure for each nozzle when testing.

FIG. 26 is a flowchart illustrating an example of the judging procedure performed by the controller 126. The controller 126 sets the variable N to an initial value of 1 (S402). Next, the controller 126 acquires the peak value Vmax from the detection signal output from the detecting section 80, which corresponds to the N-th nozzle (nozzle #N) (S404). Next, the controller 126 compares the acquired peak value Vmax with the predetermined reference value V0 (reference value "V0H", "V0L" for judging whether or not ejection is performed) (S406). Herein, if the peak value Vmax is lower than the predetermined reference value V0, then the procedure proceeds to step S408, where it is judged that ink is not ejected from the nozzle. Then, the controller 126 judges that there is an ejection failure of ink at the nozzle (S424), and then the process ends. On the other hand, if the acquired peak value Vmax is higher than the predetermined reference value V0, the controller 126 judges that ink is ejected from the nozzle (S410). Next, the procedure proceeds to step S412 such that the controller 126 checks the ejection direction of ink from the nozzle. Herein, the controller 126 checks whether or not the acquired peak value Vmax is not lower than the lower limit value of the predetermined tolerance range, that is, the minimum tolerance value V1 ("V1H", "V1L") (S412). Herein, if the peak value Vmax is lower than the minimum tolerance value V1, that is, if the peak value Vmax is out of the tolerance range, then it is judged that there is an abnormality in the ejection direction of ink (S422). Then, the controller 126 judges that there is an ejection failure of ink at the nozzle row (S424), and then the process ends.

On the other hand, if the peak value Vmax is not lower than the minimum tolerance value V1, then the controller 126 checks whether or not the peak value Vmax is not higher than the upper limit of the predetermined tolerance range, that is, the maximum tolerance value V2 ("V2H", "V2L") (S414). Herein, if the peak value Vmax is higher than the maximum tolerance value V2, that is, if the peak value Vmax is out of the tolerance range, then it is judged that there is an abnormality in the ejection direction of ink (S422). Then, the controller 126 judges that there is an ejection failure of ink at the nozzle row (S424), and then the process ends.

On the other hand, if the peak value Vmax is not higher than the maximum tolerance value V2, then the controller 126 judges that the ejection direction of ink at the N-th nozzle (nozzle #N) is free of abnormality, that is, the ejection direction of ink is proper, and sets the variable N to a value of N+1 to perform the judgment on the next nozzle (S416). Then, the controller 126 checks whether or not the set variable N is larger than the number of nozzles 180 (S418). Herein, if the variable N is not larger than 180, then the procedure returns to step S404, where the controller 126 performs the test on another new nozzle (N+1-th nozzle) on which the test has not been performed. On the other hand, if the variable N is larger than 180, then the controller 126 judges that the test ends on all of the nozzles of a particular nozzle row, and the procedure proceeds to step S420, where it is judged that there is no nozzle with an abnormality in the ejection direction of ink in the nozzle row (S420), and then the process ends immediately.

===Test Timing===

Examples of the timing at which the ejection test is performed include the followings.

(1) During a Printing Process

The ejection test is performed at an appropriate timing during a printing process. For example, in the case of "bidirectional printing", the carriage 41 moves to the standby position and the ejection test is performed on the nozzles #1 to #180 each time the movement direction is changed. Thus, it is possible to avoid a trouble being caused in a print image due to clogging of the nozzles for example during a printing process.

(2) When the Power is Turned On

The ejection test is performed when the power is turned on. In this case, the ejection test is performed when the power of a printer (printing apparatus) is turned on in order to carry out printing, and the ejection test is performed on the nozzles #1 to #180 as one of the processes that are carried out during initialization of the inkjet printer 1. By performing the ejection test at this timing, a printing process can be carried out smoothly without clogging or the like in the nozzles #1 to #180.

(3) When Supplying Paper

The ejection test is performed at the time of an operation in which the medium S is sent to a predetermined position such that printing is carried out, that is, when supplying paper. In this case, it is checked whether or not ink is properly ejected when a printing process is about to be performed on one medium S, and the ejection test may be performed every time the medium S is supplied, or the ejection test may be performed for every predetermined number of media at an appropriate interval.

(4) When Acquiring Print Data

The ejection test is performed when the inkjet printer 1 receives print data from the computer 140 such as a personal computer. In other words, it is checked whether or not ink is properly ejected when print data is received from the computer 140 and printing is about to be carried out. It is possible to carry out a printing process smoothly without clogging in the nozzles #1 to #180, by performing the ejection test at this timing.

It should be noted that it is not necessarily required that the timing at which the ejection test is performed is the above-described timings (1) to (4), and the ejection test may be performed at a timing other than the timings (1) to (4).

===Summary <No. 1: First Embodiment>===

As described above, according to this embodiment, the plurality of detection members 70 are arranged in the direction that intersects with the arrangement direction of the plurality of nozzles #1 to #180 that are arranged at the head 21, in correspondence with the different nozzles #1 to #180. Thus, it is possible to perform the ejection test on the nozzles #1 to #180 at the same test position at one time. Accordingly, it is possible to efficiently perform the ejection test on the nozzles #1 to #180, so that the time for the test can be shortened.

Furthermore, in this embodiment, the detection members 70 are arranged in the direction that intersects with the arrangement direction of the nozzles #1 to #180. Thus, it is possible to detect, in more detail, misalignment in the carrying direction of the ink droplet Ip ejected from the nozzles #1 to #180. Accordingly, it is possible to prevent "white streaks" from being generated in an image to be printed, in the movement direction of the carriage 41, so that the image quality of a print image can be significantly improved.

Furthermore, in this embodiment, an induced current generated at the detection members 70 with ink ejected from each of the nozzles #1 to #180 is detected. Thus, it is possible to detect not only whether or not ink is ejected from the nozzles #1 to #180 but also the ejection direction of ink from the nozzles #1 to #180.

Furthermore, in this embodiment, the detection members 70 are arranged in parallel to each other. Thus, it is possible to efficiently perform the test on the nozzles #1 to #180.

Furthermore, in this embodiment, the plurality of detection members 70 are electrically connected to each other via the common line 75, and thus the test can be easily performed.

Furthermore, in this embodiment, the judgment is performed by comparing the magnitude of an induced current generated at the detection members 70 with the predetermined reference value, and thus the test can be easily performed.

Furthermore, in this embodiment, a voltage is applied to the detection members 70, and thus ink ejected from the nozzles #1 to #180 can be easily charged.

===Positional Relationship between Ejection Testing Unit and Nozzle Rows <No. 2: Second Embodiment>===

Figure 27:
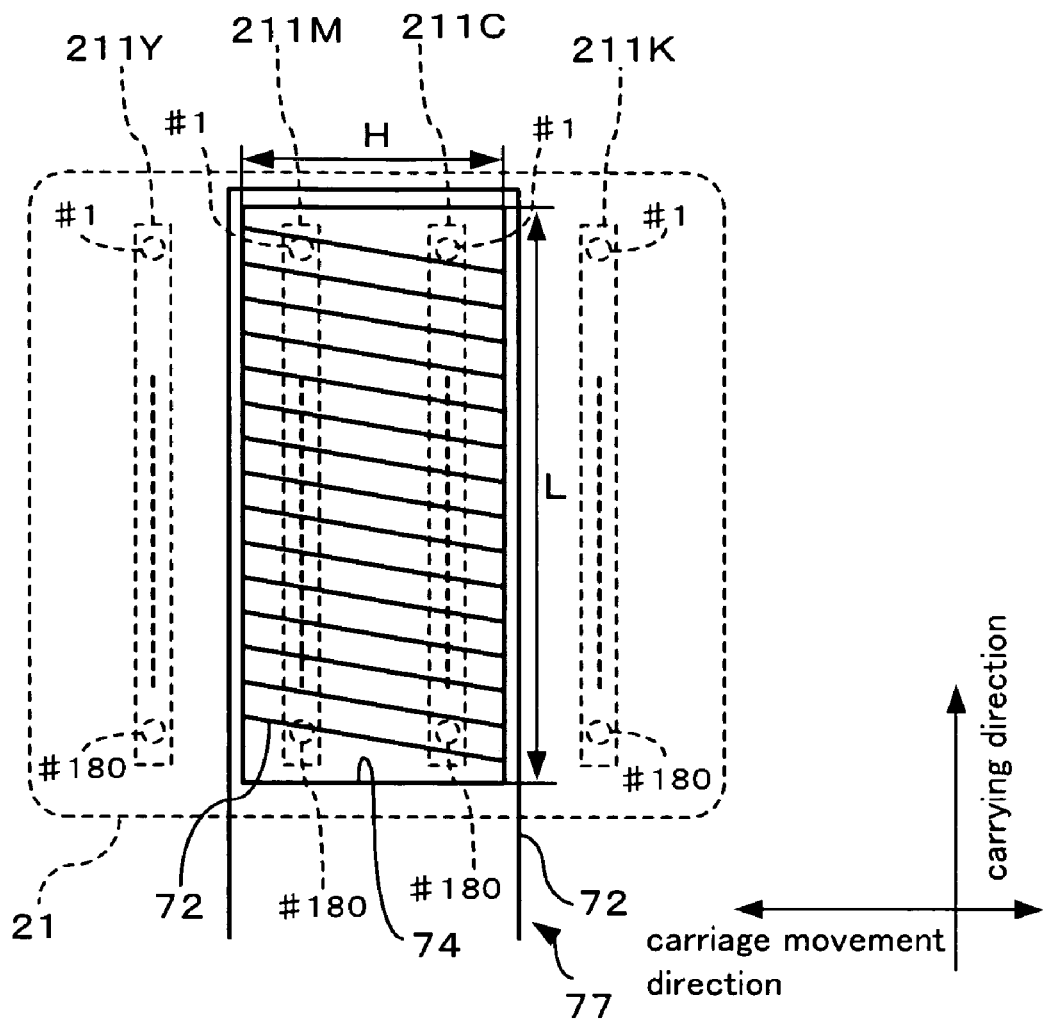
FIG. 27 is a view illustrating another example of the positional relationship between the detection members and the nozzle rows.

FIG. 27 illustrates the positional relationship between the ejection testing unit 77 and the nozzle rows 211C, 211M, 211Y, and 211K when the ejection test is performed.

As shown in FIG. 27, the longitudinal length L of the opening section 74 disposed at the substrate 72 of the ejection testing unit 77 is set in accordance with the lengthwise length of the nozzle rows 211C, 211M, 211Y, and 211K such that the longitudinal length L is slightly longer than the lengthwise length. Furthermore, the lateral length H of the opening section 74 is set so as to correspond to a width of two rows of the nozzle rows 211C, 211M, 211Y, and 211K. More specifically, the opening section 74 has the size at which two nozzle rows among the four nozzle rows 211C, 211M, 211Y, and 211K arranged at the head 21 are completely covered. In other words, the plurality of detection members 70 can be opposed to two nozzle rows among the four nozzle rows 211C, 211M, 211Y, and 211K. Thus, it is possible to perform the ejection test on two nozzle rows in a state where the head 21 is at rest.

The plurality of detection members 70 arranged at the opening section 74 of the ejection testing unit 77 are arranged at an angle in the direction that intersects with the arrangement direction (parallel to the carrying direction in this embodiment) of the nozzles #1 to #180 of the nozzle rows 211C, 211M, 211Y, and 211K, in correspondence with the nozzles #1 to #180 of the nozzle rows 211C, 211M, 211Y, and 211K.

As shown in FIG. 27, when the ejection test is performed, the positional alignment is carried out such that one nozzle row or two nozzle rows (nozzle rows 211M and 211C in this embodiment) among the plurality of nozzle rows 211C, 211M, 211Y, and 211K arranged at the head 21 are positioned directly above the detection members 70. After the positional alignment ends, ink is ejected from the nozzles #1 to #180 of the nozzle rows (nozzle rows 211M and 211C in this embodiment) on which the positional alignment has been carried out toward the gaps between the detection members 70 to perform the ejection test.

The ejection test is performed also on other nozzle rows (nozzle rows 211Y and 211K in this embodiment). More specifically, in the ejection test, the carriage 41 moves such that the ejection test is performed on other nozzle rows 211Y and 211k on which the ejection test has not been performed. Then, the detection members 70 and nozzle rows (such as nozzle rows 211Y and 211K in this embodiment) on which the ejection test is to be performed are positionally aligned, so that the ejection test is performed on the nozzle row 211Y and the nozzle row 211K. In this manner, the ejection test is performed sequentially on the plurality of nozzle rows 211C, 211M, 211Y, and 211K arranged at the head 21.

===Positional Relationship between Detection Members and Nozzles===

Figure 28:
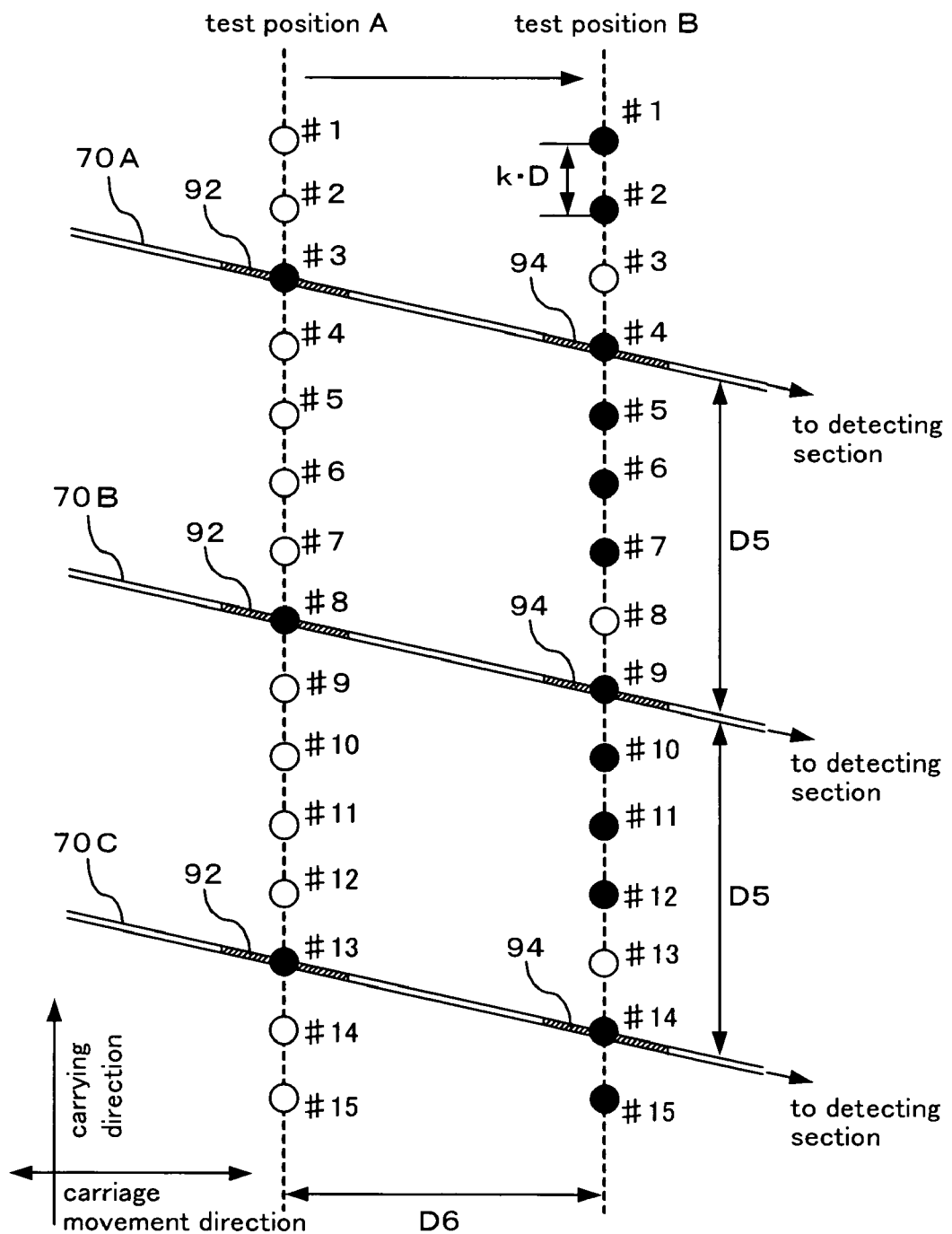
FIG. 28 is a view illustrating another example of the positional relationship between the detection members and the nozzles.

FIG. 28 illustrates an example of the positional relationship between the detection members 70 and the nozzles #1 to #180 in the ejection test. The following is a description concerning an example in which the ejection test is performed on the nozzles #1 to #15 with three detection members 70A, 70B, and 70C. The following is a further description concerning an example in which the ejection test is performed on the nozzles #1 to #15 at two test positions A and B. A spacing D5 in the carrying direction between the detection members 70A, 70B, and 70C is set to a spacing that is substantially equal to five times the nozzle spacing k·D. Furthermore, the test position A and the test position B are arranged with a spacing D6 therebetween.

The test position A is provided such that the ejection test is performed on the nozzles #1, #2, #4, #5 #6, #7, #9, #10, #11, #12, #14, and #15. On the other hand, the test position B is provided such that the ejection test is performed on the nozzles #3, #8, and #13. Here, the nozzles that are to be tested at the test position A or B are represented by white circles "○". Furthermore, the nozzles that are not to be tested at the test position A or B are represented by black circles "●".

The two test positions A and B are changed when the carriage 41 (nozzles #1 to #15) moves in the movement direction of the carriage 41. More specifically, when the nozzles #1 to #180 (nozzles #1 to #15 in this embodiment) arranged at the head 21 of the carriage 41 move relative to the detection members 70A, 70B, and 70C (ejection testing unit 77), the test positions are changed. Herein, first, the ejection test is performed at the test position A. Next, after the carriage 41 has moved, the ejection test is performed at the test position B. In other words, the nozzles #1 to #15 move relatively from the test position A to the test position B in accordance with the movement of the carriage 41.

The reason why the two test positions A and B are arranged is that the positions of the detection members 70A, 70B, and 70C respectively overlap with the positions of the nozzles #3, #8, and #13 at the test position A. When the positions of the detection members 70A, 70B, and 70C respectively overlap with the positions of the nozzles #3, #8, and #13 in this manner, the ink droplet Ip ejected from the nozzles #3, #8, and #13 may be brought into contact with the detection members 70A, 70B, and 70C in the ejection test. When the ink droplet Ip ejected from the nozzles #3, #8, and #13 is brought into contact with the detection members 70A, 70B, and 70C, there is a possibility that a sufficient induced current is not generated at the detection members 70A, 70B, and 70C. When a sufficient induced current is not generated at the detection members 70A, 70B, and 70C in the manner, the ejection test may not be sufficiently performed on the nozzles. Thus, it is preferable that ink ejected from the nozzles that are to be tested is not brought into contact with the detection members 70A, 70B, and 70C to the extent possible. It goes without saying that this does not eliminate cases in which ink ejected from the nozzles that are to be tested comes into contact with the detection members 70A, 70B, and 70C, in the ejection test.

At the test position A, since the nozzles #3, #8, and #13 respectively overlap with the detection members 70A, 70B, and 70C, the nozzles are not to be tested. On the other hand, when the nozzles #1 to #15 move to the test position B in accordance with the movement of the carriage 41, the nozzles #3, #8, and #13 that are not tested at the test position A do not overlap with the detection members 70A, 70B, and 70C. Thus, at the test position B, it is possible to perform the ejection test on the nozzles #3, #8, and #13 that are not tested at the test position A.

At the test position A, the nozzles #1, #2, #4, and #5 correspond to the detection member 70A. Furthermore, the nozzles #6, #7, #9, and #10 correspond to the detection member 70B. Furthermore, the nozzles #11, #12, #14, and #15 correspond to the detection member 70C.

On the other hand, at the test position B, the nozzle #3 corresponds to the detection member 70A. Furthermore, the nozzle #8 corresponds to the detection member 70B. Furthermore, the nozzle #13 corresponds to the detection member 70C.

<Ejection Judgment Method>

A judgment method in the ejection test on the nozzles #1 to #15 is described. Herein, the spacings between the detection members 70A, 70B, and 70C, and the nozzles #1 to #15 corresponding to the detection members 70A, 70B, and 70C are different from each other depending on the nozzles #1 to #15. Thus, even when the ink droplet Ip is properly ejected from the nozzles #1 to #15, the induced current of different magnitudes is generated at the detection members 70A, 70B, and 70C. More specifically, in the case of the nozzles #2, #3, #4, #7, #8, #9, #12, #13, and #14 on which the ejection test is performed at the positions close to the detection members 70A, 70B, and 70C, at the test positions A and B, the magnitude of the induced current generated at the detection members 70A, 70B, and 70C is large. On the other hand, in the case of the nozzles #1, #5, #6, #10, #11, and #15 on which the ejection test is performed at the positions away from the detection members 70A, 70B, and 70C, at the test positions A and B, the magnitude of the induced current generated at the detection members 70A, 70B, and 70C is small.

Thus, in this embodiment, a judgment reference in the ejection test is switched in accordance with the position of the nozzles #1 to #15 that are to be tested. More specifically, the judgment reference is switched between a case in which the test is performed on the nozzles #2, #3, #4, #7, #8, #9, #12, #13, and #14 on which the test is performed at the positions close to the detection members 70A, 70B, and 70C, and a case in which the ejection test is performed on the nozzles #1, #5, #6, #10, #11, and #15 on which the test is performed at the positions away from the detection members 70A, 70B, and 70C.

Figure 29A:
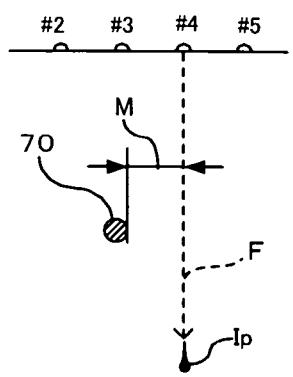
FIG. 29A is an explanatory diagram of an example of a method for judging whether or not ejection is performed, when ink is properly ejected from the nozzle that is close to the detection member in FIG. 28.
Figure 29A:
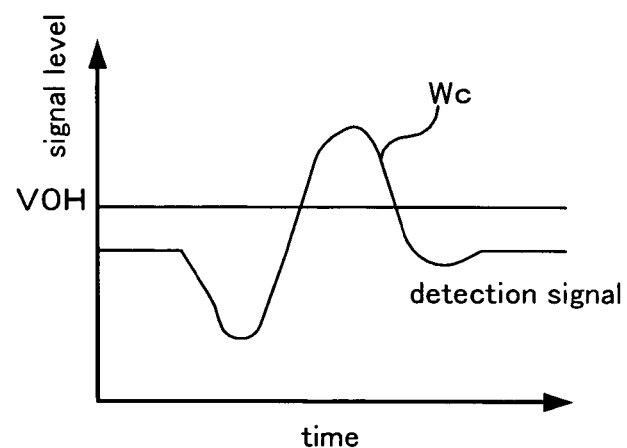
Figure 29B:
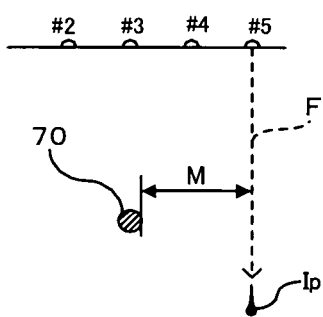
FIG. 29B is an explanatory diagram of an example of a method for judging whether or not ejection is performed, when ink is properly ejected from the nozzle that is away from the detection member in FIG. 28.
Figure 29B:
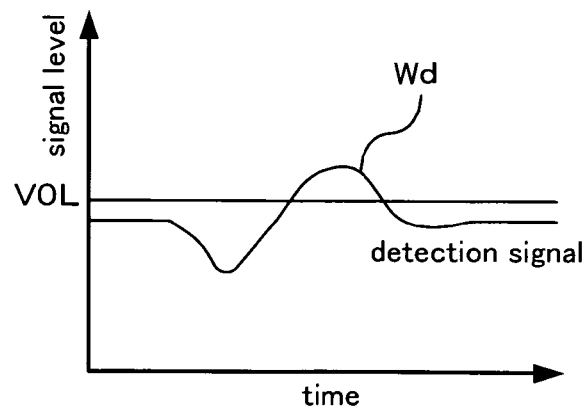

FIGS. 29A and 29B respectively illustrate examples of detection signals that are output from the detecting section 80 when ink is properly ejected from the nozzles #1 to #15 such that the ejection test is performed. FIG. 29A shows an example of the waveform of a detection signal that is output from the detecting section 80 when ink is properly ejected from the nozzles #2, #3, #4, #7, #8, #9, #12, #13, and #14 that are positioned close to the detection members 70A, 70B, and 70C. FIG. 29B shows an example of the waveform of a detection signal that is output from the detecting section 80 when ink is properly ejected from the nozzles #1, #5, #6, #10, #11, and #15 that are positioned away from the detection members 70A, 70B, and 70C.

When ink is properly ejected from the nozzles #2, #3, #4, #7, #8, #9, #12, #13, and #14 on which the test is performed at the positions close to the detection members 70A, 70B, and 70C, a pulse Wc with a large amplitude is generated in the detection signal as shown in FIG. 29A. On the other hand, when ink is properly ejected from the nozzles #1, #5, #6, #10, #11, and #15 on which the test is performed at the positions away from the detection members 70A, 70B, and 70C, a pulse Wd with a small amplitude is generated in the detection signal as shown in FIG. 29B.

In this manner, even when ink is properly ejected, the magnitudes of the pulses Wc and Wd generated in the detection signal from the detecting section 80 are different between a case of the nozzles #2, #3, #4, #7, #8, #9, #12, #13, and #14 on which the test is performed at the positions close to the detection members 70A, 70B, and 70C and a case of the nozzles #1, #5, #6, #10, #11, and #15 on which the test is performed at the positions away from the detection members 70A, 70B, and 70C.

Thus, when the test of whether or not ink is ejected is performed, a reference value serving as the reference when judging whether or not ink is ejected is switched between a case in which the test is performed on the nozzles #2, #3, #4, #7, #8, #9, #12, #13, and #14 on which the test is performed at the positions close to the detection members 70A, 70B, and 70C, and a case in which the test is performed on the nozzles #1, #5, #6, #10, #11, and #15 on which the test is performed at the positions away from the detection members 70A, 70B, and 70C.

Herein, when the test is performed on the nozzles #2, #3, #4, #7, #8, #9, #12, #13, and #14 on which the test is performed at the positions close to the detection members 70A, 70B, and 70C, "V0H" is used as a reference value, for example. On the other hand, when the test is performed on the nozzles #1, #5, #6, #10, #11, and #15 on which the test is performed at the positions away from the detection members 70A, 70B, and 70C, "V0L", which is lower than "V0H", is used as a reference value, for example. Thus, the test of whether or not ink is ejected can be performed as appropriate in accordance with the spacing between the detection members 70A, 70B, and 70C and the nozzles #1 to #15.

Furthermore, when the test of the ejection direction of ink is performed, the reference when judging the ejection direction of ink is switched between a case in which the test is performed on the nozzles #2, #3, #4, #7, #8, #9, #12, #13, and #14 on which the test is performed at the positions close to the detection members 70A, 70B, and 70C, and a case in which the test is performed on the nozzles #1, #5, #6, #10, #11, and #15 on which the test is performed at the positions away from the detection members 70A, 70B, and 70C.

Figure 30A:
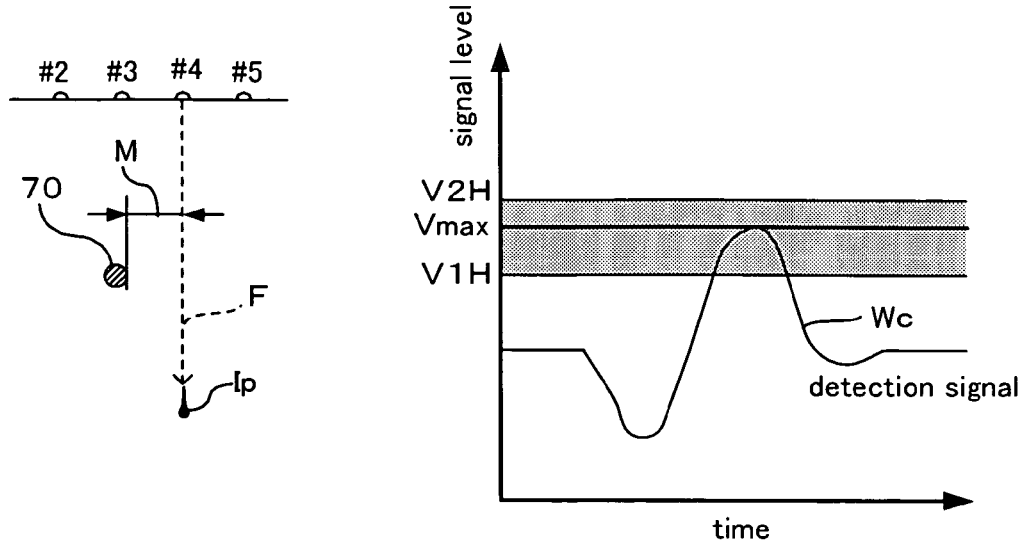
FIG. 30A is an explanatory diagram of an example of a method for judging the ejection direction, when ink is properly ejected from the nozzle that is close to the detection member in FIG. 28.
Figure 30B:
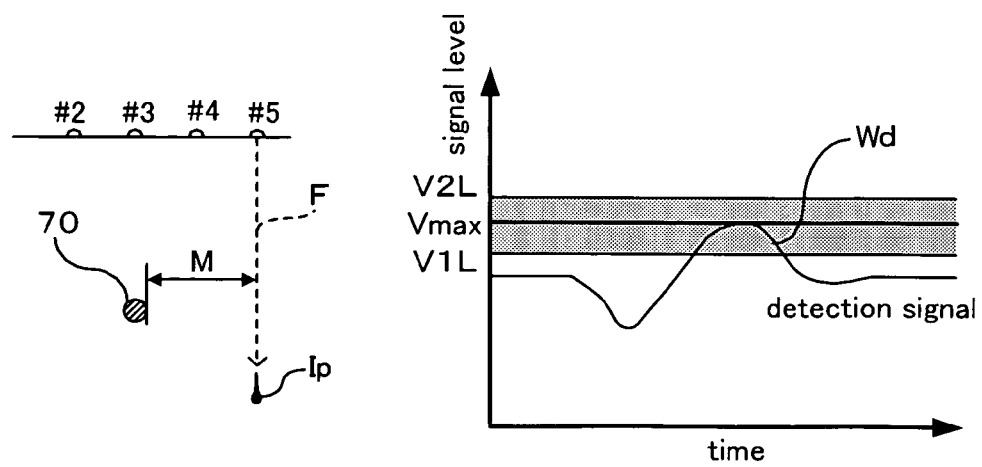
FIG. 30B is an explanatory diagram of an example of a method for judging the ejection direction, when ink is properly ejected from the nozzle that is away from the detection member in FIG. 28.

FIGS. 30A and 30B illustrate the judgment references when the test of the ejection direction of ink is performed. FIG. 30A illustrates the case of the nozzles #2, #3, #4, #7, #8, #9, #12, #13, and #14 on which the test is performed at the positions close to the detection members 70A, 70B, and 70C. FIG. 30B illustrates the case of the nozzles #1, #5, #6, #10, #11, and #15 on which the test is performed at the positions away from the detection members 70A, 70B, and 70C.

As shown in FIG. 30A, when the test is performed on the nozzles #2, #3, #4, #7, #8, #9, #12, #13, and #14 that are positioned close to the detection members 70A, 70B, and 70C, "V1H" is used as a minimum tolerance value and "V2H" is used as a maximum tolerance value. On the other hand, as shown in FIG. 30B, when the test is performed on the nozzles #1, #5, #6, #10, #11, and #15 that are positioned away from the detection members 70A, 70B, and 70C, "V1L" is used as a minimum tolerance value and "V2L" is used as a maximum tolerance value. Thus, the test of the ejection direction of ink can be performed as appropriate in accordance with the spacing between the detection members 70A, 70B, and 70C and the nozzles #1 to #15.

FIG. 30C is a table showing all the reference values, serving as the judgment references in the ejection test, in a case where the test is performed on the nozzles #2, #3, #4, #7, #8, #9, #12, #13, and #14 that are positioned close to the detection members 70A, 70B, and 70C, and in a case where the test is performed on the nozzles #1, #5, #6, #10, #11, and #15 that are positioned away from the detection members 70A, 70B, and 70C.

It should be noted that the reference values "V0H", "V0L", "V1H", "V2H", "V1L", and "V2L", serving as the judgment references in the ejection test, are stored as data in an appropriate storing section, for example, a memory such as the main memory 127. When comparing the signal level of the detection signal with the reference values "V1H", "V1L", "V2H", "V2L", "V0H", and "V0L", the controller 126 acquires information on the reference values "V1H", "V1L", "V2H", "V2L", "V0H", and "V0L" from an appropriate storing section such as the main memory 127.

===Spacing between Test Positions ===

In the inkjet printer according to this embodiment, for the purpose of efficiently performing the test on four nozzle rows, that is, the cyan nozzle row 211C, the magenta nozzle row 211M, the yellow nozzle row 211Y, and the black nozzle row 211K, the spacing D6 between the test position A and the test position B described based on FIG. 28 is set so as to correspond to the spacing Dz (see FIG. 5) between the nozzle rows 211C, 211M, 211Y, and 211K. More specifically, when one nozzle row among the four nozzle rows 211C, 211M, 211Y, and 211K is positioned at the test position A, one of the other nozzle rows is positioned at the test position B. Thus, it is possible to perform the ejection test on two nozzle rows, among the four nozzle rows 211C, 211M, 211Y, and 211K, in a state where the head 21 is at rest at a predetermined position.

The portions of the detection members 70A, 70B, and 70C, opposed to two nozzle rows respectively correspond to "first testing section" and "second testing section". Herein, in FIG. 19, the portions (hatched portions) of the detection members 70A, 70B, and 70C, opposed to the nozzle row with the nozzles #1 to #15 at the test position A correspond to first testing sections 92. Furthermore, in FIG. 19, the portions (hatched portions) of the detection members 70A, 70B, and 70C, opposed to the nozzle row with the nozzles #1 to #15 at the test position B correspond to second testing sections 94.

<Test Method>

Figure 31:
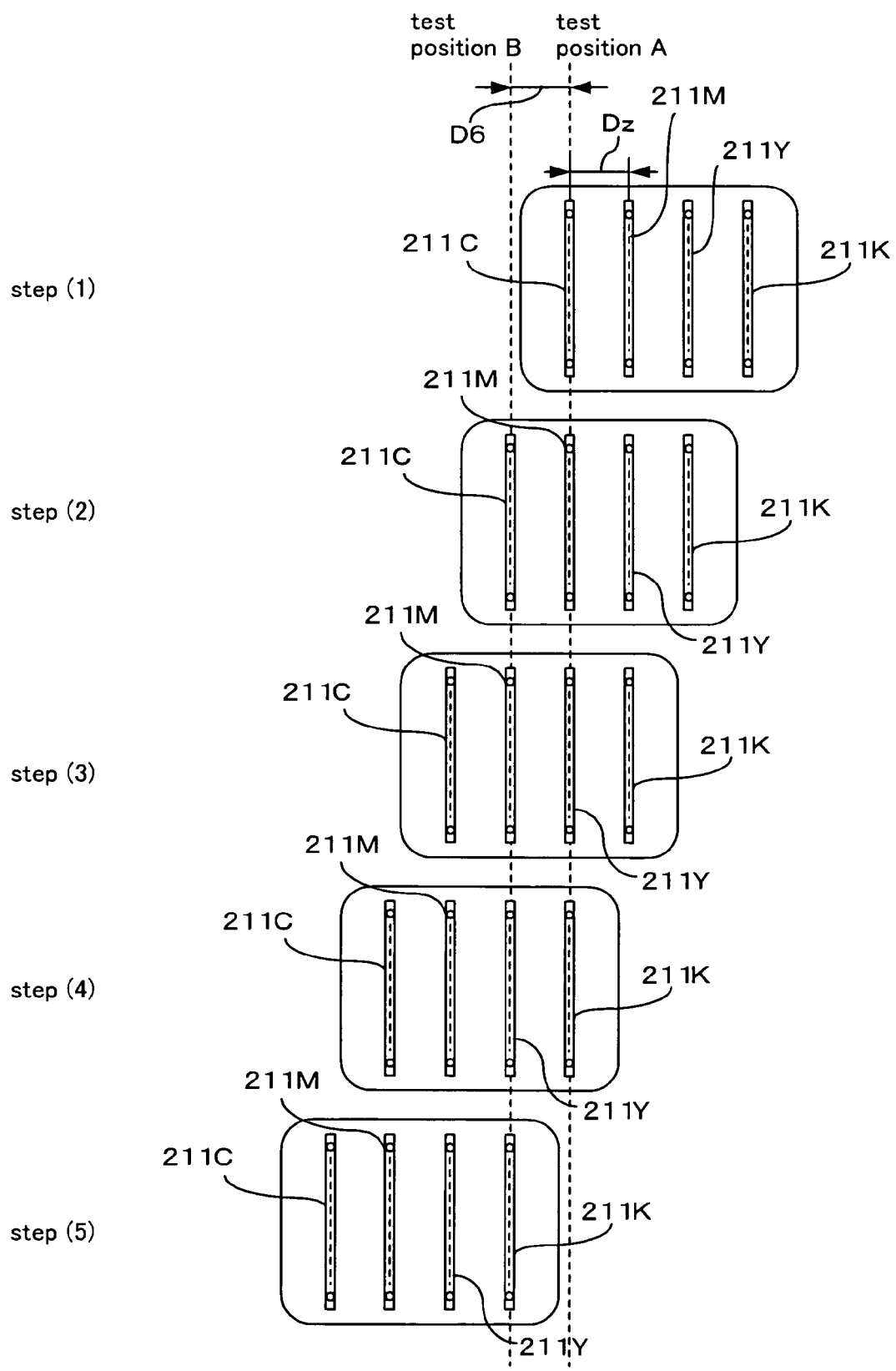
FIG. 31 is a view illustrating an example of a testing procedure for each nozzle row.

FIG. 31 illustrates an example of the testing procedure on the nozzle rows 211C, 211M, 211Y, and 211K in this case. Herein, first, the cyan nozzle row 211C among the four nozzle rows 211C, 211M, 211Y, and 211K is positioned at the test position A in accordance with the movement of the carriage 41 (step (1)). Herein, the test is performed on the cyan nozzle row 211C. The test is performed on the nozzles that do not overlap with the detection members 70.

Then, the carriage 41 again moves, so that the cyan nozzle row 211C is positioned at the test position B (step(2)). Herein, since the spacing D6 between the test position A and the test position B is set so as to correspond to the spacing Dz between the nozzle rows 211C, 211M, 211Y, and 211K, when the cyan nozzle row 211C is positioned at the test position B, the magenta nozzle row 211M is automatically positioned at the test position A. Thus, it is possible to perform the test on both of the cyan nozzle row 211C and the magenta nozzle row 211M in a state where the carriage 41 (head 21) is at rest. Herein, with respect to the cyan nozzle row 211C, the test is performed on the nozzles that are not tested at the test position A. On the other hand, with respect to the magenta nozzle row 211M, the test is performed on the nozzles that do not overlap with the detection members 70. It should be noted that the position at which the head 21 is at rest herein corresponds to "predetermined position".

Then, the carriage 41 again moves, so that the magenta nozzle row 211M is positioned at the test position B (step (3)). Thus, the yellow nozzle row 211Y is automatically positioned at the test position A. Accordingly, it is possible to perform the test on the magenta nozzle row 211M and the yellow nozzle row 211Y. With respect to the magenta nozzle row 211M, the test is performed on the nozzles that are not tested at the test position A. On the other hand, with respect to the yellow nozzle row 211Y, the test is performed on the nozzles that do not overlap with the detection members 70. It should be noted that the position at which the head 21 is at rest herein corresponds to "predetermined position".

Then, the carriage 41 further moves, so that the yellow nozzle row 211Y is positioned at the test position B (step (4)). Thus, the black nozzle row 211K is automatically positioned at the test position A. Accordingly, it is possible to perform the test on both of the yellow nozzle row 211Y and the black nozzle row 211K. With respect to the yellow nozzle row 211Y, the test is performed on the nozzles that are not tested at the test position A. On the other hand, with respect to the black nozzle row 211K, the test is performed on the nozzles that do not overlap with the detection members 70. It should be noted that the position at which the head 21 is at rest herein corresponds to "predetermined position".

Then, the carriage 41 again moves, so that the black nozzle row 211K is positioned at the test position B (step (5)). Herein, with respect to the black nozzle row 211K, the test is performed on the nozzles that are not tested at the test position A. At that point, the ejection test on all of the nozzle rows 211C, 211M, 211Y, and 211K ends.

<Testing Procedure>

Figure 32:
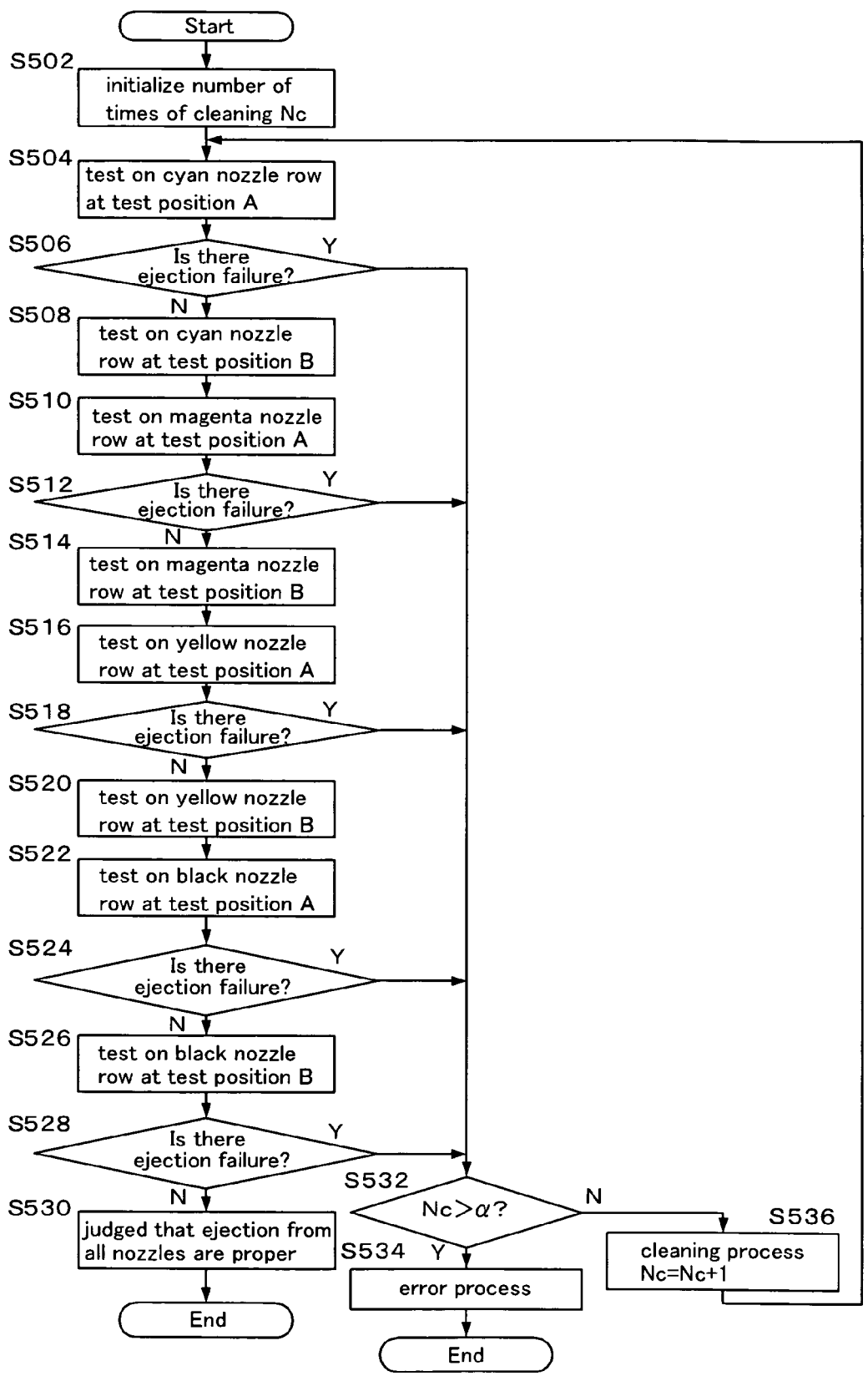
FIG. 32 is a flowchart illustrating an example of a testing method.

FIG. 32 is a flowchart illustrating an example of the procedure of the test performed in this embodiment. The test performed in this embodiment is carried out by the controller 126.

First, the controller 126 initializes a number Nc of times of cleaning (S502). In this step, a counter for counting the number of times of cleaning process is set to 0. Then, the controller 126 moves the carriage 41, so that the cyan nozzle row 211C is positioned at the test position A, and performs the ejection test on the cyan nozzle row 211C (S504). After the test, the controller 126 checks whether or not there is an ejection failure at the tested nozzles (S506).

Here, if there is an ejection failure at the tested nozzles, then the procedure proceeds to step S532, where the controller 126 checks whether or not the number Nc of times of cleaning up to this point is not larger than a prescribed number a. Here, the prescribed number α is a number at which it is not conceivable that ejection will be restored even if a cleaning process is repeated more than this number. If the number Nc of times of cleaning is larger than the prescribed number α, then the procedure proceeds step S534, where the controller 126 performs the error process to end the procedure. On the other hand, if the number Nc of times of cleaning is not larger than the prescribed number α, then the procedure proceeds step S536, where the controller 126 performs the cleaning process. Herein, the cleaning process refers to a process in which ink is pumped from the nozzles with the pump device 31, a process in which ink is forcibly evacuated from the nozzles, or a process in which the opening sections of the nozzle are wiped, for example. When the prescribed number α is three, if the number Nc of times of cleaning is four or larger, then the error process is performed (S534), and if the number is three or smaller, then the cleaning process is performed (S536). After the cleaning process has been performed, the controller 126 adds one to the number Nc of times of cleaning. Then, the procedure returns to step S504, where the controller 126 again performs the test from the beginning.

On the other hand, if there is no ejection failure at the tested nozzles, then the controller 126 moves the carriage 41, so that the cyan nozzle row 211C is positioned at the test position B and the magenta nozzle row 211M is positioned at the test position A. Then, the ejection test is performed on the cyan nozzle row 211C (S508). Furthermore, the controller 126 performs the ejection test also on the magenta nozzle row 211M at the test position A (S510). Then, the controller 126 checks whether or not there is an ejection failure at the tested nozzles (S512).

Here, if there is an ejection failure at the tested nozzles, then the procedure proceeds to step S532, where the controller 126 checks the number Nc of times of cleaning up to this point. Herein, if the number is larger than the prescribed number α, then the controller 126 performs the error process (S534), and then the process ends. On the other hand, if the number is not larger than the prescribed number α, then the controller 126 performs the cleaning process (S536) and adds one to the number Nc of times of cleaning. Then, the procedure returns to step S504, where the test is again performed from the beginning.

On the other hand, if there is no ejection failure at the tested nozzles, then the controller 126 moves the carriage 41, so that the magenta nozzle row 211M is positioned at the test position B and the yellow nozzle row 211Y is positioned at the test position A. Then, the controller 126 performs the ejection test on the magenta nozzle row 211M (S514), and performs the ejection test also on the yellow nozzle row 211Y at the test position A (S516). Then, the controller 126 checks whether or not there is an ejection failure at the tested nozzles (S518).

Here, if there is an ejection failure at the tested nozzles, then the procedure proceeds to step S532, where the controller 126 checks the number Nc of times of cleaning up to this point. Herein, if the number is larger than the prescribed number α, then the error process is performed (S534), and then the process ends. On the other hand, if the number is not larger than the prescribed number α, then the controller 126 performs the cleaning process (S536) and adds one to the number Nc of times of cleaning. Then, the procedure returns to step S504, where the test is again performed from the beginning.

If there is no ejection failure at the tested nozzles, then the controller 126 moves the carriage 41, so that the yellow nozzle row 211Y is positioned at the test position B, and performs the ejection test on the yellow nozzle row 211Y (S520). Furthermore, the controller 126 performs the ejection test also on the black nozzle row 211K at the test position A (S522). Then, the controller 126 checks whether or not there is an ejection failure on the tested nozzles (S524). If there is an ejection failure on the tested nozzles, then the controller 126 performs the above-described processes (S532 to S536).

On the other hand, if there is no ejection failure at the tested nozzles, then the controller 126 moves the carriage 41, so that the black nozzle row 211K is positioned at the test position B, and performs the ejection test on the black nozzle row 211K (S526). Then, it is checked whether or not there is an ejection failure on the tested nozzles (S528). If there is an ejection failure on the tested nozzles, then the controller 126 performs the above-described processes (S532 to S536). On the other hand, if there is no ejection failure at the tested nozzles, then it is judged that there is no ejection failure at any nozzle row (S530). Subsequently, the controller 126 ends the process.

<Judging Process>

Figure 33:
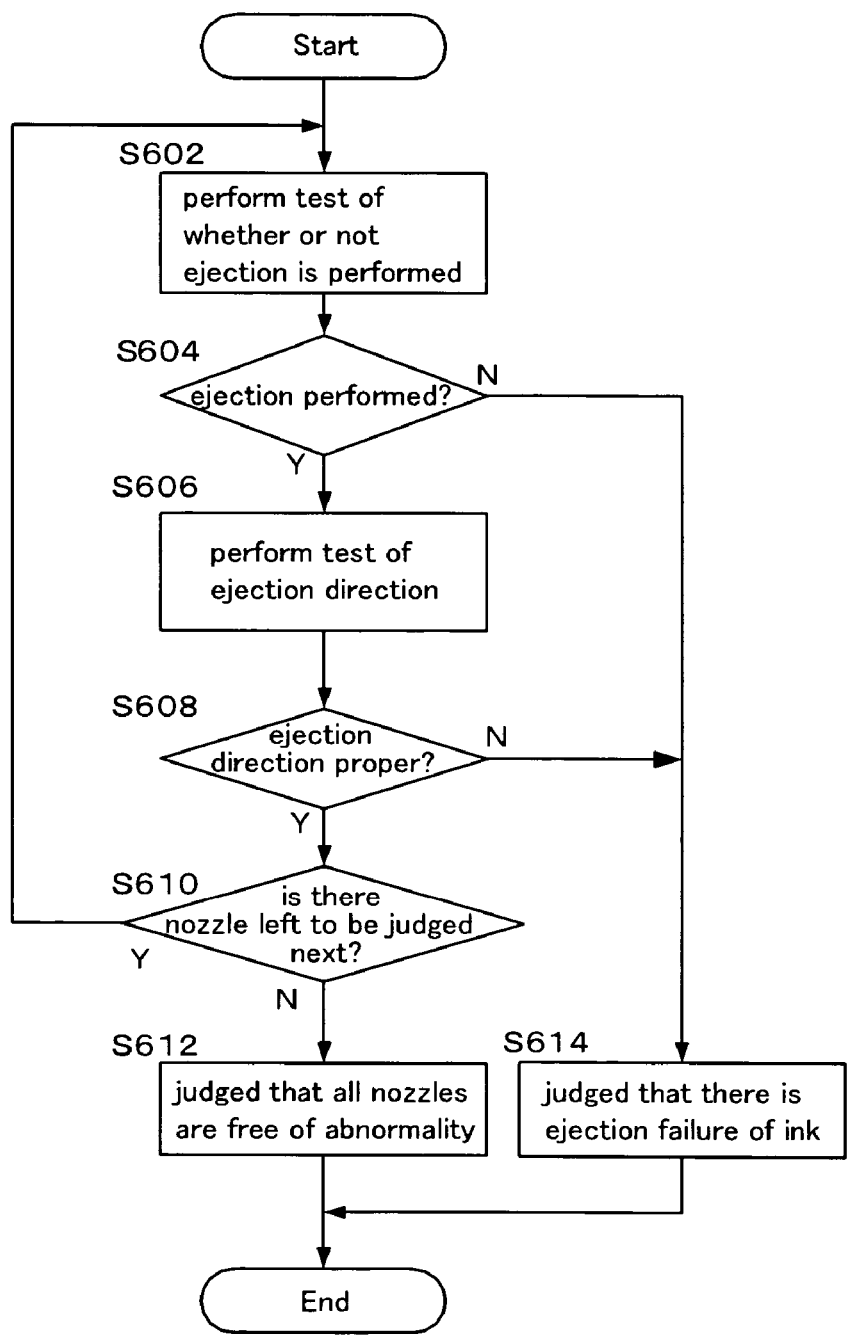
FIG. 33 is a flowchart illustrating an example of an ejection judging procedure for each nozzle when testing.

FIG. 33 is a flowchart illustrating an example of the judging procedure performed by the controller 126. The controller 126 performs the test of whether or not ejection is performed from a first nozzle (S602). The test is performed using the method described based on FIGS. 12, 29A and 29B, for example. Then, the controller 126 judges whether or not ejection is performed from the nozzle (S604). If the results of the judgment are that ejection is not performed from the nozzle, then the procedure proceeds to step S614, where the controller 126 determines that there is an ejection failure of ink (S614). Subsequently, the controller 126 ends the process.

On the other hand, if it is judged that ejection is performed from the nozzle, then the procedure proceeds to step S606, where the controller 126 performs the test of the ejection direction from the nozzle (S606). The test is performed using the method described based on FIGS. 13, 14A, 14B, 14C, 28A, and 28B, for example. Then, the controller 126 judges whether or not the ejection direction is proper (S608). If the results of the judgment are that the ejection direction from the nozzle is not proper, then the procedure proceeds to step S614, where the controller 126 determines that there is an ejection failure of ink (S614). Subsequently, the controller 126 ends the process.

On the other hand, if it is judged that the ejection direction from the nozzle is proper, then the procedure proceeds to step S610, where the controller 126 checks whether or not there is a further nozzle left to be judged next (S610). If there is a further nozzle left to be judged next, then the procedure returns to step S602, where the controller 126 performs the judgment on the nozzles on which the judgment has not been performed. On the other hand, if there is no further nozzle left to be judged next, then the controller 126 determines that the test on all nozzles that are to be judged has ended, the procedure proceeds to step S612, where it is judged that all nozzles are free of abnormality (S612). Subsequently, the controller 126 immediately ends the process.

===Other Embodiments===

Figure 34:
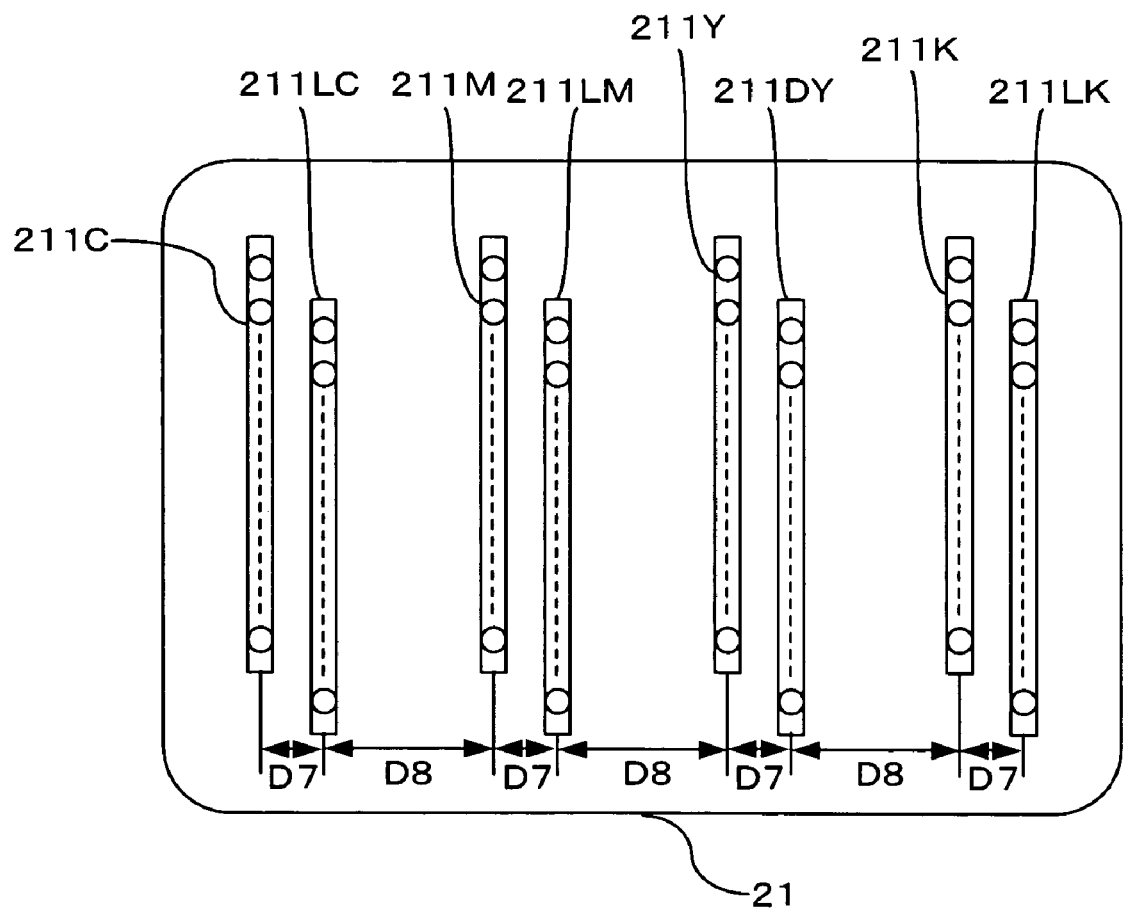
FIG. 34 is a view illustrating an arrangement example of other nozzle rows.

FIG. 34 illustrates another embodiment of the nozzle rows. In this embodiment, as the nozzle rows, the head 21 is provided with a light cyan nozzle row 211LC, a light magenta nozzle row 211LM, a dark yellow nozzle row 211DY, a light black nozzle row 211LK, in addition to the cyan nozzle row 211C, the magenta nozzle row 211M, the yellow nozzle row 211Y, and the black nozzle row 211K. Herein, the light cyan nozzle row 211LC is constituted by a plurality of nozzles that eject ink of light cyan (LC). Furthermore, the light magenta nozzle row 211LM is constituted by a plurality of nozzles that eject ink of light magenta (LM). Furthermore, the dark yellow nozzle row 211DY is constituted by a plurality of nozzles that eject ink of dark yellow (DY), which is darker than yellow (Y).

Furthermore, the light black nozzle row 211LK is constituted by a plurality of nozzles that eject ink of light black (LK), which is lighter than black (K). The light cyan nozzle row 211LC, the light magenta nozzle row 211LM, the dark yellow nozzle row 211DY, the light black nozzle row 211LK are arranged at the positions slightly shifted in the carrying direction from the cyan nozzle row 211C, the magenta nozzle row 211M, the yellow nozzle row 211Y, and the black nozzle row 211K.

Each of a spacing between the cyan nozzle row 211C and the light cyan nozzle row 211LC, a spacing between the magenta nozzle row 211M and the light magenta nozzle row 211LM, a spacing between the yellow nozzle row 211Y and the dark yellow nozzle row 211DY, and a spacing between the black nozzle row 211K and the light black nozzle row 211LK is set to D7. Furthermore, each of a spacing between the light cyan nozzle row 211LC and the magenta nozzle row 211M, a spacing between the light magenta nozzle row 211LM and the yellow nozzle row 211Y, and a spacing between the dark yellow nozzle row 211DY and the black nozzle row 211K is set to D8.

<Test Method>

Figure 35A:
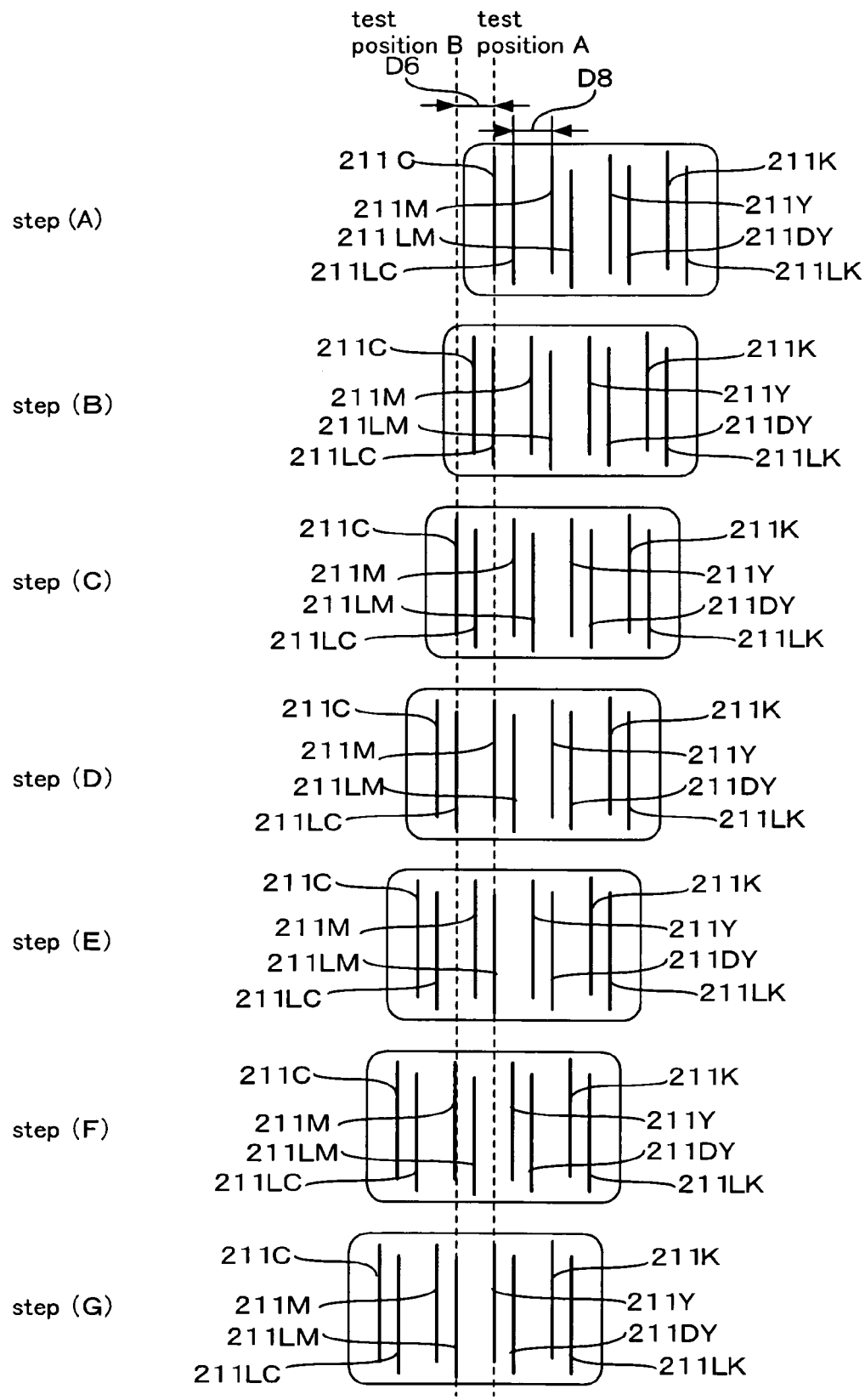
FIG. 35A is an explanatory diagram <No. 1> of an example of a testing procedure in the arrangement of the nozzle rows in FIG. 34.
Figure 35B:
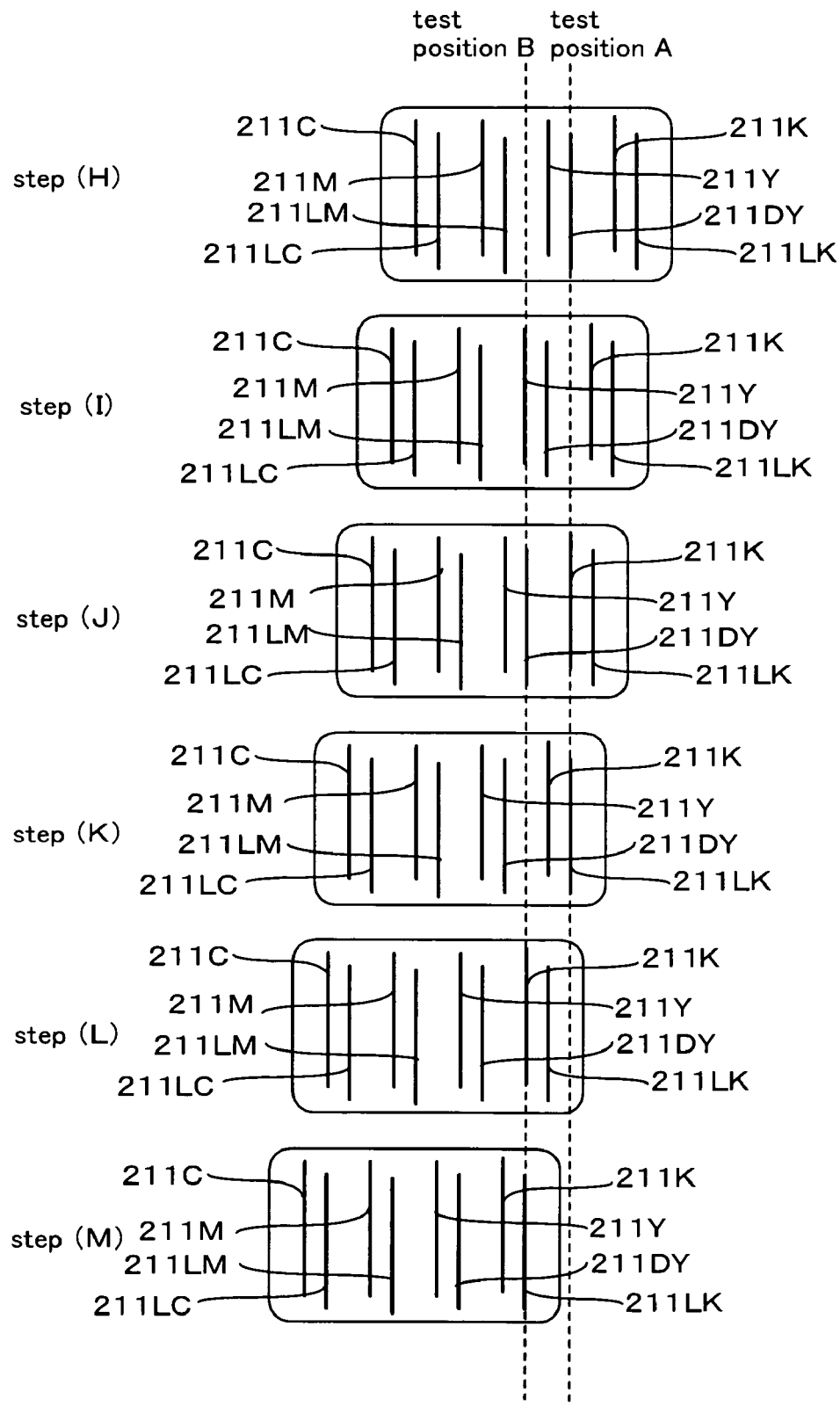
FIG. 35B is an explanatory diagram <No. 2> of an example of a testing procedure in the arrangement of the nozzle rows in FIG. 34.

FIGS. 35A and 35B illustrate an example of the testing procedure on the nozzle rows 211C, 211LC, 211M, 211LM, 211Y, 211DY, 211K, and 211LK in this case.

First, as shown in FIG. 35A, the cyan nozzle row 211C is positionally aligned at the test position A in accordance with the movement of the carriage 41 (step (A)). Herein, the test is performed on the cyan nozzle row 211C. This test is performed on the nozzles that do not overlap with the detection members 70. Then, the carriage 41 moves, so that the light cyan nozzle row 211LC is positionally aligned at the test position A (step (B)). Then, the test is performed on the light cyan nozzle row 211LC. Herein, the test is performed on the nozzles that do not overlap with the detection members 70.

Then, the carriage 41 again moves, so that the cyan nozzle row 211C is positionally aligned at the test position B (step (C)). Herein, the test is performed on the cyan nozzle row 211C. This test is performed on the nozzles that are not tested at the test position A. Then, the carriage 41 again moves, so that the light cyan nozzle row 211LC is positioned at the test position B (step (D)). Herein, since the spacing D6 between the test position A and the test position B corresponds to the spacing D8 between the light cyan nozzle row 211LC and the magenta nozzle row 211M, when the light cyan nozzle row 211LC is positioned at the test position B, the magenta nozzle row 211M is automatically positioned at the test position A. Thus, it is possible to perform the test on both of the light cyan nozzle row 211LC and the magenta nozzle row 211M in a state where the carriage 41 (head 21) is at rest. Herein, with respect to the light cyan nozzle row 211LC, the test is performed on the nozzles that are not tested at the test position A. On the other hand, with respect to the magenta nozzle row 211M, the test is performed on the nozzles that do not overlap with the detection members 70. It should be noted that the position at which the head 21 is at rest herein corresponds to "predetermined position".

Then, the light magenta nozzle row 211LM is positioned at the test position A in accordance with the movement of the carriage 41 (step (E)). Herein, with respect to the light magenta nozzle row 211LM, the test is performed on the nozzles that do not overlap with the detection members 70. The carriage 41 further moves, so that the magenta nozzle row 211M is positioned at the test position B (step (F)). Herein, with respect to the magenta nozzle row 211M, the test is performed on the nozzles that are not tested at the test position A.

Then, the carriage 41 moves, so that the light magenta nozzle row 211LM is positioned at the test position B (step (G)). Herein, since the spacing D8 between the light magenta nozzle row 211LM and the yellow nozzle row 211Y corresponds to the spacing D6 between the test position A and the test position B, the yellow nozzle row 211Y is positioned at the test position B. Thus, it is possible to perform the test on both of the light magenta nozzle row 211LM and the yellow nozzle row 211Y. In this case, with respect to the light magenta nozzle row 211LM, the test is performed on the nozzles that are not tested at the test position A. On the other hand, with respect to the yellow nozzle row 211Y, the test is performed on the nozzles that do not overlap with the detection members 70. It should be noted that the position at which the head 21 is at rest herein corresponds to "predetermined position".

Next, as shown in FIG. 35B, the dark yellow nozzle row 211DY is positioned at the test position A in accordance with the movement of the carriage 41 (step (H)). Herein, with respect to the dark yellow nozzle row 211DY, the test is performed on the nozzles that do not overlap with the detection members 70. The carriage 41 further moves, so that the yellow nozzle row 211Y is positioned at the test position B (step (I)). Herein, with respect to the yellow nozzle row 211Y, the test is performed on the nozzles that are not tested at the test position A.

Then, the carriage 41 further moves, so that the dark yellow nozzle row 211DY is positioned at the test position B (step (J)). Herein, since the spacing D8 between the dark yellow nozzle row 211DY and the black nozzle row 211K corresponds to the spacing D6 between the test position A and the test position B, the black nozzle row 211K is positioned at the test position A. Thus, it is possible to perform the test on both of the dark yellow nozzle row 211DY and the black nozzle row 211K. In this case, with respect to the dark yellow nozzle row 211DY, the test is performed on the nozzles that are not tested at the test position A. On the other hand, with respect to the black nozzle row 211K, the test is performed on the nozzles that do not overlap with the detection members 70. It should be noted that the position at which the head 21 is at rest herein corresponds to "predetermined position".

The carriage 41 further moves, so that the light black nozzle row 211LK is positioned at the test position A (step (K)). Herein, with respect to the light black nozzle row 211LK, the test is performed on the nozzles that do not overlap with the detection members 70. Then, the carriage 41 again moves, so that the black nozzle row 211K is positioned at the test position B (step (L)). Herein, with respect to the black nozzle row 211K, the test is performed on the nozzles that are not tested at the test position A.

Lastly, the light black nozzle row 211LK is positioned at the test position B in accordance with the movement of the carriage 41 (step (M)). Herein, with respect to the light black nozzle row 211LK, the test is performed on the nozzles that are not tested at the test position A.

With the above-described procedure, the ejection test is performed on six nozzle rows, that is, the cyan nozzle row 211C, the magenta nozzle row 211M, the yellow nozzle row 211Y, the black nozzle row 211K, the light cyan nozzle row 211LC, the light magenta nozzle row 211LM, the dark yellow nozzle row 211DY, the light black nozzle row 211LK.

===Test Timing===

Examples of the timing at which the ejection test is performed include the timings (1) to (4) described above, that is, (1) during a printing process, (2) when the power is turned on, (3) when supplying paper, and (4) when acquiring print data.

It should be noted that it is not necessarily required that the timing at which the ejection test is performed is the above-described timings (1) to (4), and the ejection test may be performed at a timing other than the timings (1) to (4).

===Summary <No. 2: Second Embodiment>===

As described above, according to this embodiment, the plurality of testing sections, that is, the first testing sections 92 and the second testing sections 94, that test whether or not ink is properly ejected from the nozzles #1 to #180 of the opposed nozzle rows 211C, 211M, 211Y, 211K (light cyan nozzle row 211LC, light magenta nozzle row 211LM, dark yellow nozzle row 211DY, and light black nozzle row 211LK) are provided. The plurality of testing sections 92 and 94 are arranged with the spacing D6 there between in the movement direction of the carriage 41. The spacing D6 corresponds to the spacing Dz (spading D8) between the plurality of nozzle rows 211C, 211M, 211Y, 211K (light cyan nozzle row 211LC, light magenta nozzle row 211LM, dark yellow nozzle row 211DY, and light black nozzle row 211LK) that are arranged at the head 21. Thus, when the head 21 is stopped at the predetermined position, it is possible to perform the test on the plurality of nozzle rows 211C, 211M, 211Y, 211K (light cyan nozzle row 211LC, light magenta nozzle row 211LM, dark yellow nozzle row 211DY, and light black nozzle row 211LK) in a state where the head 21 is at rest. Accordingly, it is possible to efficiently perform the test on the nozzle rows 211C, 211M, 211Y, 211K (light cyan nozzle row 211LC, light magenta nozzle row 211LM, dark yellow nozzle row 211DY, and light black nozzle row 211LK), so that the time for the test can be shortened.

===Third Testing Section===

Furthermore, a third testing section may be provided in addition to the first testing sections 92 and the second testing sections 94. As the first testing sections 92 and the second testing sections 94, the third testing section tests whether or not ink is properly ejected from the nozzles #1 to #180 of the nozzle rows 211C, 211M, 211Y, 211K (light cyan nozzle row 211LC, light magenta nozzle row 211LM, dark yellow nozzle row 211DY, and light black nozzle row 211LK). In this case, it is preferable that the third testing section is disposed with a spacing from the first testing sections 92 and the second testing sections 94, in the movement direction of the carriage 41.

Furthermore, it is preferable that the spacing between the third testing section and the first testing sections 92 or the second testing sections 94 corresponds to the spacing Dz (spading D8) between the nozzle rows 211C, 211M, 211Y, 211K (light cyan nozzle row 211LC, light magenta nozzle row 211LM, dark yellow nozzle row 211DY, and light black nozzle row 211LK). When the spacing between the third testing section and the first testing sections 92 or the second testing sections 94 corresponds to the spacing Dz (spading D8) in this manner, it is possible to efficiently perform the test on the nozzle rows 211C, 211M, 211Y, 211K (light cyan nozzle row 211LC, light magenta nozzle row 211LM, dark yellow nozzle row 211DY, and light black nozzle row 211LK) as the first testing sections 92 and the second testing sections 94.

It should be noted that the third testing section may be provided at only one location, or two or more locations.

===Other Configuration Examples of Liquid-ejection Testing Device===

<No. 1: Utilization of Frictional Electrification>

Figure 36A:
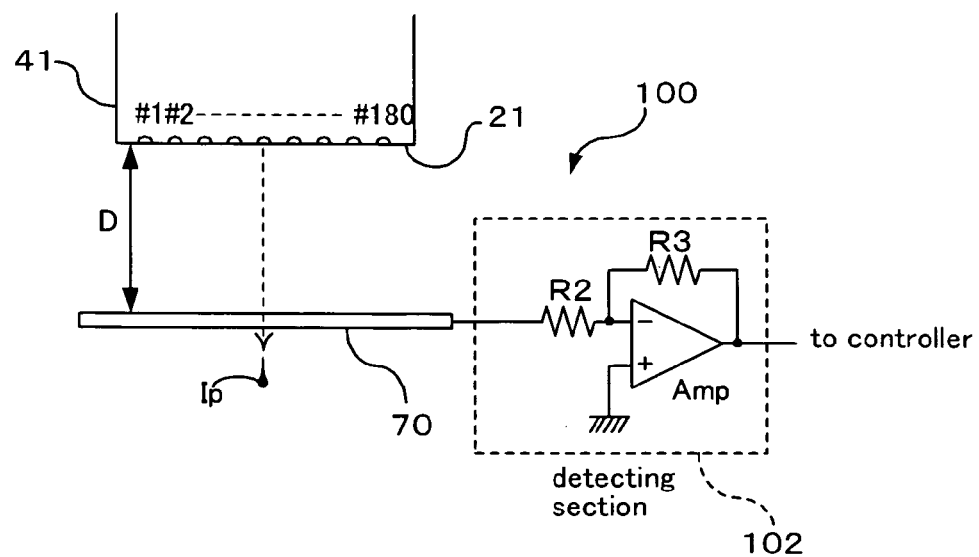
FIG. 36A is a diagram <No. 1> illustrating another embodiment of a liquid-ejection testing device.

FIG. 36A illustrates another configuration example of the liquid-ejection testing device according to the present invention. As shown in FIG. 36A, a liquid-ejection testing device 100 charges the ink droplet Ip by utilizing so-called frictional electrification in which the ink droplet Ip ejected from the nozzles #1 to #180 is naturally charged when parting from the nozzles #1 to #180, instead of charging the ink droplet Ip ejected from the nozzles #1 to #180 by applying a high voltage to the detection members 70 at which an induced current is generated, as in the above-described liquid-ejection testing device (see FIG. 9). Thus, the configuration for applying a high voltage to the detection members 70 in order to charge the ink droplet Ip has been omitted.

When the ink droplet Ip ejected from the nozzles #1 to #180 is charged utilizing frictional electrification in this manner, it is possible to further simplify the configuration of the liquid-ejection testing device 100.

It should be noted that since a high voltage is not applied to the detection members 70 in this embodiment, a detecting section 102 that detects an induced current generated at the detection members 70 has a configuration in which the capacitor C is removed from the configuration of the detecting section 80 in the above-described liquid-ejection testing device 60 (see FIG. 9).

<No. 2: Arrangement of Electrode Section>

Figure 36B:
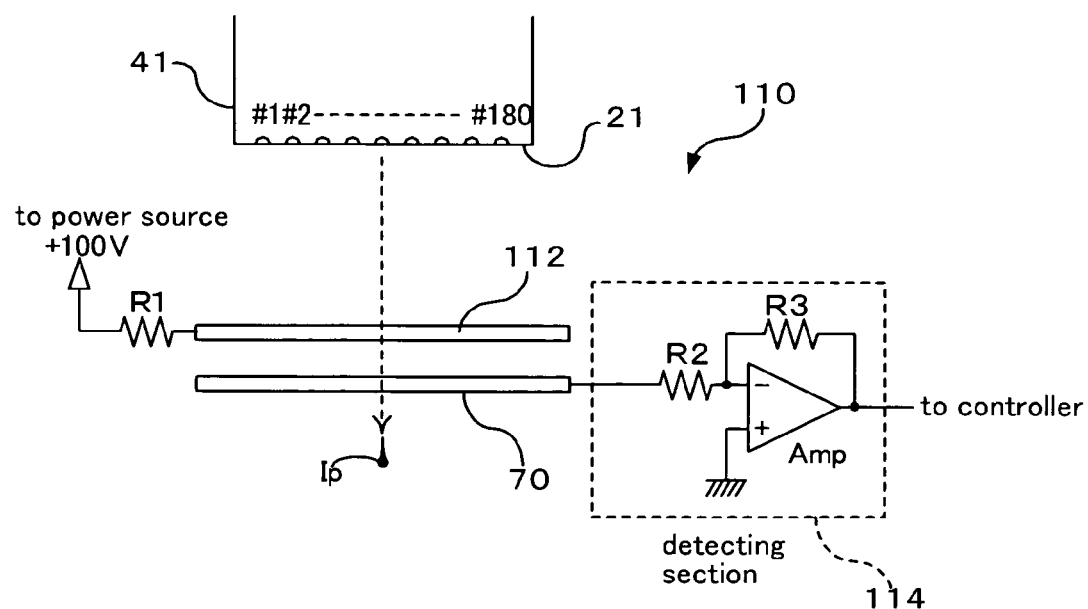
FIG. 36B is a diagram <No. 2> illustrating a liquid-ejection testing device according to another embodiment.

FIG. 36B illustrates another configuration example of the liquid-ejection testing device according to the present invention. As shown in FIG. 36B, a liquid-ejection testing device 110 is provided with an electrode section 112 in addition to the detection members 70, and the ink droplet Ip ejected from the nozzles #1 to #180 is charged by the electrode section 112. As shown in FIG. 36B, the electrode section 112 is made of a conductive wire material such as metal, and is disposed in parallel to the head 21 in such a manner that the electrode section 112 is stretched in tension, as the detection members 70. A power source (not shown) is connected via the protective resistance R1 to the electrode section 112, so that a high voltage such as 100 V (volt) is applied from the power source.

Since this electrode section 112 is provided, an electric field is formed between the head 21 and the electrode section 112, so that the ink droplet Ip can be charged when parting from the nozzles #1 to #180.

It should be noted that since a high voltage is not applied to the detection members 70 also in this case, as in the case of <No. 1> described above, a detecting section 114 that detects an induced current generated at the detection members 70 has a configuration in which the capacitor C is removed from the configuration of the detecting section 80 in the above-described liquid-ejection testing device 60 (see FIG. 9).

Furthermore, it is preferable that the electrode section 112 is disposed as close to the head 21 as possible. As the electrode section 112 is closer to the head 21, the electric field between the electrode section 112 and the head 21 becomes stronger, and thus an induced current is generated even more easily at the detection members 70.

<No. 3: Other Embodiments of Detection Members>

Figure 37A:
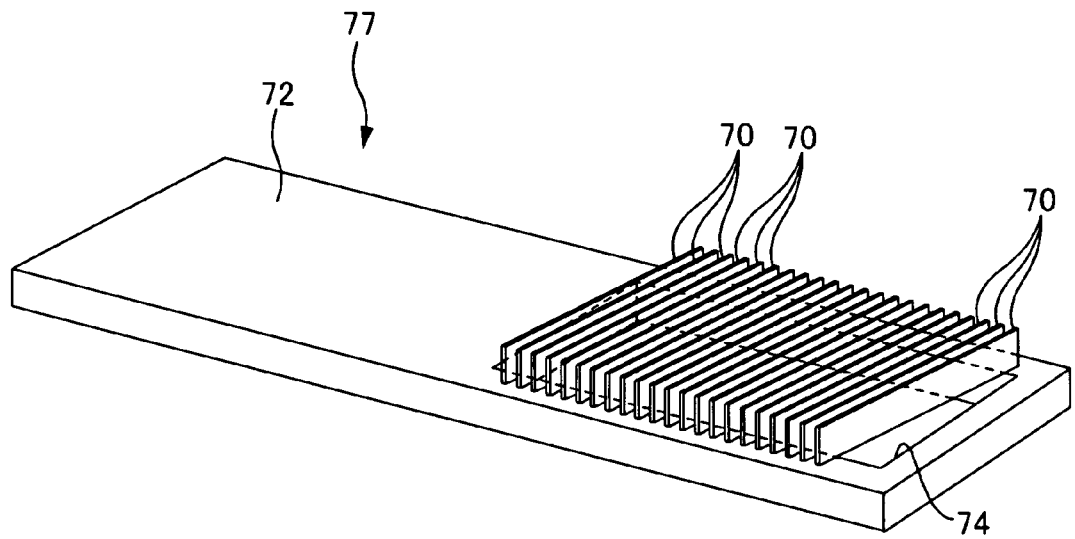
FIG. 37A is a perspective view illustrating another embodiment of detection members.
Figure 37B:
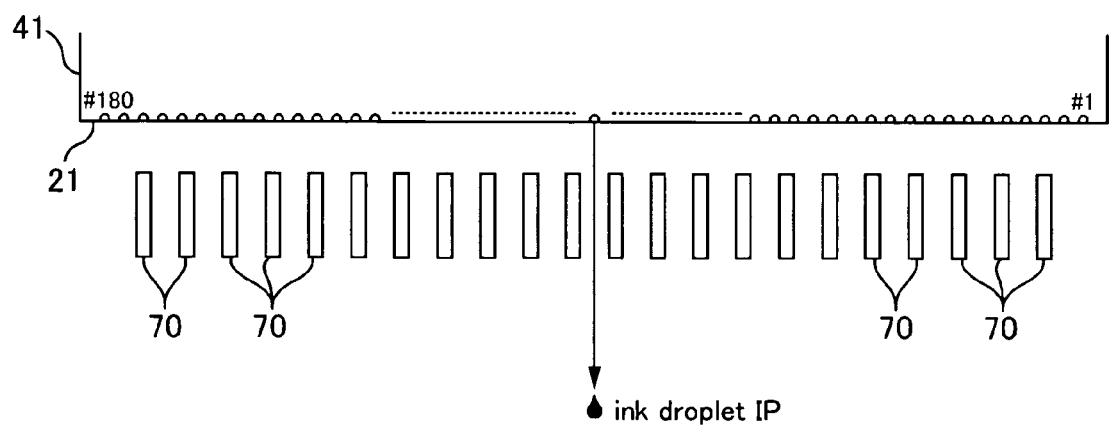
FIG. 37B is a lateral view illustrating another embodiment of detection members.

FIGS. 37A and 37B illustrate another embodiment of the detection members 70. FIG. 37A shows the ejection testing unit 77 in which the detection members 70 are arranged. FIG. 37B illustrates how the test is performed with the detection members 70.

As shown in FIG. 37A, each of the detection members 70 is made of a plate-shaped member. The thickness of each of the plate-shaped detection members 70 is set to about 0.2 mm in this embodiment. Furthermore, the height of each of the plate-shaped detection members 70 is set to about 3 mm in this embodiment. The plate-shaped detection members 70 span at an angle over the opening section 74 disposed at the front end portion of the substrate 72 in the ejection testing unit 77 such that the detection members 70 intersect with the movement direction of the carriage 41. The plate-shaped detection members 70 are arranged in parallel to each other with a spacing therebetween. Herein, the spacings between the detection members 70 are equal to each other. Both end portions of each of the detection members 70 are fixed on the edge portions of the opening section 74. The detection members 70 are arranged in correspondence with the nozzles #1 to #180.

As shown in FIG. 37B, the ink droplet Ip ejected from each of the nozzles #1 to #180 of the head 21 passes through the gaps between the plate-shaped detection members 70 to drop downward. Accordingly, an induced current is generated at the plate-shaped detection members 70.

===Supplemental Remarks===

<Ink Recovery Section>

Figure 38:
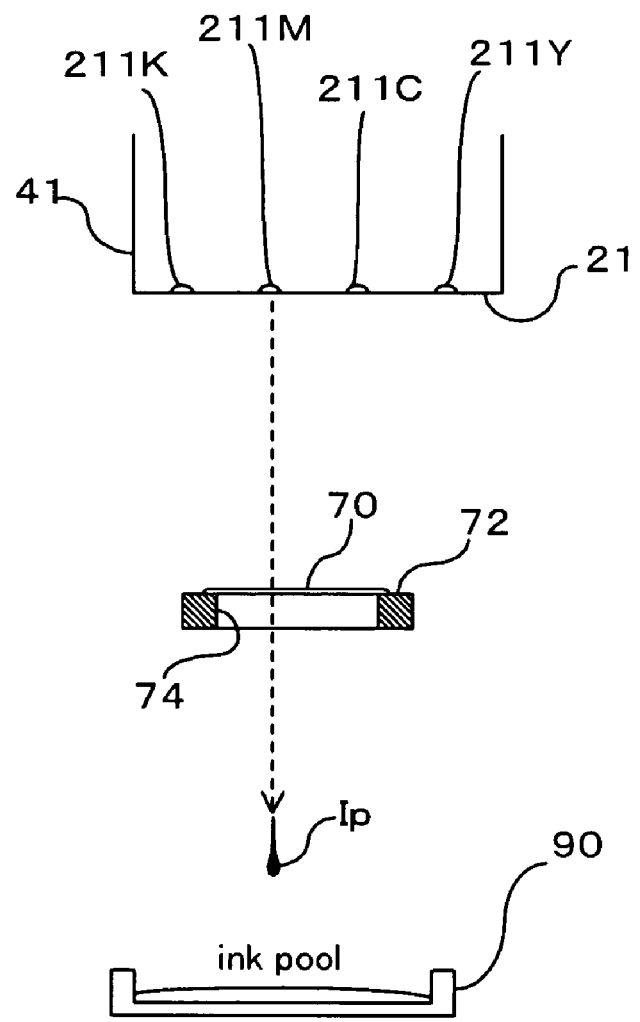
FIG. 38 is a view illustrating an example of an ink recovery section.

The inkjet printer 1 according to this embodiment is provided with an ink recovery section 90 for recovering ink used in the ejection test. FIG. 38 illustrates the ink recovery section 90. As shown in FIG. 38, the ink recovery section 90 is disposed, for example, below the substrate 72 provided with the detection members 70, and contains and recovers the ink droplet Ip that has been ejected from the nozzles #1 to #180 of the head 21, has passed by the side of the detection members 70, and has dropped through the opening section 74 of the substrate 72. It is possible to prevent the internal portion of the inkjet printer 1 from being soiled by ink, by recovering ink used in the ejection test in this manner with the ink recovery section 90.

It should be noted that although the ink recovery section 90 is formed as a concave containing section as shown in FIG. 38 in this embodiment, it is also possible to be provided as, for example, a grooved portion with a concave-shaped cross section on the platen 14, as long as ink used in the ejection test is recovered.

<Water Repellency Processing>

A water repellency processing may be performed on the surface of the detection members 70. When a water repellency processing is applied to the surface of the detection members 70 in this manner, it is possible to easily remove ink from the surface of the detection members 70 even when the ink droplet Ip ejected from the nozzles #1 to #180 is brought into contact with the detection members 70.

Furthermore, the water repellency processing may be performed also on the surface of the electrode section 112. When a water repellency processing is performed on the surface of the electrode section 112 in this manner, it is possible to easily remove ink from the surface of the electrode section 112 even when the ink droplet Ip ejected from the nozzles #1 to #180 is attached to the electrode section 112.

Example of the method for performing the water repellency processing include a method in which the surface of the detection members 70 or the electrode section 112 is coated with a water repellent layer, and other known methods.

<Earth Structure of Head>

Figure 39:
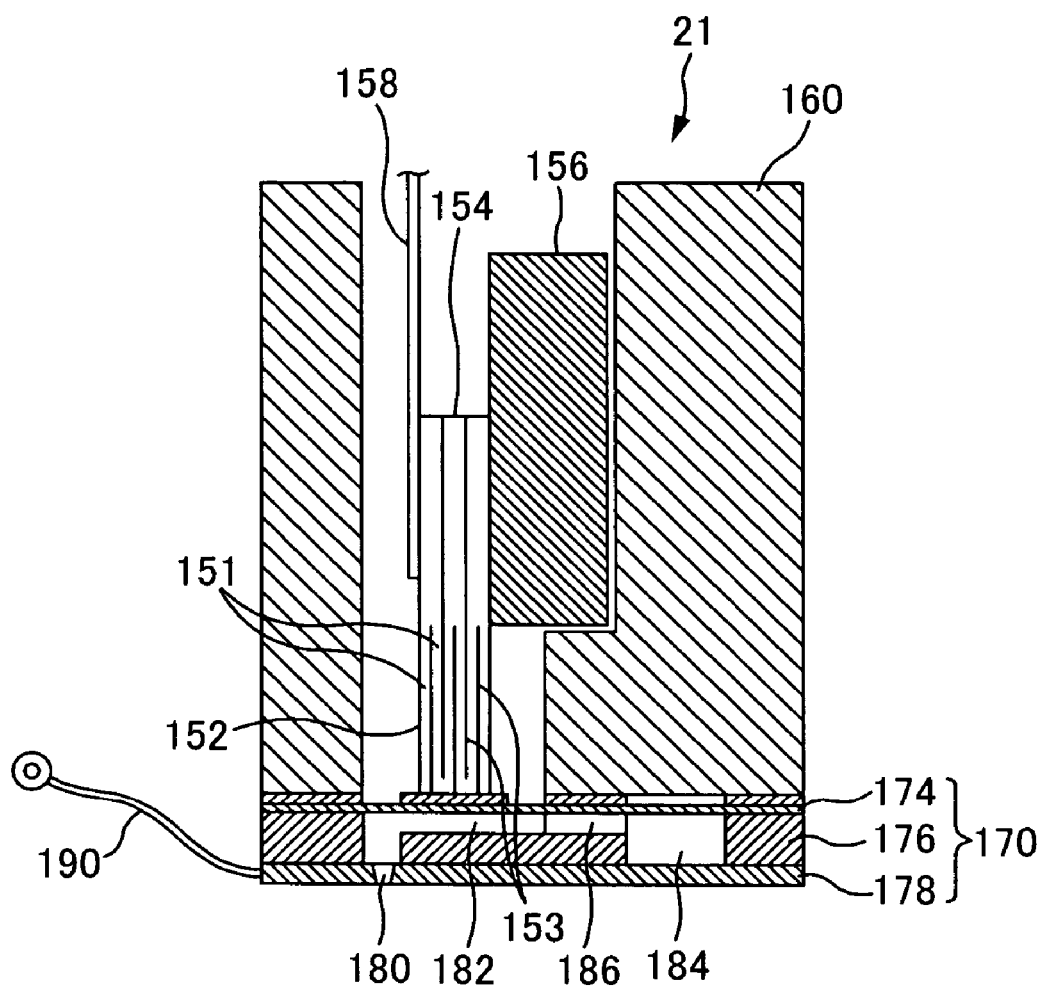
FIG. 39 is a view illustrating an example of a case in which the head is earthed.

The above-described head 21 may be electrically earthed (grounded). FIG. 39 illustrates an example of the earth structure of the head 21 and shows an example of the internal structure of the head 21. As shown in FIG. 39, the head 21 shown here is provided with a vibrator unit 150 in which a piezoelectric vibrator group 154 comprising a plurality of piezoelectric vibrators 152, a fixed plate 156, a flexible cable 158 and other components are included as a unit, a case 160 that can accommodate the vibrator unit 150, and a channel unit 170 that is attached on the front end face of the case 160.

The piezoelectric vibrators 152 serve as the above-described piezo elements. The piezoelectric vibrators 152 are constituted by alternate layers of piezoelectric substances 151 and internal electrodes 153, and are formed in the shape of an elongated comb in the longitudinal direction. The piezoelectric vibrators 152 are expanded or constricted in the longitudinal direction, that is, the longitudinal direction, in response to drive signals from the outside. The front end portions (lower end portions) of the piezoelectric vibrators 152 are connected via an insular part 172 to the channel unit 170.

The channel unit 170 comprises an elastic plate 174, a channel forming substrate 176 and a nozzle plate 178. The nozzle plate 178 is a thin plate made of stainless steel, for example, and has a large number of nozzle openings 180 (corresponding to nozzles #1 to #180) formed with a pre-determined pitch. The nozzle openings form the nozzles #1 to #180. The channel forming substrate 176 is provided with pressing compartments 182 formed in correspondence with the nozzle openings 180.

When the piezoelectric vibrators 152 are expanded or constricted, the elastic plate 172 is deformed to be curved upward or downward, so that the pressing compartments 182 are expanded or constricted. Thus, ink is supplied from ink supply compartments 184 through ink supply paths 186 to the pressing compartments 182. Ink that has been stored in the pressing compartments 182 is ejected as an ink droplet from the nozzle openings 180.

When the head 21 provided with such an ink ejection mechanism is earthed, the nozzle plate 178 of the channel unit 170 is connected to an earth line 190, and then the earth line 190 is connected to an appropriate metal member. If the guide rail 46 is made of metal, the earth line 190 is connected to the guide rail 46, for example. When the nozzle plate 178 is earthed via the earth line 190 in this manner, it is possible to easily earth the head 21.

===Configuration of Liquid Ejection System etc.===

Figure 40:
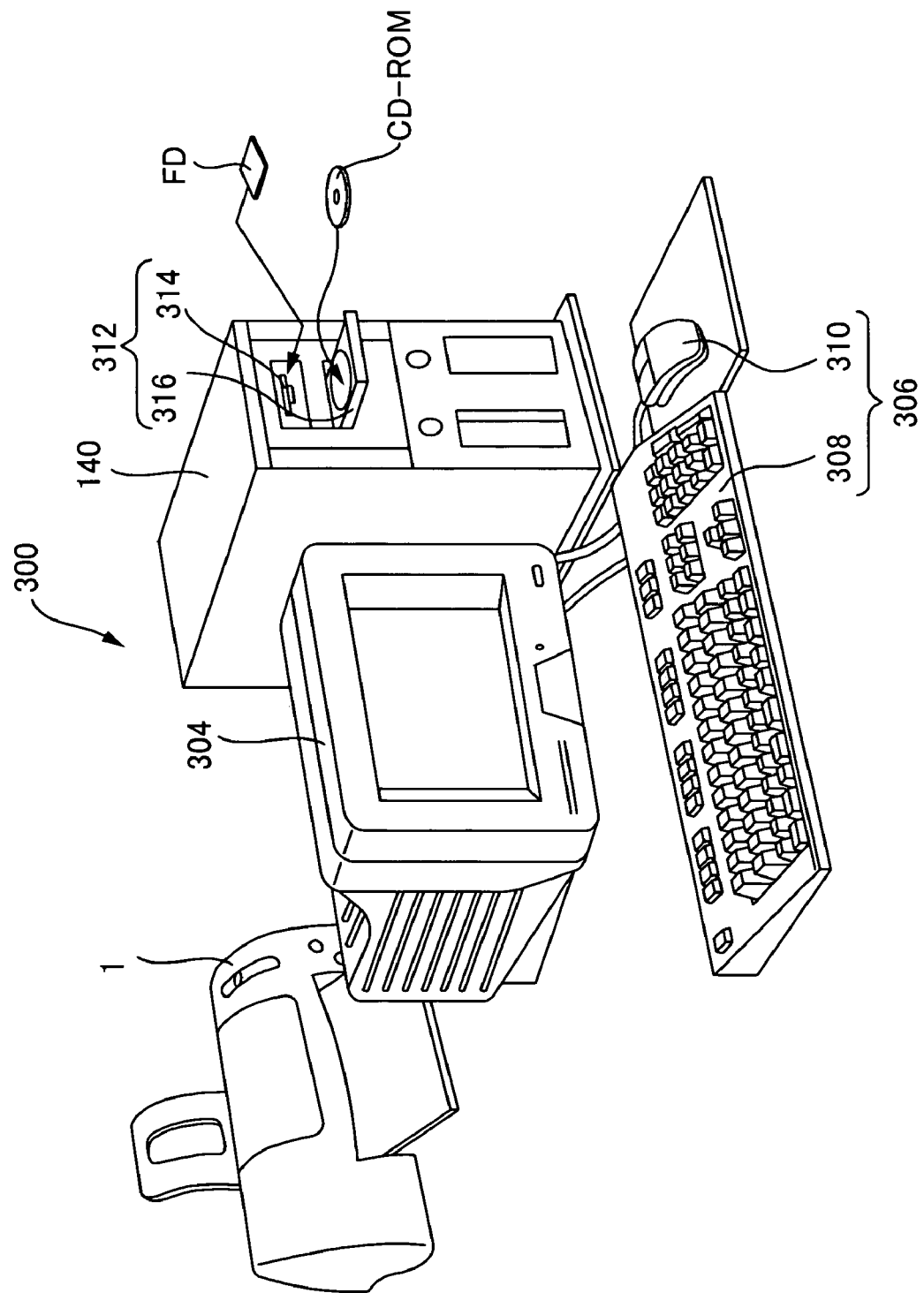
FIG. 40 is a perspective view showing the appearance of an example of a liquid ejection system.

The following is a description concerning an example in which the inkjet printer 1 is provided as a liquid ejecting apparatus, as an embodiment of a liquid ejection system according to the present invention. FIG. 40 shows the appearance configuration of an embodiment of a liquid ejection system according to the present invention. A liquid ejection system 300 is provided with the computer 140, a display device 304, and an input device 306. The computer 140 is constituted by various computers such as a personal computer.

The computer 140 is provided with a reading device 312 such as an FD drive 314 and a CD-ROM drive 316. In addition to the above, the computer 140 may be provided with, for example, an MO (magnet optical) disk drive and a DVD drive. Furthermore, the display device 304 is constituted by various display devices such as a CRT display, a plasma display, a liquid crystal display. The input device 306 is constituted by, for example, a key board 308 and a mouse 310.

Figure 41:
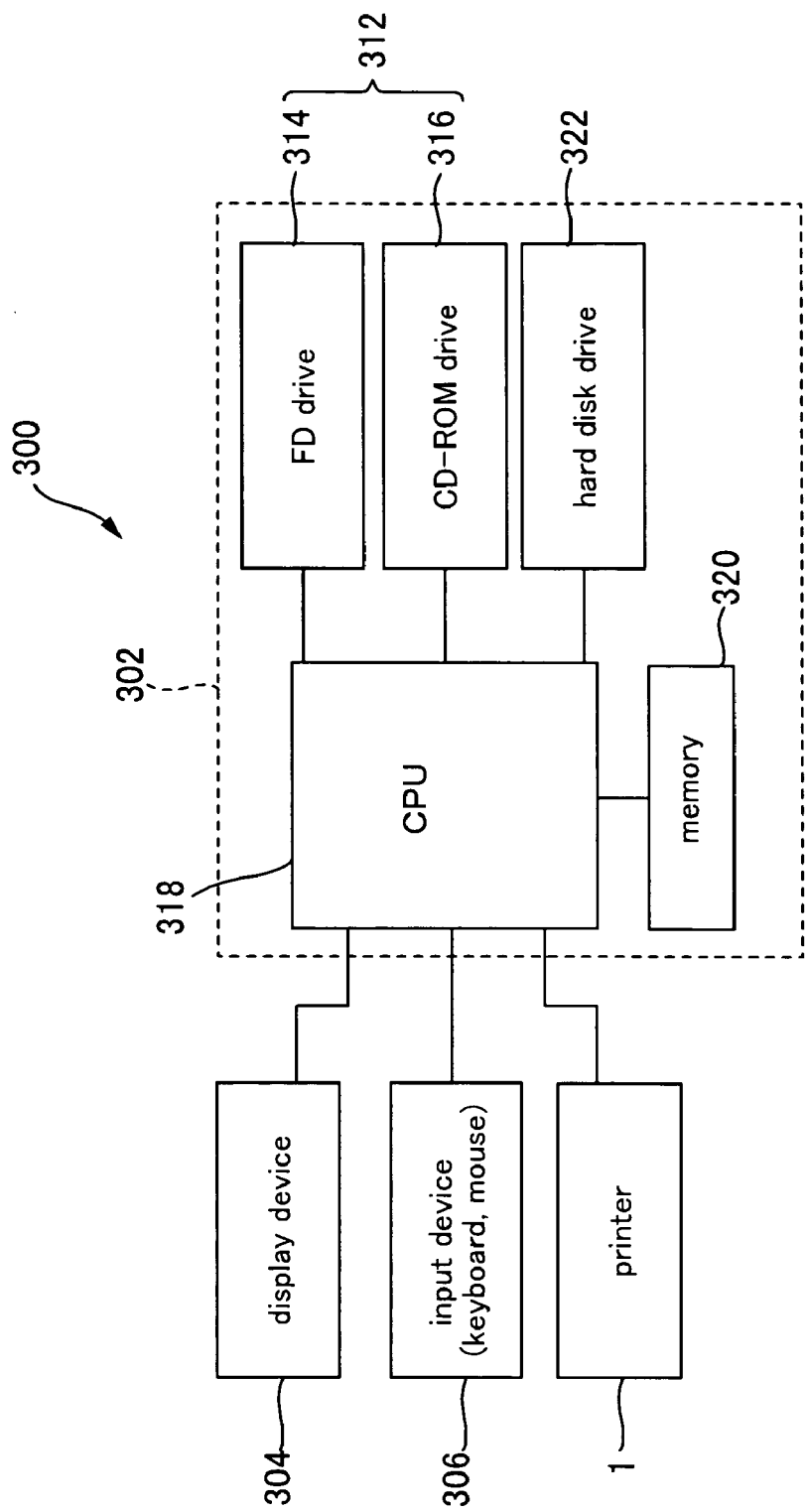
FIG. 41 is a block diagram showing the system configuration of an example of the liquid ejection system.

FIG. 41 is a block diagram showing an example of the system configuration of the liquid ejection system according to this embodiment. The computer 140 is provided with a CPU 318, a memory 320, and a hard disk drive 322 in addition to the reading device 312 such as the FD drive 314 and the CD-ROM drive 316.

The CPU 318 performs overall control of the computer 140. Furthermore, various types of data is stored in the memory 320. A printer driver, for example, as a program for controlling a liquid ejecting apparatus such as the inkjet printer 1 according to this embodiment is installed in the hard disk drive 322. The CPU 318 reads out a program such as the printer driver stored in the hard disk drive 322 and operates according to the program. Furthermore, the CPU 318 is connected to, for example, the display device 304, the input device 306, and the inkjet printer 1 arranged outside the computer 140.

As an overall system, the liquid ejection system 300 that is thus achieved is superior to conventional systems.

===Other Embodiments===

In the description above, based on an embodiment, a liquid-ejection testing device and other components according to the present invention were described by taking this device being mounted on the inkjet printer 1 as an example. However, the foregoing embodiment is for the purpose of elucidating the present invention and is not to be interpreted as limiting the present invention. The invention can of course be altered and improved without departing from the gist thereof and includes functional equivalents. In particular, the embodiments described below are also included in the liquid-ejection testing device and other components according to the present invention.

<Regarding the liquid>

In the foregoing embodiment, an example was described in which ink is used as "liquid", but the liquid is not limited to ink. Instead of ink, it is also possible to employ various other liquids such as metallic material, organic material (such as macromolecular material), magnetic material, conductive material, wiring material, film-formation material, electric ink, various types of processed liquid, and genetic solutions.

<Regarding the Head>

In the foregoing embodiment, a head disposed on an inkjet printer, that is, the head 21, which is disposed such that it can move relative to a medium and which has nozzles for ejecting ink toward the medium, was described as an example, but "head" is not limited to this head 21. More specifically, any head may be employed as long as it is a head disposed such that it can move in a predetermined direction.

Furthermore, any head may be employed as long as it is a moving member disposed such that it can move in a predetermined direction, and it is not necessarily required for the head to have other special functions or roles, for example.

<Regarding the Liquid Ejecting Nozzles>

In the foregoing embodiment, "liquid ejecting nozzles" was described by taking the nozzles #1 to #180 ejecting ink as an example, but the liquid ejecting nozzles are not limited to such nozzles that eject ink. More specifically, it is also possible to employ nozzles that eject, as the liquid, various other liquids than ink such as metallic material, organic material (such as macromolecular material), magnetic material, conductive material, wiring material, film-formation material, electric ink, various types of processed liquid, and genetic solutions, as described above.

Furthermore, in the foregoing embodiment, the liquid ejecting nozzles were described using an example in which the nozzles #1 to #180 that eject ink are arranged in one straight line with a spacing therebetween in the carrying direction of the medium S, but it is not necessarily required that the liquid ejecting nozzles are arranged in this manner. More specifically, the liquid ejecting nozzles may be arranged in a manner different from this, and there is no special requirement for the arrangement of the nozzles.

<Regarding the Liquid Ejecting Section>

In the foregoing embodiment, "liquid ejecting section" was described by taking a nozzle row constituted by a plurality of nozzles as an example, but the liquid ejecting section is not limited to such a nozzle row. More specifically, it is not necessary that the liquid ejecting section is constituted by a plurality of nozzles arranged in a straight line in a predetermined direction as in the foregoing embodiment, and thus the plurality of nozzles may be arranged in any manner. Furthermore, it is not necessarily required that the number of nozzles is plural, and thus the number may be one. Furthermore, a liquid ejecting section of any form may be employed as long as it ejects a liquid.

Furthermore, in the foregoing embodiment, the liquid ejecting section was constituted by one nozzle row, but the configuration is not limited to this. More specifically, the liquid ejecting section may be constituted by two or more nozzle rows.

Furthermore, in the foregoing embodiment, the liquid ejecting sections were separately employed for each color of ink that is to be ejected, but the liquid ejecting sections are not limited to such a configuration in which each of them ejects ink of a different color. More specifically, two or more liquid ejecting sections may be employed that eject ink of the same color. For example, two or more liquid ejecting sections may be employed that eject ink of cyan (C).

<Regarding the Detection Members (1)>

In the foregoing embodiment, the detection members 70 were made of wire materials having a diameter of about 0.2 mm, or plate-shaped members having a thickness of about 0.2 mm and a width of about 3 mm, for example, but the form and the size of "detection members" are not limited to this. More specifically, the detection members may be made of materials of other shapes than those of wire materials and plate-shaped members, and may have other sizes.

Furthermore, in the foregoing embodiment, the detection members 70 spanned over the opening section 74 disposed at the substrate 72, but it is not necessarily required that the detection members are arranged in this manner. More specifically, the detection members may be arranged in any manner as long as it is possible to detect ink ejected from the liquid ejecting nozzles (nozzles #1 to #180).

Furthermore, in the foregoing embodiment, the number of the detection members 70 was ten or larger, but it is not necessarily required to provide the detection members of such a number because it suffices that the number of the detection members is two or larger. It goes without saying that it is preferable to set the number of the detection members to a large number to the extent possible, in accordance with the number of nozzles that are to be tested.

<Regarding the Arrangement of the Detection Members>

In the foregoing embodiment, an example was described in which two or more detection members 70 are arranged in parallel to each other with an equal spacing therebetween, but it is not necessarily required that "two or more detection members" are arranged in this manner. More specifically, it is not necessarily required that the two or more detection members are arranged in parallel to each other as long as they are arranged in the direction that intersects with the arrangement direction of the liquid ejecting nozzles. They may be arranged in directions that are different from each other, may be arranged with a spacing therebetween that is not an equal spacing, or may be arranged so as to intersect with each other.

<Regarding the Arrangement Direction of the Detection Members>

The direction in which the detection members are arranged is not limited to the direction as described as an example in the foregoing embodiment, and may be any direction as long as it is the direction that intersects with the arrangement direction of the nozzles #1 to #180.

<Regarding the Detecting Section>

In the foregoing embodiment, the detecting sections 80, 102, and 114 that detect an induced current generated at the detection members 70 were described as "detecting section", but the detecting section is not limited to these detecting sections 80, 102, and 114, and a detecting section of any type may be employed as long as it can detect an induced current generated at the detection members 70 with a charged liquid (ink) ejected from the liquid ejecting nozzles (nozzles #1 to #180 in this embodiment).

<Regarding the Detection Members (2)>

In the foregoing embodiment, the detection members 70 made of conductive wire materials or plate-shaped members such as metal were described as an example of sensing sections that detect ink ejected from each of the nozzles #1 to #180, but it is not necessarily required that they are formed in this shape. Furthermore, wire materials having a diameter of about 0.2 mm, or plate-shaped members having a thickness of about 0.2 mm and a width of about 3 mm were described regarding an example of the size of the detection members 70, but the size is not necessarily limited to these. More specifically, the sensing sections that detect ink ejected from each of the nozzles #1 to #180 may be made of materials of other shapes than those of wire materials and plate-shaped members, and may have other sizes as long as they are detection members at which an induced current is generated with charged ink ejected from each of the nozzles #1 to #180.

<Regarding the Judging Section>

In the foregoing embodiment, the judgment of whether or not ink is properly ejected from the nozzles #1 to #180 was performed by the controller 126 that performs overall control of the inkjet printer 1 (printing apparatus), but it is not necessarily required that the judgment of whether or not ink is properly ejected from the nozzles #1 to #180 is performed by this controller 126. More specifically, "judging section" that judges whether or not ink (liquid) is properly ejected is not limited to this controller 126. It may have a configuration different from that of the controller 126, or a dedicated configuration for judging whether or not ink (liquid) is properly ejected may be provided.

<Regarding the First Testing Section and the Second Testing Section>

In the foregoing embodiment, the liquid ejecting section was constituted by one nozzle row, and thus each of the first testing section and the second testing section is opposed to one nozzle row to perform the test separately on the one nozzle row. However, if the liquid ejecting section is constituted by two or more nozzle rows, then each testing section may be opposed to two or more nozzle rows to each perform the test on the two or more nozzle rows.

Furthermore, in the foregoing embodiment, each of the first testing section and the second testing section detected an induced current generated with charged ink (liquid) ejected from the nozzles #1 to #180 ("liquid ejecting section") to test whether or not ink (liquid) is properly ejected from the nozzles #1 to #180 ("liquid ejecting section"), but other methods may be employed as a method by which "first testing section" and "second testing section" test whether or not ink (liquid) is properly ejected from the nozzles #1 to #180 ("liquid ejecting section"). More specifically, the first testing section and the second testing section may test whether or not ink (liquid) is properly ejected from the nozzles #1 to #180 using laser light, for example, or may test whether or not ink (liquid) is properly ejected using other methods, for example.

Furthermore, in the foregoing embodiment, each of the first testing section and the second testing section performed the test on the same nozzle row ("liquid ejecting section"), but each of the first testing section and the second testing section may perform the test on a different nozzle row ("liquid ejecting section"). More specifically, a nozzle row ("liquid ejecting section") that is to be tested by the first testing section may be different from that to be tested by the second testing section. In this case, the process speed of the test is significantly improved.

In addition to the above, each of the first testing section and the second testing section may perform a different test. More specifically, the configuration may be such that while the first testing section tests whether or not ink (liquid) is ejected from the nozzles #1 to #180 of a nozzle row ("liquid ejecting section"), the second testing section tests whether or not the ejection direction of ink (liquid) from the nozzles #1 to #180 of a nozzle row ("liquid ejecting section") is proper, for example.

<Regarding the Electrode Section>

In the foregoing embodiment, the electrode section 112 made of a wire material was described as "electrode section", but the electrode section is not limited to this electrode section 112. An electrode section of any form may be employed as long as it forms an electric field with the nozzles #1 to #180 (head 21).

<Regarding the Liquid-ejection Testing Device>

In the foregoing embodiment, a liquid-ejection testing device mounted on a liquid ejecting apparatus such as the ink jet printer was described as a liquid-ejection testing device, but the liquid-ejection testing device is not limited to such a device. It may be a device that is separated from the liquid ejecting apparatus such that it can independently perform only the ejection test of a liquid, or may be a liquid-ejection testing device that is mounted on other devices than the above-described liquid ejecting apparatus.

<Regarding the Liquid Ejecting Apparatus>

In the foregoing embodiment, a liquid-ejection testing device was described by taking the inkjet printer 1 as an example, but it is not limited to this inkjet printer 1. Any apparatus may be employed as long as it is an apparatus that ejects a liquid.

<Regarding the Ink>

The ink that is used may be pigment ink or may be various other types of ink such as dye ink.

As for the color of the ink, it is also possible to use ink of other colors, such as light cyan (LC), light magenta (LM), dark yellow (DY), or red, violet, blue or green, in addition to the above-mentioned yellow (Y), magenta (M), cyan (C) and black (K).

<Regarding the Printing Apparatus>

In the foregoing embodiment, a printing apparatus was described by taking the above-described inkjet printer 1 as an example, but it is not limited to such a printing apparatus, and an inkjet printer for ejecting ink in other modes also may be employed.

<Regarding the Medium>

The medium S may be any of plain paper, matte paper, cut paper, glossy paper, roll paper, print paper, photo paper, and roll-type photo paper or the like. In addition to these, the medium S may be a film material such as OHP film and glossy film, a cloth material, or a metal plate material or the like. In other words, any medium that can be printed on may be employed.

What is claimed is:

1. A liquid-ejection testing method, comprising:
a step of making at least two conductive detection members be opposed, in a non-contact state, to a plurality of liquid ejecting nozzles that are to be tested, the detection members being opposed in a direction that intersects with a direction in which the plurality of liquid ejecting nozzles are arranged, each detection member corresponding to a different liquid ejecting nozzle,
a step of ejecting a charged liquid from each of the plurality of liquid ejecting nozzles,
a step of detecting an induced current generated at each of the detection members by the liquid that has been ejected from each of the liquid ejecting nozzles, and
a step of judging whether or not ejection of the liquid is being properly performed for each of the plurality of liquid ejecting nozzles, based on a magnitude of the induced current that has been detected.

2. A liquid-ejection testing method according to claim 1, wherein the detection members are made of a plate-shaped member or a wire material.

3. A liquid-ejection testing method according to claim 1, wherein the at least two detection members are arranged in parallel to each other.

4. A liquid-ejection testing method according to claim 3, wherein spacings between the at least two detection members are equal to each other.

5. A liquid-ejection testing method according to claim 1, wherein the at least two detection members span over an opening section provided in a substrate.

6. A liquid-ejection testing method according to claim 1, wherein the at least two detection members are electrically connected to each other via a common line.

7. A liquid-ejection testing method according to claim 6, wherein the common line is connected to a detecting section for detecting the induced current that has been generated at the detection members.

8. A liquid-ejection testing method according to claim 6, wherein the common line is connected to one end portion of each of the detection members.

9. A liquid-ejection testing method according to claim 1, wherein judgment is performed by comparing the magnitude of the induced current that has been detected and a predetermined reference value.

10. A liquid-ejection testing method according to claim 1, wherein whether or not the liquid is ejected from the liquid ejecting nozzles is judged based on the magnitude of the induced current that has been detected.

11. A liquid-ejection testing method according to claim 1, wherein whether or not an ejection direction of the liquid from the liquid ejecting nozzles is proper is judged based on the magnitude of the induced current that has been detected.

12. A liquid-ejection testing method according to claim 1, wherein a voltage is applied to the detection members in order to charge the liquid ejected from the liquid ejecting nozzles.

13. A liquid-ejection testing method according to claim 1, wherein the liquid ejected from the liquid ejecting nozzles is charged by an electrode section to which a voltage is applied.

14. A liquid-ejection testing method according to claim 1, further comprising:
a step of changing a relative position between the plurality of liquid ejecting nozzles and the at least two detection members.

15. A liquid-ejection testing device, comprising:
at least two conductive detection members that are arranged in a direction that intersects with a direction in which a plurality of liquid ejecting nozzles that are to be tested are arranged, the at least two detection members being arranged in a state of non-contact with respect to the plurality of liquid ejecting nozzles, each of the detection members being provided corresponding to a different liquid ejecting nozzle, a detecting section for detecting an induced current generated at each of the detection members by a charged liquid ejected from each of the plurality of liquid ejecting nozzles, and a judging section for judging whether or not ejection of the liquid is being properly performed for each of the plurality of liquid ejecting nozzles, based on a magnitude of the induced current that has been detected by the detecting section.

16. A liquid-ejection testing device according to claim 15, wherein the plurality of liquid ejecting nozzles eject link as the liquid and are arranged in a printing apparatus.

17. A computer-readable medium for causing a liquid-ejection testing device to operate, comprising:

a code for ejecting a charged liquid from each of a plurality of liquid ejecting nozzles that are to be tested and that are arranged in a predetermined direction, a code for acquiring a magnitude of an induced current generated by the liquid that has been ejected from each of the liquid ejecting nozzles at at least two conductive detection members that are arranged in a direction that intersects with the predetermined direction, the detection members being arranged in a state of non-contact with respect to the plurality of liquid ejecting nozzles, each detection member corresponding to a different liquid ejecting nozzle, and a code for judging whether or not ejection of the liquid is being properly performed for each of the plurality of liquid ejecting nozzles, based on the magnitude of the induced current that has been acquired.

* * * * *